(12) United States Patent
Baettig et al.

(10) Patent No.: US 7,989,497 B2
(45) Date of Patent: Aug. 2, 2011

(54) SQUARAMIDE DERIVATIVES AS CXCR2 ANTAGONIST

(75) Inventors: Urs Baettig, Horsham (GB); Anne-Marie D'Souza, Horsham (GB); Peter Hunt, Horsham (GB); Neil John Press, Horsham (GB); Simon James Watson, Horsham (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/512,609

(22) Filed: Jul. 30, 2009

(65) Prior Publication Data

US 2010/0029670 A1 Feb. 4, 2010

Related U.S. Application Data

(60) Provisional application No. 61/161,627, filed on Mar. 19, 2009.

(30) Foreign Application Priority Data

Aug. 4, 2008 (EP) .................................... 08161765

(51) Int. Cl.
A61K 31/18 (2006.01)
(52) U.S. Cl. ..... 514/604; 544/336; 546/329; 548/375.1; 549/74; 549/491; 549/505; 564/86
(58) Field of Classification Search .................. 514/604; 544/336; 546/329; 548/375.1; 549/74, 491, 549/505; 564/86
See application file for complete search history.

(56) References Cited

U.S. PATENT DOCUMENTS

| 6,166,050 | A | 12/2000 | Lombardo et al. |
| 7,132,445 | B2 | 11/2006 | Taveras et al. |
| 2004/0106794 | A1 | 6/2004 | Taveras et al. |
| 2004/0147559 | A1 | 7/2004 | Taveras et al. |
| 2008/0200523 | A1 | 8/2008 | Murthi et al. |

FOREIGN PATENT DOCUMENTS

| DE | 102005035742 A1 | 2/2007 |
| EP | 1818325 B1 | 2/2010 |
| WO | 02/057230 A1 | 7/2002 |
| WO | 02/079122 A2 | 10/2002 |
| WO | 02/083624 A1 | 10/2002 |
| WO | 03/080053 A1 | 10/2003 |
| WO | 2004/011418 A1 | 2/2004 |
| WO | 2005/075447 A1 | 8/2005 |
| WO | 2006/072354 A1 | 7/2006 |
| WO | 2006/084661 A1 | 8/2006 |
| WO | 2006/088920 A1 | 8/2006 |
| WO | 2008/005570 A1 | 1/2008 |
| WO | 2009/005801 A1 | 1/2009 |
| WO | 2009/005802 A1 | 1/2009 |
| WO | 2009/012375 A2 | 1/2009 |
| WO | 2009/073683 A2 | 6/2009 |
| WO | 2010/683802 A1 | 6/2010 |
| WO | 2010/091543 A1 | 8/2010 |

OTHER PUBLICATIONS

Yun Feng Xie et al., "Structure-activity relationships of novel, highly potent, selective, and orally active CCR1 antogonists," Bioorganic & Medicinal Chemistry Letters 15:3367-3372 (Apr. 5, 2007).

Primary Examiner — James O Wilson
Assistant Examiner — Douglas M Willis
(74) Attorney, Agent, or Firm — Theresa A. Devlin; Mark Milstead

(57) ABSTRACT

The present invention relates to compounds of formula (I)

(I)

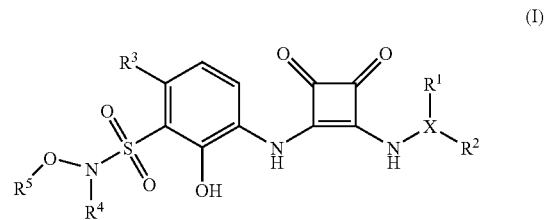

wherein X, $R^1$, $R^2$, $R^3$, $R^4$ and $R^5$ are as defined herein, which are useful for treating diseases which respond to CXCR2 receptor mediators. Pharmaceutical compositions that contain the compounds and processes for preparing the compounds are also described.

16 Claims, No Drawings

SQUARAMIDE DERIVATIVES AS CXCR2 ANTAGONIST

This application claims benefit under 35 U.S.C. §119(a)-(d) or (f) or 365(b) of EP Application No. 08161765.6, filed Aug. 4, 2008, and benefit under 35 U.S.C. §119(e) of U.S. Provisional Application No. 61/161,627, filed Mar. 19, 2009, the contents of which are incorporated herein by reference in their entirety.

BRIEF SUMMARY OF THE INVENTION

The present invention relates to organic compounds, e.g. compounds of formula (I), and uses thereof.

DETAILED DESCRIPTION OF THE INVENTION

In one aspect the present invention provides a compound of formula I

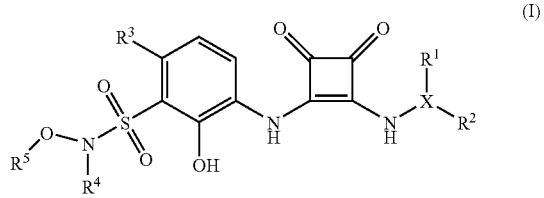

or solvates, hydrates or pharmaceutically acceptable salts thereof, wherein $R^1$ is H, a 3 to 10 membered carbocyclic group optionally substituted by one or more Z groups, a 3 to 10 membered heterocyclic group optionally substituted by one or more Z groups, ($C_1$-$C_4$ alkyl)- 3 to 10 membered carbocyclic group optionally substituted by one or more Z groups, ($C_1$-$C_4$ alkyl)- 3 to 10 membered heterocyclic group optionally substituted by one or more Z groups, $C_1$-$C_6$ alkyl optionally substituted by one or more halogen atoms, CN or OH groups, $C_1$-$C_6$ alkoxy optionally substituted by one or more halogen atoms or OH groups, or an ether group containing 2 to 10 carbon atoms and 1 to 3 oxygen atoms, wherein the ether group is optionally substituted by one or more substituents each independently selected from OH, halogen, a 3 to 10 membered carbocyclic group optionally substituted by one or more Z groups and a 3 to 10 membered heterocyclic group optionally substituted by one or more Z groups;

$R^2$ is a 3 to 10 membered carbocyclic group optionally substituted by one or more Z groups, a 3 to 10 membered heterocyclic group optionally substituted by one or more Z groups, ($C_1$-$C_4$ alkyl)- 3 to 10 membered carbocyclic group optionally substituted by one or more Z groups, ($C_1$-$C_4$ alkyl)- 3 to 10 membered heterocyclic group optionally substituted by one or more Z groups, $C_1$-$C_6$ alkyl optionally substituted by one or more halogen atoms, CN or OH groups, $C_1$-$C_6$ alkoxy optionally substituted by one or more halogen atoms or OH groups, or an ether group containing 2 to 10 carbon atoms and 1 to 3 oxygen atoms, wherein the ether group is optionally substituted by one or more substituents each independently selected from OH, halogen, a 3 to 10 membered carbocyclic group optionally substituted by one or more Z groups and a 3 to 10 membered heterocyclic group optionally substituted by one or more Z groups; or $R^1$ and $R^2$ together with the carbon atom to which they are attached form 3 to 10 membered carbocyclic group optionally substituted by one or more Z groups, or a 3 to 10 membered heterocyclic group optionally substituted by one or more Z groups;

$R^3$ is hydrogen, halogen or cyano;

$R^4$ is H, $C_1$-$C_8$ alkyl, $C_3$-$C_8$ cycloalkyl, $C_5$-$C_8$ cycloalkenyl or ($C_1$-$C_4$ alkyl)-$R^6$, wherein the alkyl groups are each optionally substituted by one or more halogen atoms;

$R^5$ is $C_1$-$C_8$ alkyl, $C_3$-$C_8$ cycloalkyl, $C_5$-$C_8$ cycloalkenyl, ($C_1$-$C_4$ alkyl)-$C_3$-$C_8$ cycloalkyl or ($C_1$-$C_4$ alkyl)-$C_5$-$C_8$ cycloalkenyl, wherein the alkyl groups are each optionally substituted by one or more halogen atoms; or $R^4$ and $R^5$, together with the nitrogen and oxygen atoms to which they are attached, form a 5 to 10 membered heterocyclic group optionally substituted by one or more Z groups;

$R^6$ is selected from a 3 to 10 membered carbocyclic group optionally substituted by one or more Z groups, a 3 to 10 membered heterocyclic group optionally substituted by one or more Z groups, $NR^7R^9$, $NR^7(SO_2)R^9$, $(SO_2)NR^7R^8$, $(SO_2)R^9$, $NR^7C(O)R^9$, $C(O)NR^7R^9$, $NR^7C(O)NR^8R^9$, $NR^7C(O)OR^9$, $C(O)OR^7$, $OC(O)R^9$, $OC(O)NR^7$, $C(O)R^9$, $SR^7$, CN and $NO_2$;

$R^7$ and $R^8$ are each independently selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl;

$R^9$ is selected from H, $C_1$-$C_6$ alkyl, —($C_1$-$C_3$ alkylene)-$C_3$-$C_{10}$ cycloalkyl, a 3 to 10 carbocyclic group and a 3 to 10 membered heterocyclic group, wherein each of the alkyl groups and ring systems is optionally substituted by OH, halo, $C_1$-$C_3$ alkyl and $C_1$-$C_3$ alkoxy;

X is $CR^{14}$ or N;

Z is independently selected from OH; a 3 to 10 membered carbocyclic group; a 3 to 10 membered heterocyclic group; benzyl; $C_1$-$C_6$ alkyl optionally substituted by one or more halogen atoms, CN or OH groups; $C_1$-$C_6$ alkoxy optionally substituted by one or more halogen atoms, CN or OH groups; —Oaryl; —Obenzyl; —$O(CH_2)_aC(O)E$; $NR^{10}(SO_2)R^{12}$; $(SO_2)NR^{10}R^{11}$;

$(SO_2)R^{12}$; $NR^{10}C(O)R^{12}$; $C(O)NR^{10}OR^{12}$; $NR^{10}C(O)NR^{11}R^{12}$; $NR^{10}C(O)OR^{12}$; $NR^{10}R^{12}$;

$C(O)OR^{10}$; $OC(O)R^{12}$; $OC(O)NR^{10}$; $C(O)R^{12}$; $SR^{12}$; CN; $NO_2$; and halogen; or where there are two or more Z substituents, two Z substituents together with the atoms to which they are attached optionally form a 5- to 7-membered carbocyclic or a 4- to 7-membered heterocyclic substituent fused to the ring system;

a is 0, 1, 2, 3 or 4, wherein the alkylene group is optionally substituted by OH or $NH_2$ when a is 1, 2, 3 or 4;

E is $NR^{10}R^{12}$ or $OR^{12}$;

each $R^{10}$ and $R^{11}$ are independently selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl;

each R is selected from H, $C_1$-$C_6$ alkyl, —($C_1$-$C_3$ alkylene)-$C_3$-$C_{10}$ cycloalkyl, a 3 to 10 membered carbocyclic group and a 3 to 10 membered heterocyclic group, wherein each of the ring systems is optionally substituted by OH, halo, $C_1$-$C_3$ alkyl and $C_1$-$C_3$ alkoxy; and $R^{14}$ is H or $C_1$-$C_6$ alkyl.

In an embodiment of the invention, $R^1$ is H or $C_1$-$C_4$ alkyl and the other variables are as defined anywhere herein.

In a further embodiment of the invention, $R^2$ is $C_1$-$C_6$ alkyl optionally substituted by one or more halogen atoms, CN or OH groups, an ether group containing 2 to 10 carbon atoms and 1 to 3 oxygen atoms, a 4 to 6 membered carbocyclic group optionally substituted by one or more Z groups, or a 4 to 6 membered heterocyclic group optionally substituted by one or more Z groups; and the other variables are as defined anywhere herein.

In a further embodiment of the invention, $R^1$ and $R^2$, together with the carbon atom to which they are attached form a 4 to 6 membered carbocyclic group optionally substituted by one or more Z groups or a 4 to 6 membered heterocyclic group optionally substituted by one or more Z groups; and the other variables are as defined anywhere herein.

In a further embodiment of the invention, $R^3$ is halogen, suitably chlorine; and the other variables are as defined anywhere herein.

In a further embodiment of the invention, $R^4$ is H, $C_1$-$C_4$ alkyl, $C_3$-$C_6$ cycloalkyl or ($C_1$-$C_3$ alkyl)-$C_3$-$C_6$ cycloalkyl; and the other variables are as defined anywhere herein.

In a further embodiment of the invention, $R^5$ is $C_1$-$C_6$ alkyl, suitably $C_1$-$C_4$ alkyl, more suitably $C_1$-$C_3$ alkyl; and the other variables are as defined anywhere herein.

In a further embodiment, $R^4$ and $R^5$, together with the nitrogen and oxygen atoms to which they are attached form a 5 or 6 membered heterocyclic group. Suitably, $R^4$ and $R^5$, together with the nitrogen and oxygen atoms to which they are attached form a 5-membered heterocyclic group.

In a further embodiment, X is $CR^{14}$, wherein $R^{14}$ is H or $C_1$-$C_6$ alkyl. Optionally, $R^{14}$ is H or methyl. Suitably X is CH.

In a further embodiment of the invention, Z is selected from $C_1$-$C_4$ alkyl optionally substituted by one or more halogen atoms or OH groups, $C_1$-$C_4$ alkoxy optionally substituted by one or more halogen atoms or OH groups, halogen, OH and $NR^{10}OR^{12}$, wherein $R^{10}$, $R^{12}$ and the other variables are all as defined anywhere herein.

Reference to "the other variables are all as defined anywhere herein" will be understood to mean that all of the other variables used in the definition of the compounds of Formula I can have any of the definitions applied to them hereinabove or in the claims. Thus, combinations of sub-definitions of the variables are considered to be within the scope of the invention. In particular, the definition of a variable in an embodiment of the invention may be combined with the definition of a second variable from a separate embodiment of the invention.

In a further embodiment, the present invention provides a compound of formula (I) selected from:

| Structure |
|---|
| 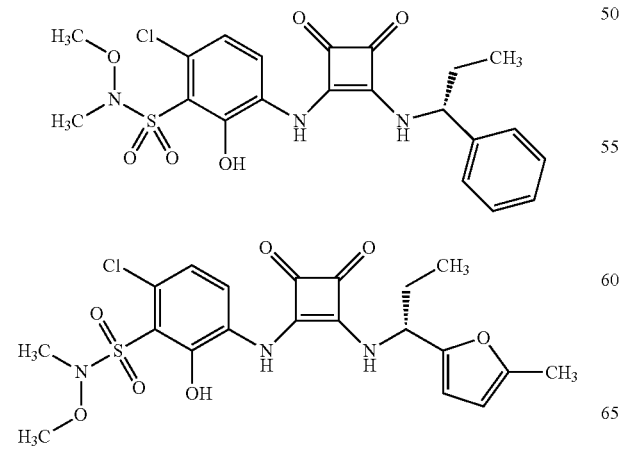 |

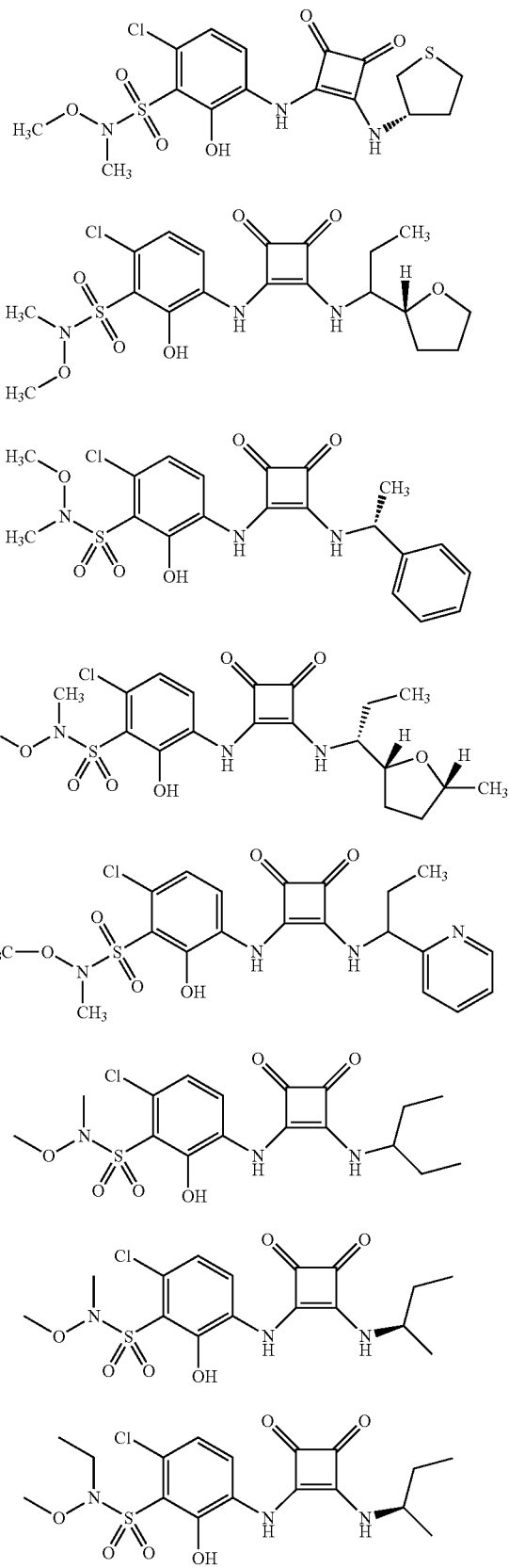

-continued
| Structure |
|---|
| 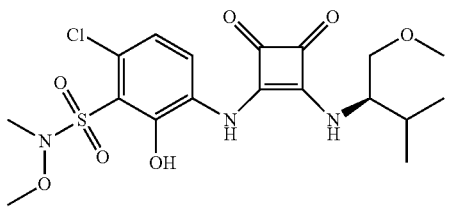 |
| 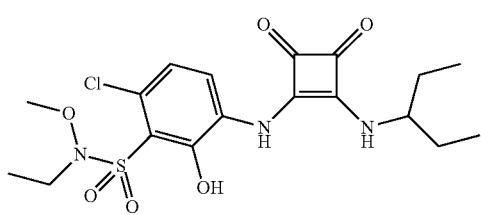 |
| 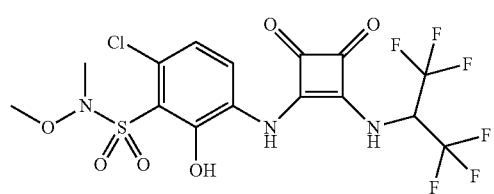 |
| 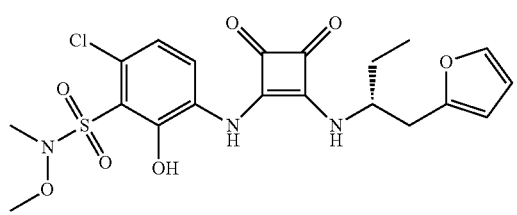 |
| 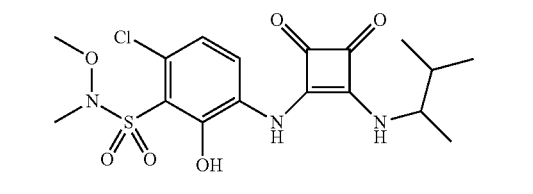 |
| 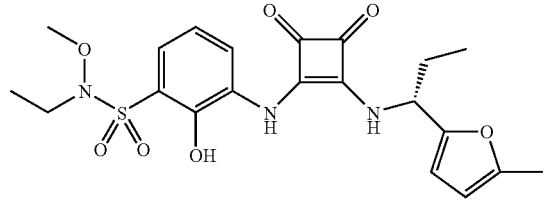 |
| 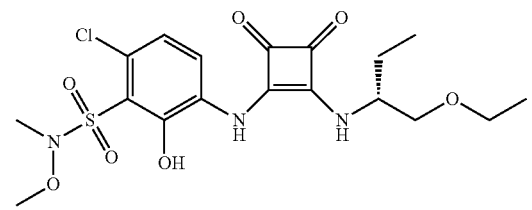 |
-continued
| Structure |
|---|
| 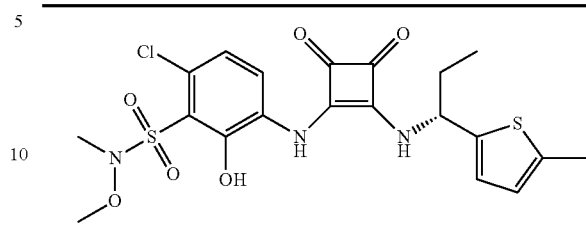 |
| 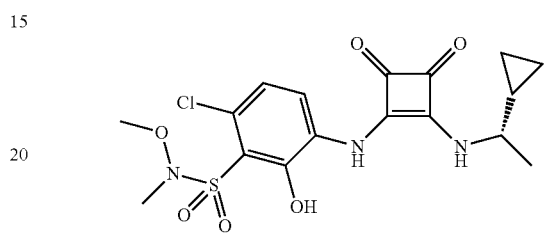 |
| 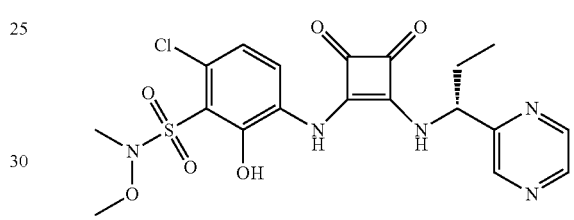 |
| 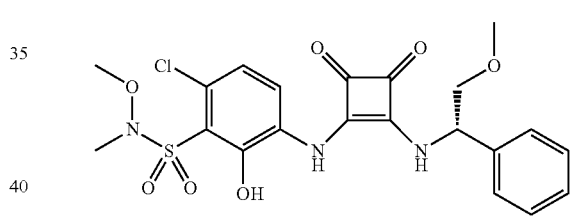 |
| 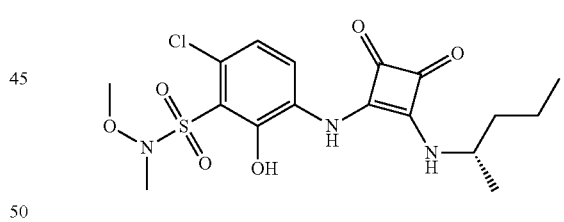 |
| 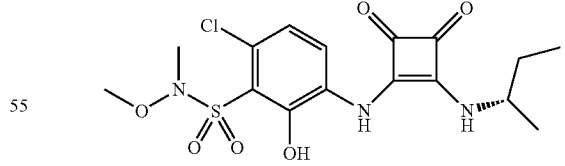 |
| 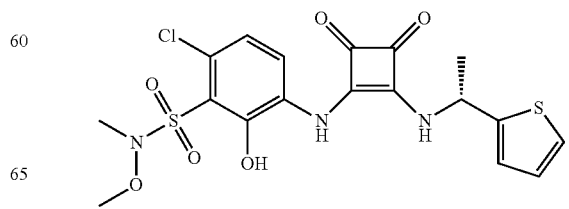 |

| 7 -continued | 8 -continued |
|---|---|
| Structure | Structure |
| 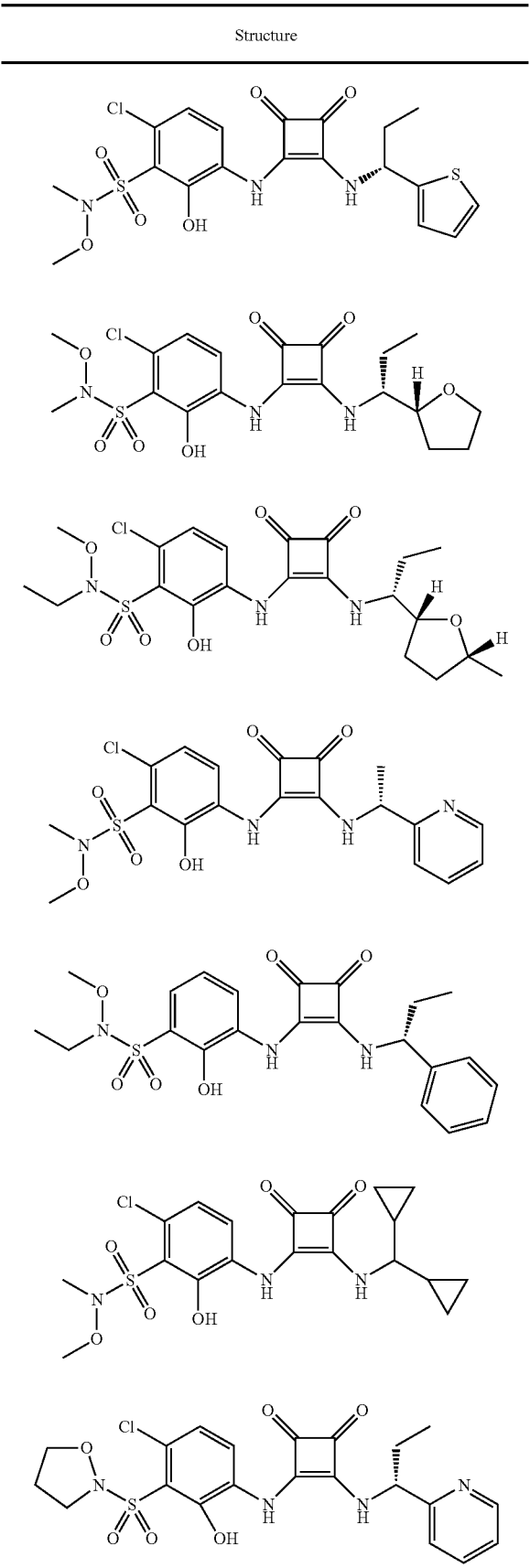 | 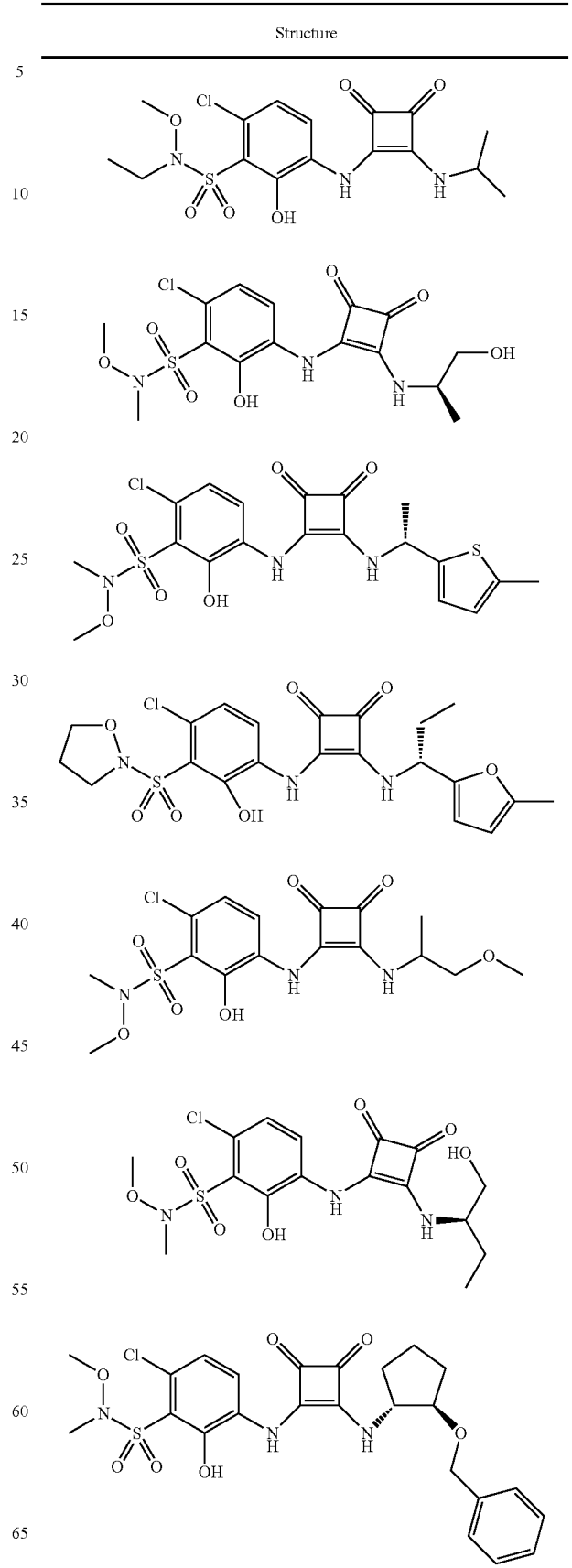 |

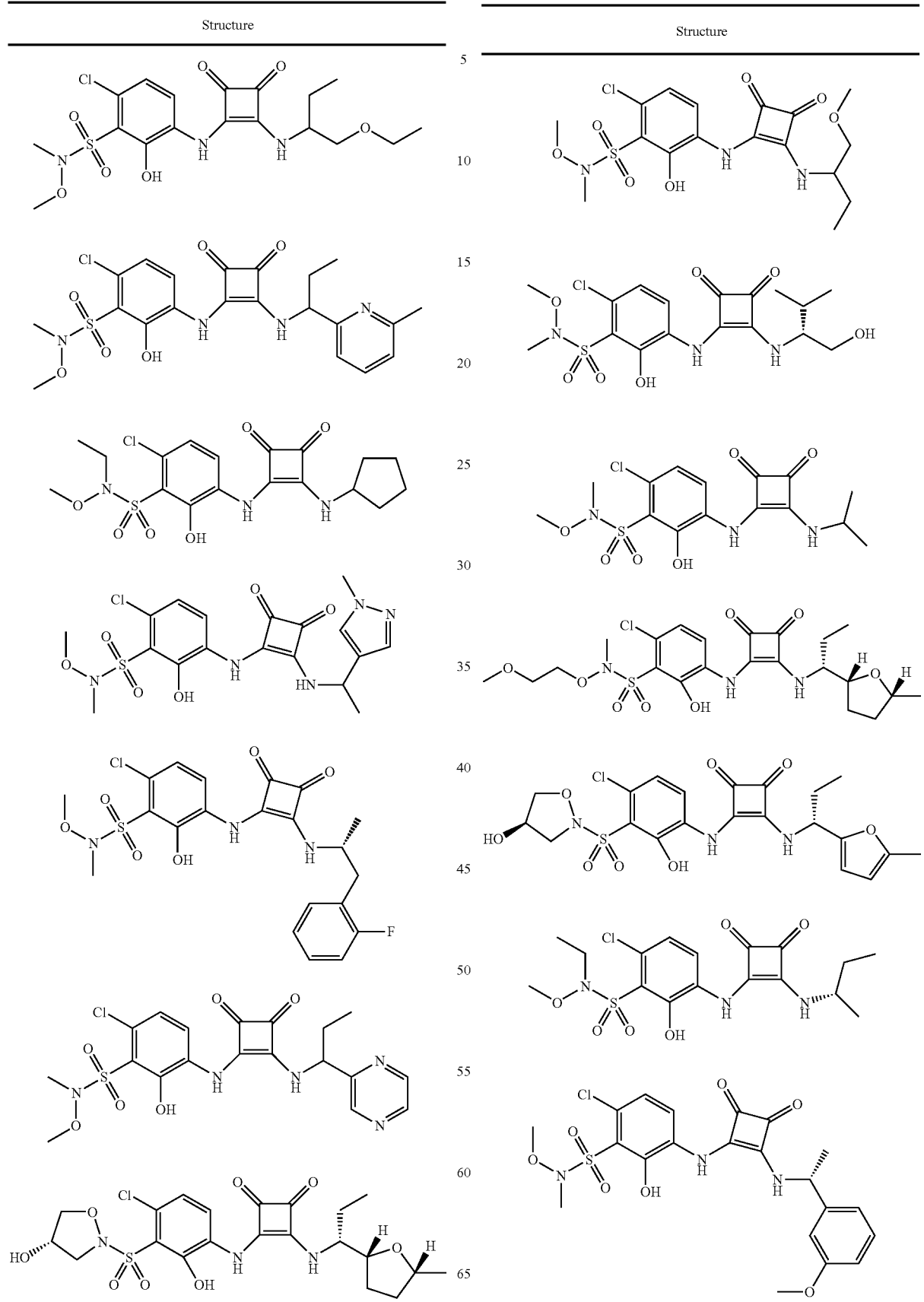

| 11 | 12 |
|---|---|
| -continued | -continued |
| Structure | Structure |
| 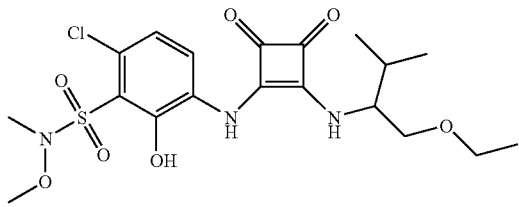 | 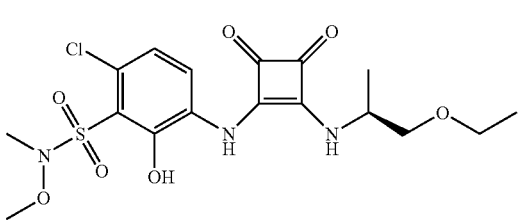 |
| 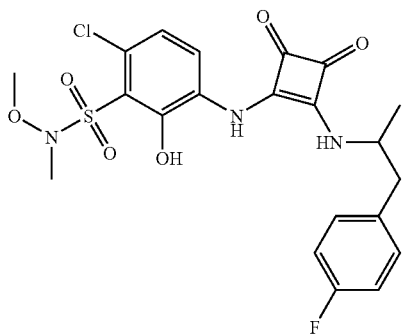 | 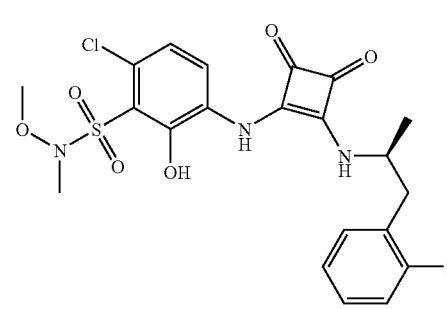 |
| 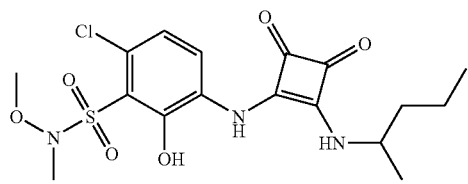 | 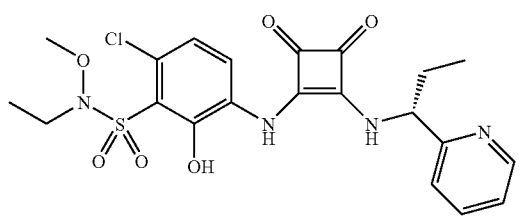 |
| 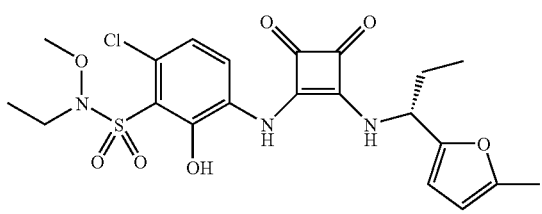 | 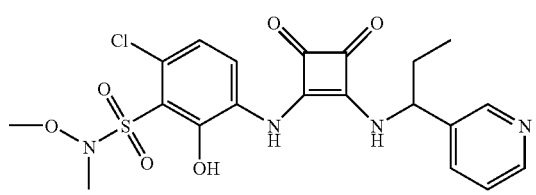 |
| 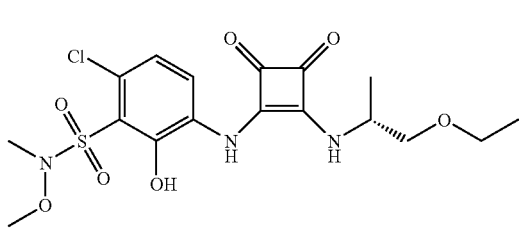 | 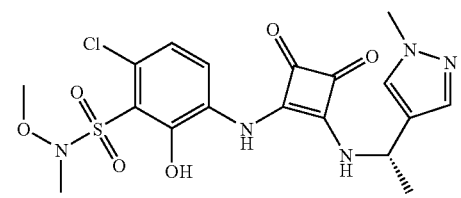 |
| 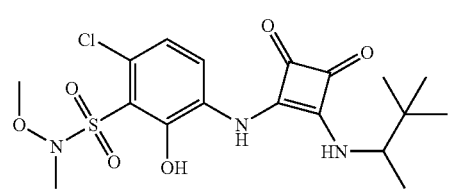 | 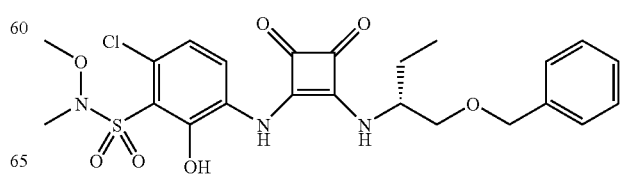 |
| 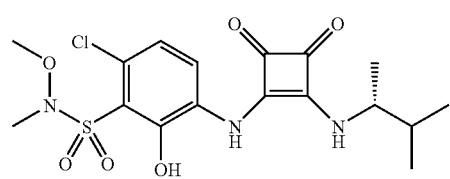 | |

| 13 -continued | 14 -continued |
|---|---|
| Structure | Structure |
| 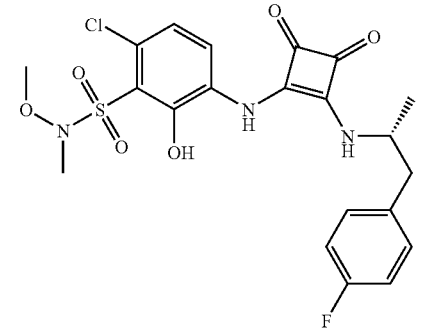 | 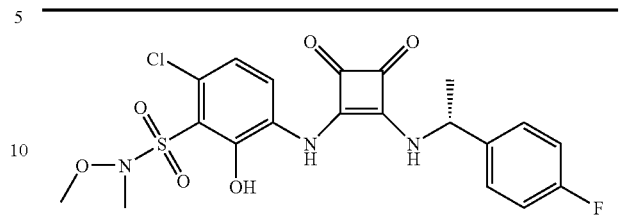 |
| 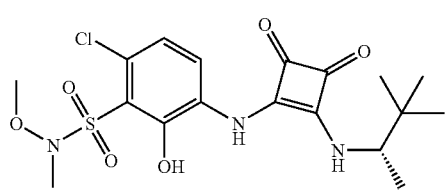 | 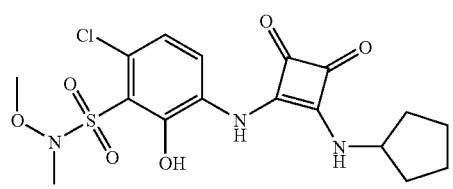 |
| 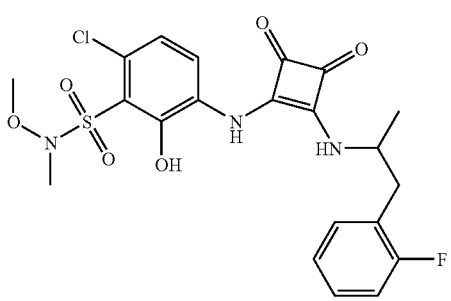 | 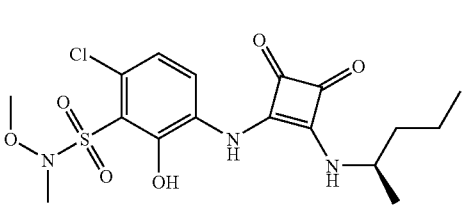 |
| 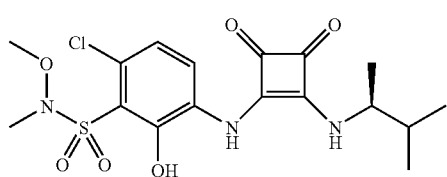 | 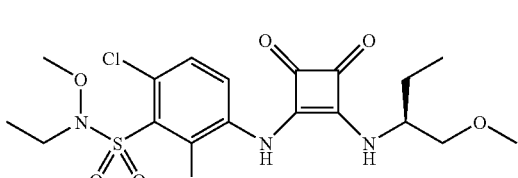 |
| 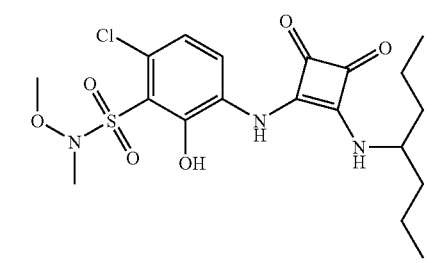 | 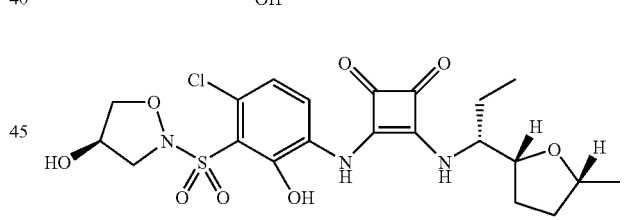 |
| 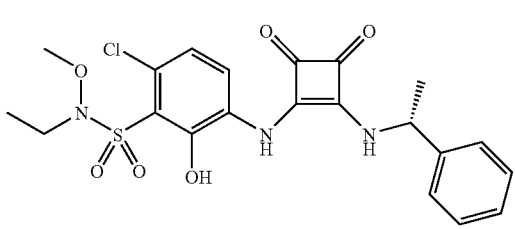 | 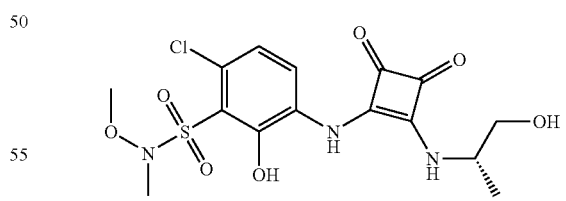 |
|  | 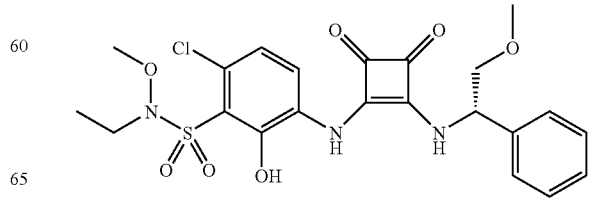 |

| 15 -continued | 16 -continued |
|---|---|
| Structure | Structure |
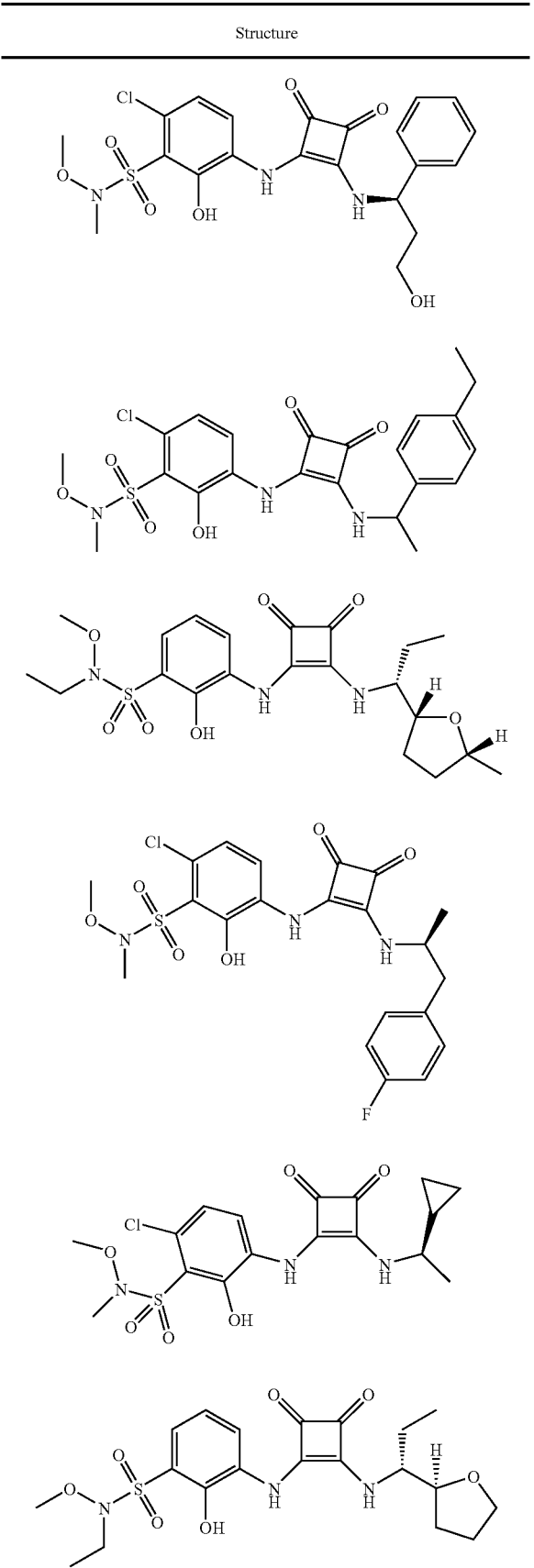
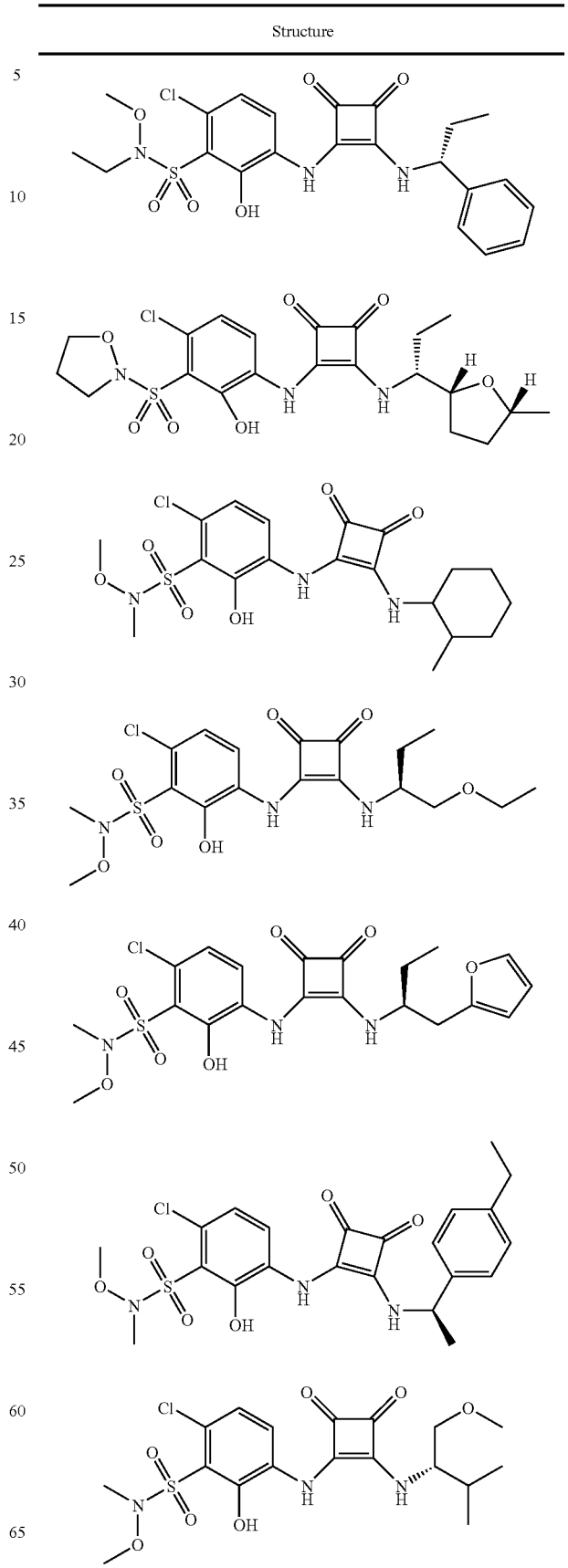

| 17 -continued | 18 -continued |
|---|---|
| Structure | Structure |
| 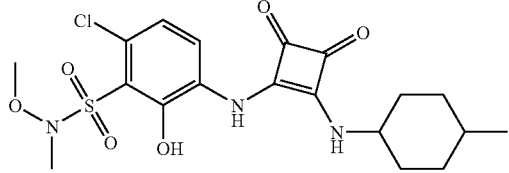 | 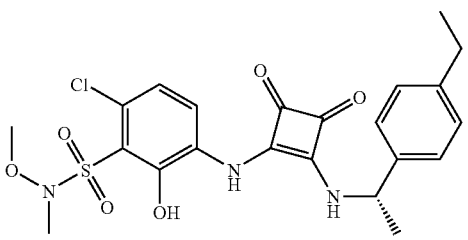 |
| 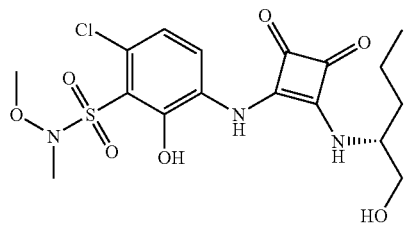 | 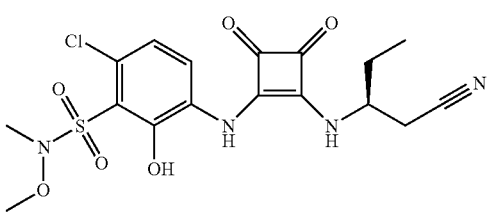 |
| 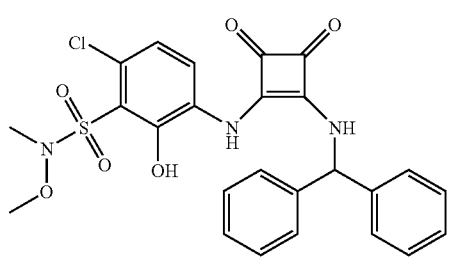 | 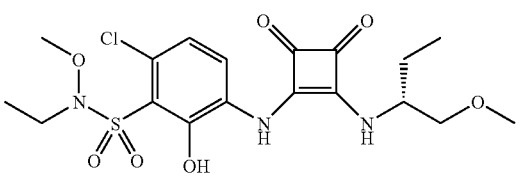 |
| 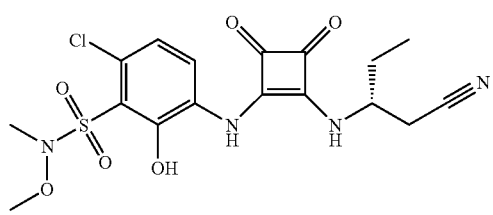 | 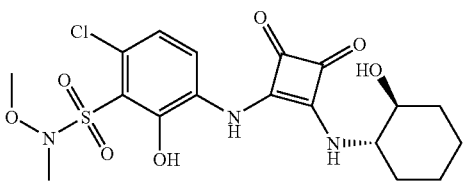 |
| 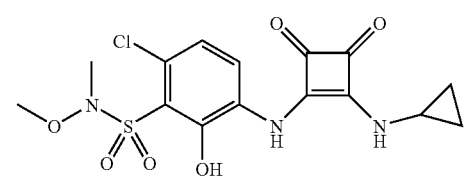 | 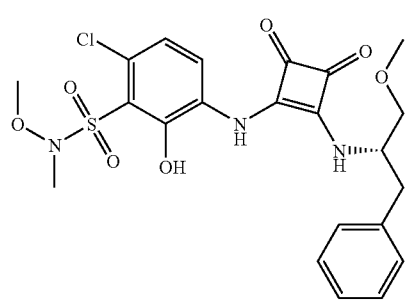 |
| 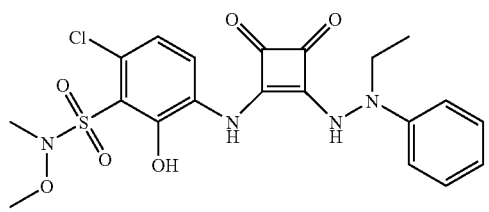 | 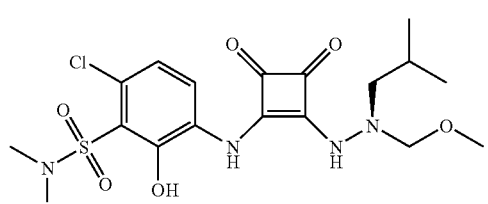 |
| 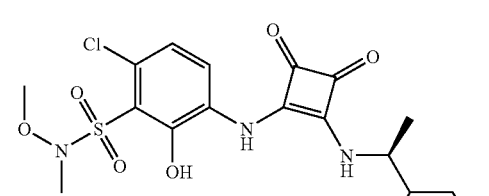 | 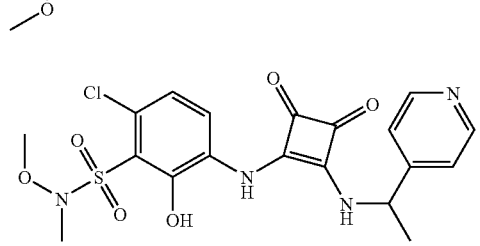 |
|  | |

-continued

| Structure |
|---|
| 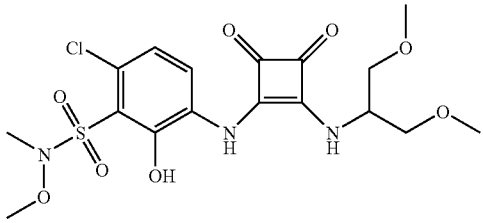 |
| 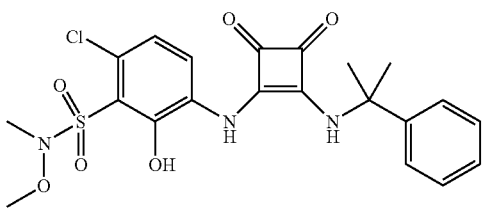 |
| 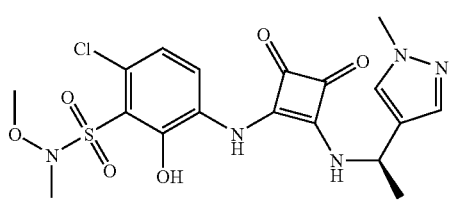 |
| 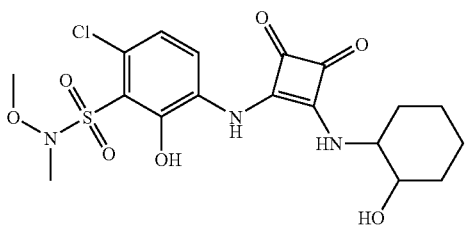 |
| 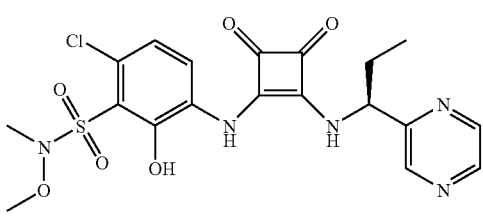 |

If not otherwise defined herein:

"Alkyl" includes linear or branched $C_1$-$C_8$ alkyl, such as $C_1$-$C_6$ alkyl or $C_1$-$C_4$ alkyl, e.g. $C_1$-$C_2$ alkyl, including unsubstituted or substituted alkyl, e.g. alkyl substituted by groups which are conventional in organic chemistry, e.g. halogen, OH, $NH_2$ or halo($C_{1-6}$)alkyl, "Halogen" includes fluoro, chloro, bromo, iodo, e.g. fluoro, chloro, bromo, suitably chloro, "Carbocyclic group" denotes a ring system consisting of the relevant number of carbon atoms, e.g. 3, 4, 5, 6, 7, 8, 9 or 10. The ring system may be a single ring, a fused ring system or a spirocyclic ring system. Furthermore, the carbocyclic group may be saturated, partially unsaturated or aromatic. In particular, it may include a saturated or partially unsaturated ring fused to an aromatic ring or a second saturated or partially unsaturated ring; or it may include two aromatic rings fused together. Thus, "carbocyclic group" includes, for example, cycloalkenyl, cycloalkyl, phenyl, indane, indene, naphthalene, tetralin and azulene.

"aryl" denotes an aromatic carbocyclic ring system containing 6 to 14 ring carbon atoms, which may be unsubstituted or substituted as defined.

"Heterocyclic group" denotes a ring system consisting of the relevant number of member atoms, e.g. 3, 4, 5, 6, 7, 8, 9 or 10, including at least one heteroatom selected from N, O and S. The ring system may be a single ring, a fused ring system or a spirocyclic ring system. Furthermore, the heterocyclic group may be saturated, partially unsaturated or aromatic (i.e. heterocyclic includes heterocycloalkyl, heterocycloalkenyl and heteroaryl). In particular, it may include a saturated or partially unsaturated ring fused to an aromatic ring or a second saturated or partially unsaturated ring; or it may include two aromatic rings fused together. In addition, the heterocyclic group includes a heterocyclic ring fused to a carbocyclic ring, e.g. benzofused heterocyclic groups. Suitably, the heterocyclic group includes 1, 2 or 3 heteroatoms selected from N, O and S.

"optionally substituted by one or more Z groups" denotes that the relevant group may include one or more substituents, each independently selected from the groups included within the definition of Z. Thus, where there are two or more Z group substituents, these may be the same or different.

"—($C_1$-$C_4$ alkylene)-" or "—($C_1$-$C_3$ alkylene)-" denote a hydrocarbon linking group having the relevant number of carbon atoms.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Compounds of formula (I) in free or pharmaceutically acceptable salt form are hereinafter referred to alternatively as compounds of the invention.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, choline, 4-(2-hydroxy-ethyl)morpholine, 1-(2-hydroxyethyl)pyrrolidine, N-methyl glutamine, piperazine, triethanol-amine or tromethamine. These salts may be prepared from compounds of formula I by known salt-forming procedures. Compounds of formula I that contain acidic, e.g. carboxyl, groups may also exist as zwitterions with the quaternary ammonium centre.

Pharmaceutically acceptable solvates in accordance with the invention include those wherein the solvent of crystallisation may be isotopically substituted e.g. $D_2O$, $d_6$-acetone or $d_6$-DMSO.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium ($^2H$) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Some of the compounds of Formula I may exist in different tautomeric forms. Tautomerism is well known to those skilled in the art and the skilled person will readily appreciate which groups are able to tautomerise to form the different tautomeric forms. The invention includes all tautomeric forms of the compounds of Formula I.

Any compound described herein as a compound of the present invention may be prepared according to or analogously to a conventional method or as specified herein. Starting materials are known or may be prepared according to or analogously to a conventional method or as specified herein.

A compound of formula I thus obtained may be converted into another compound of formula I, or a compound of formula I obtained in free form may be converted into a salt of a compound of formula I and vice versa.

In another aspect the present invention provides a process for the preparation of a compound of the present invention comprising:

reacting a compound of formula II

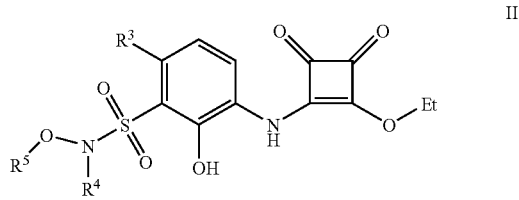

wherein $R^3$, $R^4$ and $R^5$ are as defined above, with a compound of formula III

wherein X, $R_1$ and $R_2$ are as defined above, under appropriate conditions, e.g. in the presence of triethylamine, acetonitrile, methanol, for an appropriate time, e.g. 2 to 24 hours, at appropriate temperatures, e.g. room temperature, to obtain a compound of formula (I) of the invention.

Compounds of the invention, are useful as pharmaceuticals. Accordingly the invention also provides a compound of formula I in free or pharmaceutically acceptable salt form for use as a pharmaceutical.

In another aspect the present invention provides the use of a compound of formula (I) wherein the substituents are as defined above as a pharmaceutical.

The compounds of the invention act as CXCR2 receptor antagonists, thereby inhibiting the infiltration and activation of inflammatory cells, in particular neutrophils, monocytes and CD8+ T cells and mediators involved in chronic obstructive pulmonary disease (COPD). The compounds of the invention therefore provide symptomatic relief and reduce disease progression.

The airways of subject with COPD exhibit an inflammatory response which is predominantly neutrophilic. When the airways are exposed to cigarette smoke macrophages, CD8+ T cells and epithelial cells are activated and release pro-inflammatory mediators, oxidants, cytokines and neutophilic chemotactic factors, IL-8, GROα, ENA-78 and leukotrienes. IL-8, GROα and ENA-78 are selective chemoattractants for neutrophils. In human neutrophils IL-8 binds two distinct receptors with similar affinity, CXCR1 and CXCR2. Closely related chemokines including GROα, β, γ, NAP-2 and ENA-78 bind only to CXCR2. Inhibiting neutrophil recruitment is therefore a recognised therapeutic strategy for treating several lung diseases. Blocking the binding of IL-8, GROα and ENA-78 to the chemokine receptor CXCR2 can provide beneficial effects in patients with COPD by suppressing the infiltration and activation of key inflammatory cells, thereby reducing subsequent tissue damage, mucus secretion, airflow obstruction and disease progression.

The IL-8 and GROα chemokine inhibitory properties of compounds of the invention can be demonstrated in the following assays:

Receptor Binding Assay

[$^{125}$I] IL-8 (human recombinant) are obtained from Amersham Pharmacia Biotech, with specific activity 2000 Ci/mmol. All other chemicals are of analytical grade. Human recombinant CXCR2 receptor expressed in Chinese hamster ovary cells (CHO-K1) is purchased from Euroscreen. The Chinese hamster ovary membranes are prepared according to protocol supplied by Euroscreen. Membrane protein concentration is determined using a Bio-Rad protein assay. Assays are performed in a 96-well micro plate format according the method described in White, et al., J Biol Chem., 1998, 273, 10095). Each reaction mixture contains 0.05 mg/ml CXCR2 membrane protein in 20 mM Bis-Tris-propane, pH 8.0, containing 1.2 mM $MgSO_4$, 0.1 mM EDTA, 25 mM NaCl and 0.03% CHAPS. In addition, compound of interest pre-dissolved in dimethylsulphoxide (DMSO) so as to reach a final concentration of between 10 μM and 0.0005 μM (final concentration of DMSO 2% (v/v)) is added. Binding is initiated by addition of 0.02 nM $^{125}$I-IL-8. After 2 hours at room temperature the plate is harvested using a Brandell™ 96-well harvester onto glass fibre filter plate (GF/c) blocked with 1% polyethyleneimine+0.5% BSA and washed 3 times with 25 mM NaCl, 10 mM TrisHCl, 1 mM $MgSO_4$, 0.5 mM EDTA, 0.03% CHAPS, pH 7.4. The filter is dried at 50° C. overnight. Backseal is applied to the plate and 50 μl of liquid scintillation fluid added. The counts are measured on the Packard Topcount™ scintillation counter.

[$^{35}$S]-GTPγS Binding Assay for Human CXCR2 Receptor Using SPA Technology

[$^{35}$S]-GTPγS (with specific activity 1082 Ci/mmol) and wheat germ agglutinin poly vinyl toluene scintillation proximity beads are purchased from Amersham Pharmacia Biotech. The Chinese hamster ovary cell (CHO-K1) membranes expressing human CXCR2 receptors are purchased from Biosignal Packard Inc. All other chemicals are of analytical grade. White non-binding surface 96 well Optiplate™ microplates are obtained from Packard. Recombinant human IL-8 is synthesised, cloned and expressed in *Escherichia coli* as described previously (Lindley I, et al., Proc. Natl. Acad. Sci., 1988, 85(23):9199).

The assay is performed in duplicate in 96 well Optiplate™ microplate in a final volume of 250 μl per well. Compounds are diluted in DMSO (0.5% final concentration) and incubated in 20 mM HEPES buffer pH 7.4 containing 10 mM $MgCl_2$, 100 mM NaCl, 1 mM EDTA plus 100 nM IL-8, 50 μM GDP and 500 pM [$^{35}$S]GTPγS per well. SPA beads (1 mg/well final concentration) were pre-mixed with the membranes (10 μg/well final concentration) in assay buffer: 20 mM HEPES buffer pH 7.4 containing 10 mM $MgCl_2$, 100 mM NaCl, 1 mM EDTA. The bead membrane mixture is added to each well, plates are sealed and incubated at room temperature for 60 minutes. The plate is centrifuged and read on Packard TopCount™ scintillation counter, program [$^{35}$S dpm] for 1 min/well. Data are expressed as the % response to 100 nM IL-8 minus basal.

Chemotaxis Assay

The in vitro inhibitory properties of these compounds are determined in the neutrophil chemotaxis assay. Assays are performed in a 96-well plate format according to previously published method (Frevert C W, et al., J Immunolog. Methods, 1998, 213, 41). 96-well chemotaxis chambers 5 μm are obtained from Neuro Probe, all cell buffers are obtained from Invitrogen Paisley, UK, dextran—T500 and Ficoll-Paque Plus™ density gradient centrifugation media are purchased from Pharmacia Biotech Buckinghamshire, UK. Calcein-AM dye is obtained from Molecular Probes. Neutrophils are isolated as previously described (Haslett, C., et al. Am J Path., 1985, 119:101). Citrated whole blood is mixed with 4% (w/v) dextran-T500 and allowed to stand on ice for 30 minutes to remove erythrocytes. Granulocytes (PMN) are separated from peripheral blood mononuclear cells by layering 15 ml of cell suspension onto 15 ml Ficoll-Paque PLUS density gradient and centrifuged at 250×g for 25 minutes. Following centrifugation any erythrocytes contamination of PMN pellet is removed by hypotonic shock lysis using 10 ml ice-cold endotoxin-free sterile water for 50 seconds and neutralised with 10 ml of cold 2× phosphate buffered saline. Isolated neutrophils ($1 \times 10^7$) are labelled with the fluorochrome calcein-AM (5 μg) in a total volume of 1 ml and incubated for 30 minutes at 37° C. The labelled cells are washed with RPMI without phenol red+0.1% bovine serum albumin, prior to use the cells are counted and adjusted to a final concentration of $5 \times 10^6$ cells/ml. The labelled neutrophils are then mixed with test compounds (0.001-1000 nM) diluted in DMSO (0.1% final concentration) and incubated for 10 minutes at room temperature. The chemoattractants (29 μl) are placed in the bottom chamber of a 96-well chemotaxis chamber at a concentration between (0.1-5 nM). The polycarbonate filter (5 μm) is overlaid on the plate, and the cells (25 μl) are loaded on the top filter. The cells are allowed to migrate for 90 minutes at 37° C. in a humidified incubator with 5% $CO_2$. At the end of the incubation period, migrated cells are quantified using a multi-well fluorescent plate reader (Fluroskan II™, Labsystems) at 485 nm excitation and 538 nm emission. Each compound is tested in quadruplet using 4 different donors. Positive control cells, i.e. cells that have not been treated with compound, are added to the bottom well. These represent the maximum chemotactic response of the cells. Negative control cells, i.e. those that have not been stimulated by a chemoattractant, are added to the bottom chamber. The difference between the positive control and negative control represents the chemotactic activity of the cells.

The compounds of the Examples herein below have $IC_{50}$ values below 10 μM in the [$^{35}$S]-GPTγS binding assay. For instance, the compounds of the Examples shown in the below table have the $IC_{50}$ values stated.

| Example | IC$_{50}$ (µM) |
|---|---|
| 2 | 0.002 |
| 3 | 0.026 |
| 4 | 0.013 |
| 5 | 0.033 |
| 6 | 0.028 |
| 7 | 0.004 |
| 8 | 0.005 |
| 2.13 | 0.006 |
| 2.17 | 0.008 |
| 2.19 | 0.009 |
| 2.23 | 0.021 |
| 2.27 | 0.234 |
| 2.32 | 0.011 |
| 2.35 | 0.014 |
| 2.43 | 0.017 |
| 2.47 | 0.019 |
| 2.50 | 0.093 |
| 2.57 | 0.026 |
| 2.58 | 0.028 |
| 2.60 | 0.030 |
| 2.71 | 0.056 |
| 2.95 | 0.283 |

Having regard to their inhibition of binding of CXCR2, compounds of the invention are useful in the treatment of conditions or diseases mediated by CXCR2, for example inflammatory or allergic conditions or diseases, particularly chronic obstructive pulmonary airways or lung disease (COPD, COAD or COLD), including chronic bronchitis or dyspnea associated therewith, emphysema, bronchiolitis obliterans syndrome and severe asthma.

Compounds of the present invention are further useful in the treatment of various diseases, such as cancer, e.g. ovarian cancer, prostate cancer, melanoma including metastatic melanoma, lung cancer, e.g. non small cell lung cancer, renal cell carcinoma; tumour angiogenesis, ischaemia/reperfusion injury, delayed graft function, osteoarthritis, myeloid metaplasia with myelofibrosis, Adenomyosis, contact hypersensitivity (skin). and in wound healing. Treatment in accordance with the invention may be symptomatic or prophylactic.

Prophylactic efficacy in the treatment of chronic bronchitis or COPD will be evidenced by reduced frequency or severity, will provide symptomatic relief and reduce disease progression, improvement in lung function. It may further be evidenced by reduced requirement for other, symptomatic therapy, i.e. therapy for or intended to restrict or abort symptomatic attack when it occurs, for example anti-inflammatory (e.g. corticosteroid) or bronchodilatory.

Other inflammatory or obstructive airways diseases and conditions to which the invention is applicable include acute lung injury (ALI), acute/adult respiratory distress syndrome (ARDS), idiopathic pulmonary fibrosis, fibroid lung, airway hyperresponsiveness, dyspnea, pulmonary fibrosis, allergic airway inflammation, small airway disease, lung carcinoma, acute chest syndrome in patients with sickle cell disease and pulmonary hypertension, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Compounds of the invention are also useful for treating respiratory viral infections, which exacerbate underlying chronic conditions such as asthma, chronic bronchitis, COPD, otitis media, and sinusitis. The respiratory viral infection treated may be associated with secondary bacterial infection, such as otitis media, sinusitis or pneumonia.

Compounds of the invention are also useful in the treatment of inflammatory conditions of the skin, for example psoriasis, atopic dermatitis, lupus erythematosus, and other inflammatory or allergic conditions of the skin.

Compounds of the invention may also be used for the treatment of other diseases or conditions, in particular diseases or conditions having an inflammatory component, for example, diseases affecting the nose including allergic rhinitis, e.g. atrophic, chronic, or seasonal rhinitis, inflammatory conditions of the gastrointestinal tract, for example inflammatory bowel disease such as ulcerative colitis and Crohn's disease, diseases of the bone and joints including rheumatoid arthritis, psoriatic arthritis, and other diseases such as atherosclerosis, multiple sclerosis, and acute and chronic allograft rejection, e.g. following transplantation of heart, kidney, liver, lung or bone marrow.

Compounds of the invention are also useful in the treatment of endotoxic shock, glomerulonephritis, cerebral and cardiac ischemia, Alzheimer's disease, cystic fibrosis, virus infections and the exacerbations associated with them, acquired immune deficiency syndrome (AIDS), multiple sclerosis (MS), *Helicobacter pylori* associated gastritis, and cancers, particularly the growth of ovarian cancer.

Compounds of the invention are also useful for treating symptoms caused by viral infection in a human which is caused by the human rhinovirus, other enterovirus, coronavirus, herpes viruses, influenza virus, parainfluenza virus, respiratory syncytial virus or an adenovirus. Compounds of the invention are also useful for treating pancreatitis.

The effectiveness of a compound of the invention in inhibiting inflammatory conditions, for example in inflammatory airways diseases, may be demonstrated in an animal model, e.g. mouse, rat or rabbit model, of airway inflammation or other inflammatory conditions, for example as described by Wada et al, *J. Exp. Med* (1994) 180:1135-40; Sekido et al, *Nature* (1993) 365:654-57; Modelska et al., *Am. J. Respir Crit Care Med* (1999) 160:1450-56; and Laffon et al (1999) *Am. J. Respir Crit Care Med.* 160:1443-49.

The compounds of the invention are also useful as co-therapeutic compounds for use in combination with other drug substances such as anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID (™) CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422, WO 04/05285, WO2004096800, WO2006048225 and WO2008025541; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially a compound of formula

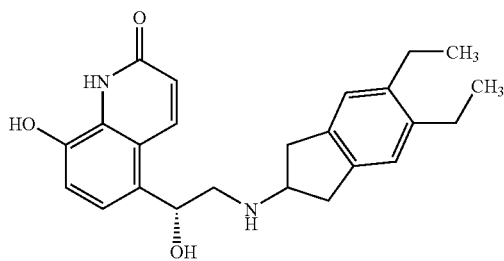

and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 and WO 04/80964.

Such antihistamine drug substances include cetirizine hydrochloride, acetaminophen, clemastine fumarate, promethazine, loratidine, desloratidine, diphenhydramine and fexofenadine hydrochloride.

Combinations of compounds of the invention and anticholinergic or antimuscarinic compounds, steroids, beta-2 agonists, PDE4 inhibitors, dopamine receptor agonists, LTD4 antagonists or LTB4 antagonists may also be used. Other useful combinations of compounds of the invention with anti-inflammatory drugs are those with other antagonists of chemokine receptors, e.g. CCR-1, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]-tetrahydro-N,N-dimethyl-2H-pyran-4-aminium chloride (TAK-770), CCR-5 antagonists described in U.S. Pat. No. 6,166,037 (particularly claims 18 and 19), WO 0066558 (particularly claim 8), and WO 0066559 (particularly claim 9).

In accordance with the foregoing, the invention also provides a method for the treatment of a condition or disease mediated by CXCR2, for example an inflammatory or allergic condition, particularly an inflammatory or obstructive airways disease, which comprises administering to a subject, particularly a human subject, in need thereof an effective amount of a compound of formula I in a free or pharmaceutically acceptable salt form as hereinbefore described. In another aspect the invention provides the use of a compound of formula I, in free or pharmaceutically acceptable salt form, as hereinbefore described for the manufacture of a medicament for the treatment of a condition or disease mediated by CXCR2, for example an inflammatory or allergic condition or disease, particularly an inflammatory or obstructive airways disease.

The compounds of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

In a further aspect, the invention also provides a pharmaceutical composition comprising as active ingredient a compound of formula I in free or pharmaceutically acceptable salt form, optionally together with a pharmaceutically acceptable diluent or carrier therefor. The composition may contain a co-therapeutic compound such as an anti-inflammatory bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture, e.g. magnesium stearate. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) a compound of the invention in inhalable form, e.g. in an aerosol or other atomisable composition or in inhalable particulate, e.g. micronised form, (B) an inhalable medicament comprising a compound of the invention in inhalable form; (C) a pharmaceutical product comprising such a compound of the invention in inhalable form in association with an inhalation device; and (D) an inhalation device containing a compound of the invention in inhalable form.

Dosages of compounds of the invention employed in practising the present invention will of course vary depending, for example, on the particular condition to be treated, the effect desired and the mode of administration. In general, suitable daily dosages for administration by inhalation are of the order of 0.01 to 1 mg/kg per day while for oral administration suitable daily doses are of the order of 0.005 to 100 mg/kg of total body weight. The daily parenteral dosage regimen is about 0.001 to about 80 mg/kg of total body weight. The daily topical dosage regimen will preferably be from 0.1 mg to 150 mg, administered one to four, preferably two or three times daily.

The invention is illustrated by the following Examples.

EXAMPLES

Example compounds of the present invention include compounds of formula I are shown in Table 1 below, the method of preparation being described hereinafter.

TABLE 1

| Ex. | Structure | Name | $[M + H]^+$ |
|---|---|---|---|
| 1 | 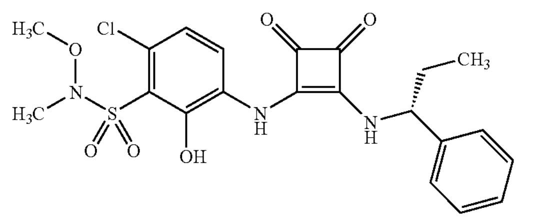 | 6-Chloro-3-[3,4-dioxo-2-((R)-1-phenyl-propylamino)-cyclobut-1-enylamino]-2-hydroxy-N-methoxy-N-methyl-benzenesulfonamide | 480 |
| 2 | 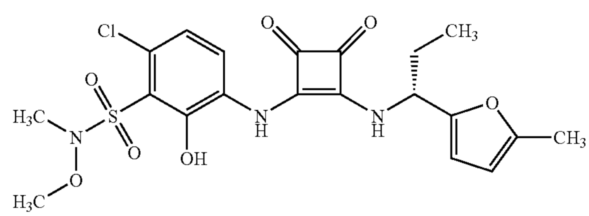 | 6-Chloro-2-hydroxy-N-methoxy-N-methyl-3-{2-[(R)-1-(5-methyl-furan-2-yl)-propylamino]-3,4-dioxo-cyclobut-1-enyl amino}-benzenesulfonamide | 484 |
| 3 | 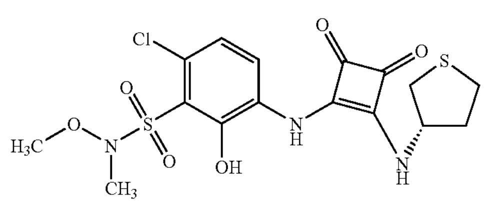 | 6-Chloro-3-{3,4-dioxo-2-[(S)-(tetrahydro-thiophen-3-yl)amino]-cyclobut-1-enylamino}-2-hydroxy-N-methoxy-N-methyl-benzenesulfonamide | 448 |
| 4 | 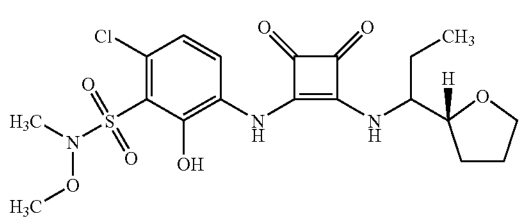 | 6-Chloro-3-{3,4-dioxo-2-[(R)-1-(tetrahydro-furan-2-yl)-propylamino]-cyclobut-1-enylamino}-2-hydroxy-N-methoxy-N-methyl-benzenesulfonamide | 474 |

TABLE 1-continued

| Ex. | Structure | Name | [M + H]⁺ |
|---|---|---|---|
| 5 | 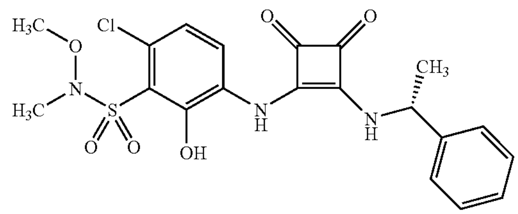 | 6-Chloro-3-[3,4-dioxo-2-((R)-1-phenyl-ethylamino)-cyclobut-1-enylamino]-2-hydroxy-N-methoxy-N-methyl-benzenesulfonamide | 466 |
| 6 | 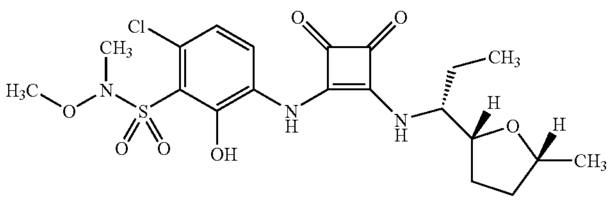 | 6-Chloro-2-hydroxy-N-methoxy-N-methyl-3-{2-[(R)-1-((2R, 5R)-5-methyl-tetrahydro-furan-2-yl)-propylamino]-3,4-dioxo-cyclobut-1-enylamino}-benzene sulfonamie | 488 |
| 6a | 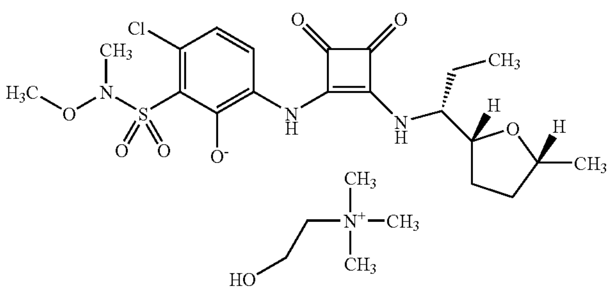 | 3-Chloro-2-(methoxy-methyl-sulfamoyl)-6-{2-[(R)-1-((2R, 5R)-5-methyl-tetrahydro-furan-2-yl)-propylamino]-3,4-dioxo-cyclobut-1-enylamino}-phenolate (2-hydroxy-ethyl)-trimethyl-ammonium; | 488 |
| 7 | 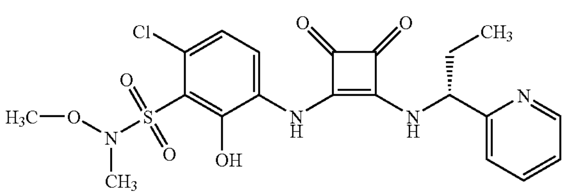 | 6-Chloro-3-[3,4-dioxo-2-((R)-1-pyridin-2-yl-propylamino)-cyclobut-1-enylamino]-2-hydroxy-N-methoxy-N-methyl-benzenesulfonamide | 481 |
| 8 | 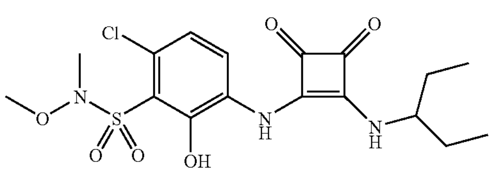 | 6-Chloro-3-[2-(1-ethyl-propylamino)-3,4-dioxo-cyclobut-1-enylamino]-2-hydroxy-N-methoxy-N-methyl-benzenesulfonamide | 432 |
| 9 | 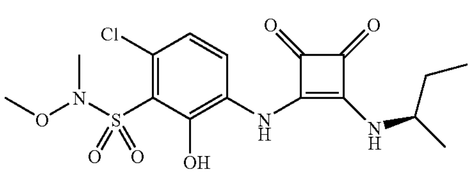 | 3-[2-((R)-sec-Butylamino)-3,4-dioxo-cyclobut-1-enylamino]-6-chloro-2-hydroxy-N-methoxy-N-methyl-benzenesulfonamide | 418 |
| 10 | 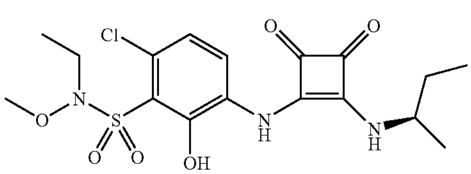 | 3-[2-((R)-sec-Butylamino)-3,4-dioxo-cyclobut-1-enylamino]-6-chloro-N-ethyl-2-hydroxy-N-methoxy-benzenesulfonamide | 432 |

TABLE 1-continued

| Ex. | Structure | Name | [M + H]+ |
|---|---|---|---|
| 11 | 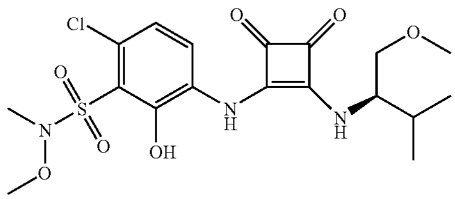 | 6-Chloro-2-hydroxy-N-methoxy-3-[2-((R)-1-methoxymethyl-2-methyl-propylamino)-3,4-dioxo-cyclobut-1-enylamino]-N-methyl-benzenesulfonamide | 462 |
| 12 | 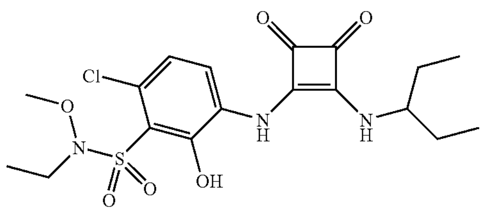 | 6-Chloro-N-ethyl-3-[2-(1-ethyl-propylamino)-3,4-dioxo-cyclobut-1-enylamino]-2-hydroxy-N-methoxy-benzenesulfonamide | 446 |
| 13 | 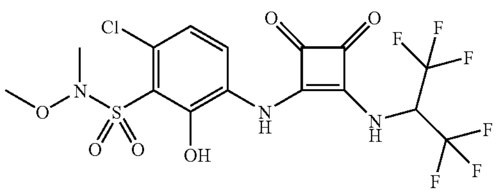 | 6-chloro-3-(2-(1,1,1,3,3,3-hexafluoropropan-2-ylamino)-3,4-dioxocyclobut-1-enylamino)-2-hydroxy-N-methoxy-N-methylbenzenesulfonamide | 512 |

Referring to the Examples in Table 1 and Table 2, the compounds were synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra were run on LCMS systems using electrospray ionization. [M+H]+ refers to mono-isotopic molecular weights. If not indicated otherwise, the analytical conditions were as follows:

| Method A | |
|---|---|
| Instrument | Waters Acquity |
| Column | Waters BEH C18 100 × 2.1 mm, 1.7 m |
| Column Temperature | 50° C. |
| Eluents | A: H2O, B: acetonitrile, both containing 0.1% TFA |
| Flow Rate | 0.7 mL/min |
| Gradient | 0.25 min 5% B; 5% to 95% B in 1.00 min, 0.25 min 95% B |

| Method B | |
|---|---|
| Instrument | Waters Acquity |
| Column | Waters BEH C18 100 × 2.1 mm, 1.7 m |
| Column Temperature | 50° C. |
| Eluents | A: H2O, B: acetonitrile, both containing 0.1% TFA |
| Flow Rate | 0.7 mL/min |
| Gradient | 0.25 min 30% B; 30% to 95% B in 1.00 min, 0.25 min 95% B |

| Method C | |
|---|---|
| Instrument | Waters Acquity |
| Column | Waters BEH C18 100 × 2.1 mm, 1.7 m |
| Column Temperature | 50° C. |
| Eluents | A: H2O, B: acetonitrile, both containing 0.1% TFA |
| Flow Rate | 0.7 mL/min |
| Gradient | 0.25 min 5% B; 5% to 95% B in 7.75 min, 1.00 min 95% B |

NMR spectra were run on open access Bruker AVANCE 400 NMR spectrometers using ICON-NMR. Spectra were measured at 298K and were referenced using the solvent peak.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials were obtained from commercial suppliers and used without further purification. Salts may be prepared from compounds by known salt-forming procedures.

In addition various trade reagents and materials available from have been utilized. Such reagents and materials can be readily obtained from the suppliers indicated.

For the examples below as well as throughout the application, the following abbreviations have the following meanings. If not defined, the terms have their generally accepted meanings.

Abbreviations:
RT room temperature
DMF N,N-dimethylformamide
DIPEA N,N-diisopropylethylamine
NMP N-methylpyrrolidine
THF tetrahydrofuran
MeOH methanol
DCM dichloromethane
EtOAc ethyl acetate
EtOH ethanol
LCMS liquid chromatographic mass spectroscopy
TEA triethylamine
TFA trifluoroacetic acid
HPLC high performance liquid chromatography
CDI carbonyl diimidazole
IPA isopropyl alcohol Preparation of Final Compounds Example 1

6-Chloro-3-[3,4-dioxo-2-((R)-1-phenyl-propylamino)-cyclobut-1-enylamino]-2-hydroxy-N-methoxy-N-methyl-benzenesulfonamide To a stirred suspension of 6-chloro-3-(2-ethoxy-3,4-dioxo-cyclobut-1-enylamino)-2-hydroxy-N-methoxy-N-methyl-benzenesulfonamide (Intermediate A) (100 mg, 0.256 mmol) in MeCN (2 ml) and EtOH (1 ml) under $N_2$ at RT was added (R)-(+)-alpha-ethylbenzylamine (58.8 mg, 0.435 mmol) and triethylamine (0.142 ml, 1.02 mmol) and the reaction mixture was heated at 80° C. overnight. The reaction mixture was concentrated in vacuo to give a yellow solid which was loaded onto a 1 g pre-packed silica column, dissolving in the minimal amount of 5% MeOH in DCM. Purification was carried out eluting with 10-40% EtOAc in iso-hexane and the appropriate fractions were concentrated under vacuum to give a yellow glassy solid. The solid was dissolved in EtOAc and washed four times with 1M HCl (aq). The organic portion was dried (sodium sulfate) and concentrated in vacuo to yield a brown gummy solid. Trituration with iso-hexane afford the title compound as a solid brown solid; $[M+H]^+$ 180. $^1H$ NMR (DMSO) 0.9 (3H, t, CH3), 1.9 (2H, m, CH2), 3.0 (3H, s, CH3), 3.6 (3H, s, CH3), 5.1 (1H, m, CH), 7.2-7.5 (6H, m, Ar—H), 8.0 (1H, d, Ar—H).

Examples 2 and 3

These examples namely, 6-Chloro-2-hydroxy-N-methoxy-N-methyl-3-{2-[(R)-1-(5-methyl-furan-2-yl)-propylamino]-3,4-dioxo-cyclobut-1-enylamino}-benzenesulfonamide; $[M+H]^+$ 484 Retention Time 5.1 mins (Method C) (Ex.2) and 6-Chloro-3-{3,4-dioxo-2-[(S)-(tetrahydrothiophen-3-yl)amino]-cyclobut-1-enylamino}-2-hydroxy-N-methoxy-N-methyl-benzenesulfonamide; $[M+H]^+$ 448 Retention Time 1.44 mins (Method A) (Ex.3), are prepared analogously to Example 1 by replacing (R)-(+)-alpha-ethylbenzylamine with the appropriate amine.

Example 4

6-Chloro-3-{3,4-dioxo-2-[(R)-1-(tetrahydro-furan-2-yl)-propylamino]-cyclobut-1-enylamino}-2-hydroxy-N-methoxy-N-methyl-benzenesulfonamide To a stirred solution of 6-chloro-3-(2-ethoxy-3,4-dioxocyclobut-1-enylamino)-2-hydroxy-N-methoxy-N-methylbenzenesulfonamide (Intermediate A) (500 mg, 1.279 mmol) in MeCN was added TEA (1.783 ml, 12.79 mmol) and (R)-1-(tetrahydro-furan-2-yl)-propylamine (1 g, 7.74 mmol) (Intermediate DA). The reaction mixture was heated to 70° C. over night. The reaction mixture was evaporated to dryness. The residue was dissolved in DCM and washed with 0.1M aqueous HCl. The organic layer was dried over $MgSO_4$, filtered and evaporated to dryness. The diastereomers were separated by Supercritical fluid chromatography according to the following conditions:

Mobile Phase: 30% 2-Propanol/0.1% DEA/70% $CO_2$
Column: Chiralpak AD-H, 250×10 mm id, 5 μm
Detection: UV @ 220 nm
Flow rate: 10 ml/min
Sample concentration: 227 mg in 4.5 ml EtOH
Injection volume: 150 μl The separated diastereomers were each dissolved in DCM and washed with saturated aqueous ammonium chloride. The organic layers were dried over magnesium sulfate, filtered and evaporated to dryness to give Diastereomer 1
SFC Retention time: 3.02 min
$(M+H)^+=474.0$
1H NMR (CD3OD) 1.02 (3H, t, CH3), 1.70 (2H, m, CH2), 1.75 (1H, m, CH), 1.95 (2H, m, CH2), 2.08 (1H, m, CH), 3.09 (3H, s, CH3), 3.68 (3H, s, CH3), 3.78 (1H, dd, CH), 3.90 (1H, dd, CH), 3.95 (1H, m, CH), 4.15 (1H, m, CH), 7.20 (1H, d, CH), 8.29 (1H, d, CH)

Diastereomer 2
Retention time: 4.20 min
$(M+H)^+=474.0$
1H NMR (CD3OD) 1.02 (3H, t, CH3), 1.51 (1H, m, CH), 1.75 (1H, m, CH), 1.95 (4H, m, 2×CH2), 3.09 (3H, s, CH3), 3.68 (3H, s, CH3), 3.78 (1H, dd, CH), 3.85 (1H, dd, CH), 3.95 (1H, dd, CH), 4.20 (1H, m, CH), 7.20 (1H, d, CH), 8.29 (1H, d, CH).

Example 5

6-Chloro-3-[3,4-dioxo-2-((R)-1-phenyl-ethylamino)-cyclobut-1-enylamino]-2-hydroxy-N-methoxy-N-methyl-benzenesulfonamide This compound was prepared analogously to Example 1 by replacing (R)-(+)-alpha-ethylbenzylamine with the appropriate amine; $[M+H]^+$ 466 Retention Time 5.38 mins (Method C).

Example 6

6-Chloro-2-hydroxy-N-methoxy-N-methyl-3-{2-[(R)-1-((2R,5R)-5-methyl-tetrahydro-furan-2-yl)-propylamino]-3,4-dioxo-cyclobut-1-enylamino}-benzene sulfonamide To a stirred suspension of 6-chloro-3-(2-ethoxy-3,4-dioxo-cyclobut-1-enylamino)-2-hydroxy-N-methoxy-N-methyl-benzenesulfonamide (Intermediate A) (7 g, 17.91 mmol) in MeCN (2 ml) and EtOH (1 ml) under $N_2$ at RT was added ((R)-1-((2R,5R)-5-methyl-tetrahydro-furan-2-yl)-propylamine para-toluenesulfonate salt (Intermediate E) (5.67 g, 17.91 mmol) and TEA (0.999 ml, 7.16 mmol) and the reaction mixture was heated at 50° C. for 16 hours. Further TEA was added (2.48 ml, 17.91 mmol) and the reaction was heated at 50° C. for 1 hour then 60° C. for 20 hours. Further TEA (2.48 ml, 17.91 mmol) and Intermediate E (1.13 g, 3.58 mmol) was added and the reaction was heated at 60° C. for 17.5 hours.

The reaction mixture was concentrated in vacuo and partitioned between EtOAc and 1M HCl (aq). The aqueous layer was adjusted to pH 5 using 2M NaOH (aq) and extracted using EtOAc. The EtOAc layers were combined and washed with saturated sodium bicarbonate (aq), water and brine. The organic layer was dried (MgSO$_4$) and concentrated in vacuo. The resulting residue was recrystallised from toluene to give a light brown solid; [M+H]$^+$ 488.2. $^1$H NMR (DMSO) 0.9 (3H, t, CH3), 1.2 (3H, d, CH3), 1.3 (1H, m) 1.6 (3H, m) 1.9 (2H, m) 3.6 (3H, s, CH3), 3.6 (3H, s, CH3), 3.9 (2H, m) 4.0 (1H, m), 7.2 (1H, d), 8.1 (1H, d), 8.2 (1H, d), 9.5 (1H, s), 10.1 (1H, s).

Example 6a

3-Chloro-2-(methoxy-methyl-sulfamoyl)-6-{2-[(R)-1-((2R,5R)-5-methyl-tetrahydro-furan-2-yl)-propylamino]-3,4-dioxo-cyclobut-1-enylamino}-phenolate (2-hydroxy-ethyl)-trimethyl-ammonium To a stirred solution of 6-Chloro-2-hydroxy-N-methoxy-N-methyl-3-{2-[(R)-1-((2R,5R)-5-methyl-tetrahydro-furan-2-yl)-propylamino]-3,4-dioxo-cyclobut-1-enylamino}-benzene sulfonamide (2.1 g, 4.3 mmol) in EtOAc (30 ml) and IPA (5 ml) at reflux was added a solution of 45% choline hydroxide in MeOH (1.213 ml, 4.3 mmol). After 20 minutes reaction mixture was cooled to room temperature and stirring continued for 1 hour. The crystalline yellow solid was collected by filtration; [M+H]$^+$ 488.2 $^1$H NMR (DMSO) 0.9 (3H, t, CH3), 1.2 (3H, d, CH3), 1.3 (1H, m) 1.5 (1H, m), 1.6 (2H, m), 1.9 (2H, m) 3.0 (3H, s), 3.1 (9H, s), 3.4 (2H, t), 3.6 (3H, s, CH3), 3.9 (4H, m), 4.0 (1H, m), 5.3 (1H, t), 5.9 (1H, d), 7.7 (1H, d), 8.5 (1H, d), 9.6 (1H, s).

Example 7

6-Chloro-3-[3,4-dioxo-2-((R)-1-pyridin-2-yl-propylamino)-cyclobut-1-enylamino]-2-hydroxy-N-methoxy-N-methyl-benzenesulfonamide This compound was prepared analogously to Example 1 by replacing (R)-(+)-alpha-ethylbenzylamine with the appropriate amine; [M+H]$^+$ 481 Retention Time 1.06 mins (Method B).

Example 8

6-Chloro-3-[2-(1-ethyl-propylamino)-3,4-dioxo-cyclobut-1-enylamino]-2-hydroxy-N-methoxy-N-methyl-benzenesulfonamide To a stirred solution of 6-chloro-3-(2-ethoxy-3,4-dioxo-cyclobut-1-enylamino)-2-hydroxy-N-methoxy-N-methyl-benzenesulfonamide (Intermediate A) (1 g, 2.56 mmol) in THF (20 ml) was added 3-aminopentane (0.596 ml, 5.12 mmol). The reaction mixture was heated at 50° C. overnight. The reaction mixture was concentrated in vacuo and dissolved in EtOAc. The EtOAc solution was washed with 1M HCl(aq) and brine. The EtOAc solution was dried (MgSO$_4$) and concentrated in vacuo. The residue was crystallized from toluene to give a solid; [M+H]$^+$ 432.1. $^1$H NMR (DMSO) 0.9 (6H, t, 2×CH3), 1.5 (2H, m), 1.6 (2H, m), 3.0 (3H, s, CH3), 3.6 (3H, s, CH3), 3.9 (1H, m), 7.2 (1H, d), 8.1 (1H, d), 8.2 (1H, d). 9.4 (1H, s), 10.1 (1H, s).

Example 9

3-[2-((R)-sec-Butylamino)-3,4-dioxo-cyclobut-1-enylamino]-6-chloro-2-hydroxy-N-methoxy-N-methyl-benzenesulfonamide To a stirred solution of 6-chloro-3-(2-ethoxy-3,4-dioxo-cyclobut-1-enylamino)-2-hydroxy-N-methoxy-N-methyl-benzenesulfonamide (Intermediate A) (1 g, 2.56 mmol) in THF (20 ml) was added (R)-(−)-2-aminobutane (0.52 ml, 5.12 mmol). The reaction mixture was heated at 50° C. for 7 hours. The reaction mixture was concentrated in vacuo and dissolved in EtOAc. The EtOAc solution was washed with 1M HCl(aq) and brine. The EtOAc solution was dried (MgSO$_4$) and concentrated in vacuo. The residue was crystallized from toluene to give a solid; [M+H]$^+$ 418.2. $^1$H NMR (DMSO) 0.9 (3H, t, CH3), 1.2 (3H, d, CH3), 1.5 (2H, m), 3.0 (3H, s, CH3), 3.6 (3H, s, CH3), 4.0 (1H, m), 7.2 (1H, d), 8.1 (1H, d), 8.3 (1H, d), 9.4 (1H, s), 10.1 (1H, s).

Example 10

3-[2-((R)-sec-Butylamino)-3,4-dioxo-cyclobut-1-enylamino]-6-chloro-N-ethyl-2-hydroxy-N-methoxy-benzenesulfonamide To a stirred solution of 6-Chloro-3-(2-ethoxy-3,4-dioxo-cyclobut-1-enylamino)-2-hydroxy-N-methoxy-N-ethyl-benzenesulfonamide (Intermediate FA) (100 mg, 0.25 mmol) in MeCN (1 ml) and EtOH (1 ml) was added (R)-(−)-2-Aminobutane (30.7 mg, 0.42 mmol) followed by triethylamine (69 µl, 0.49 mmol). The reaction mixture was heated at 70° C. for 1 hour. The reaction mixture was concentrated in vacuo and dissolved in EtOAc. The EtOAc solution was washed with 1M HCl (aq) and concentrated in vacuo. The residue was triturated with DCM to give a white solid; [M+H]$^+$ 432.2. $^1$H NMR (DMSO) 0.9 (3H, t, CH3), 1.2 (6H, m), 1.5-1.6 (2H, m), 3.3 (2H, m), 3.7 (3H, s, CH3) 4.1 (1H, m), 7.3 (1H, d), 8.1 (1H, d), 8.3 (1H, d), 9.4 (1H, s), 10.1 (1H, s).

Example 11

6-Chloro-2-hydroxy-N-methoxy-3-[2-((R)-1-methoxymethyl-2-methyl-propylamino)-3,4-dioxo-cyclobut-1-enylamino]-N-methyl-benzenesulfonamide To a stirred solution of triethylamine (1.192 ml, 8.55 mmol) and (R)-2-Amino-3-methyl-butan-1-ol (Intermediate H) in EtOH (36 ml) was added 6-chloro-3-(2-ethoxy-3,4-dioxo-cyclobut-1-enylamino)-2-hydroxy-N-methoxy-N-methyl-benzenesulfonamide (Intermediate A) (1.67 g, 4.27 mmol). The reaction mixture was heated at 85° C. for 18 hours. The reaction mixture was concentrated in vacuo and dissolved in EtOAc. The EtOAc solution was washed with 1M HCl(aq) and NaHCO3 (aq). The NaHCO3 (aq) layer was extracted with EtOAc. The EtOAc layers were combined and concentrated in vacuo. The residue was purified using flash chromatography (0-10% MeOH in DCM) to furnish a brown solid [M+H]$^+$ 462.0. $^1$H NMR (DMSO) 0.9 (6H, t, 2×CH3), 1.9 (1H, m), 3.0 (3H, s, CH3), 3.3 (3H, s, CH3), 3.5 (2H, m), 3.6 (3H, s, CH3), 4.1 (1H, m), 7.3 (1H, s), 8.1 (1H, d), 8.4 (1H, d), 9.5 (1H, s), 10.2 (1H, s).

Example 12

6-Chloro-N-ethyl-3-[2-(1-ethyl-propylamino)-3,4-dioxo-cyclobut-1-enylamino]-2-hydroxy-N-methoxy-benzenesulfonamide To a stirred solution of 6-Chloro-3-(2-ethoxy-3,4-dioxo-cyclobut-1-enylamino)-2-hydroxy-N-methoxy-N-ethyl-benzenesulfonamide (Intermediate FA) (100 mg, 0.25 mmol) in THF (2 ml) was added 3-aminopentane (29 mg, 0.25 mmol) The reaction mixture was heated at 50° C. overnight. Further 3-aminopentane (29 mg, 0.25 mmol) was added and the reaction was heated at 50° C. for 7 hours. The reaction mixture was concentrated in vacuo and dissolved in EtOAc. The EtOAc solution was washed with 10% citric acid (aq), brine, dried (sodium sulfate) and concentrated in vacuo to give a solid; [M+H]+ 446.1. $^1$H NMR (DMSO) 0.9 (6H, t, 2×CH3), 1.2 (3H, t, CH3), 1.5 (2H, m), 1.6 (2H, m), 3.3 (2H, m), 3.7 (3H, s, CH3), 3.9 (1H, m), 7.2 (1H, d), 8.1 (1H, d), 8.3 (1H, d), 9.4 (1H, s), 10.2 (1H, s).

Example 13

6-chloro-3-(2-(1,1,1,3,3,3-hexafluoropropan-2-ylamino)-3,4-dioxocyclobut-1-enylamino)-2-hydroxy-N-methoxy-N-methylbenzenesulfonamide 6-Chloro-3-(2-ethoxy-3,4-dioxocyclobut-1-enylamino)-2-hydroxy-N-methoxy-N-methylbenzenesulfonamide (Intermediate A) (50 mg, 0.102 mmol) and 1,1,1,3,3,3-hexafluoroisopropylamine (34.0 mg, 0.203 mmol) were dissolved THF (1 ml). To the solution was added methanesulfonic acid (7 μl, 0.108 mmol) and the resultant mixture was heated at 50° C. overnight (~18 hr). The solution was concentrated in vacuo and the residue was re-dissolved in DMSO (900 μl). The solution was transferred to a HPLC vial and purified using mass-directed prep system using 50-98% acetonitrile in water (0.1% TFA). The solvent was removed from the purified fraction in vacuo. The residue was re-dissolved in MeOH the solvent was removed in vacuo to afford the title compound as an orange solid;

MS m/z 512 [M+H]+; $^1$H NMR (400 MHz, DMSO-d6) δ 10.21 (1H, s), 9.70 (1H, s), 9.43 (1H, d), 8.01 (1H, d), 7.30 (1H, d), 6.05 (1H, m), 3.64 (3H, s), 3.04 (3H, s).

The compounds of the following tabulated (Table 2) are prepared by a similar method to that of Example 1 using the appropriate starting compounds and amines, the preparations of which are either described herein or are commercially available.

TABLE 2

| Ex. | Structure | IUPAC Name/NMR | [M + H]+ |
|---|---|---|---|
| 2.1 | 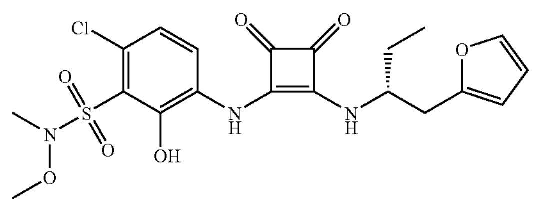 | 6-Chloro-3-[2-((R)-1-furan-2-ylmethyl-propylamino)-3,4-dioxo-cyclobut-1-enylamino]-2-hydroxy-N-methoxy-N-methyl-benzenesulfonamide | 484 |
| 2.2 | 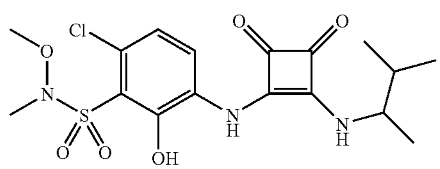 | 6-Chloro-3-[2-(1,2-dimethyl-propylamino)-3,4-dioxo-cyclobut-1-enylamino]-2-hydroxy-N-methoxy-N-methyl-benzenesulfonamide | 432 |
| 2.3 | 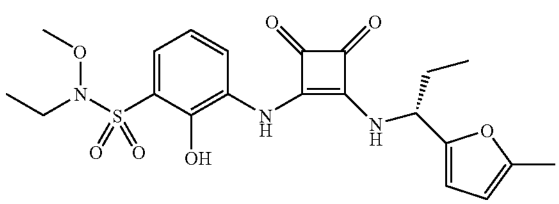 | N-Ethyl-2-hydroxy-N-methoxy-3-{2-[(R)-1-(5-methyl-furan-2-yl)-propylamino]-3,4-dioxo-cyclobut-1-enylamino}-benzenesulfonamide | 464 |
| 2.4 | 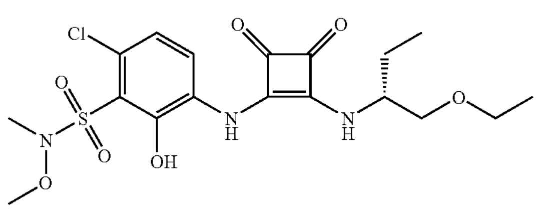 | 6-Chloro-3-[2-((R)-1-ethoxymethyl-propylamino)-3,4-dioxo-cyclobut-1-enylamino]-2-hydroxy-N-methoxy-N-methyl-benzenesulfonamide | 462 |
| 2.5 | 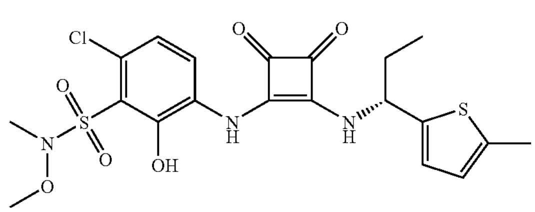 | 6-Chloro-2-hydroxy-N-methoxy-N-methyl-3-{2-[(R)-1-(5-methyl-thiophen-2-yl)-propylamino]-3,4-dioxo-cyclobut-1-enylamino}-enzenesulfonamide | 500 |

TABLE 2-continued

| Ex. | Structure | IUPAC Name/NMR | [M + H]+ |
|---|---|---|---|
| 2.6 | 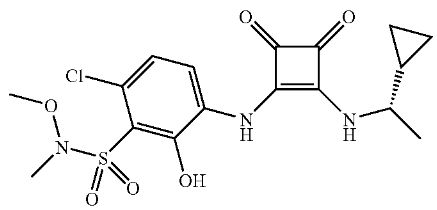 | 6-Chloro-3-[2-((S)-1-cyclopropyl-ethylamino)-3,4-dioxo-cyclobut-1-enyl amino]-2-hydroxy-N-methoxy-N-methyl-benzenesulfonamide | 430 |
| 2.7 | 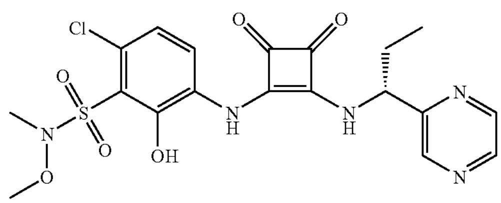 | 6-Chloro-3-[3,4-dioxo-2-((R)-1-pyrazin-2-yl-propylamino)-cyclobut-1-enylamino]-2-hydroxy-N-methoxy-N-methyl-benzenesulfonamide | 482 |
| 2.8 | 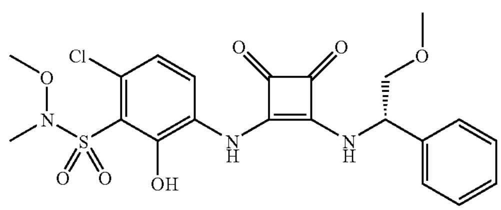 | 6-Chloro-2-hydroxy-N-methoxy-3-[2-((S)-2-methoxy-1-phenyl-ethylamino}-3,4-dioxo-cyclobut-1-enylamino]-N-methyl-benzenesulfonamide | 496 |
| 2.9 | 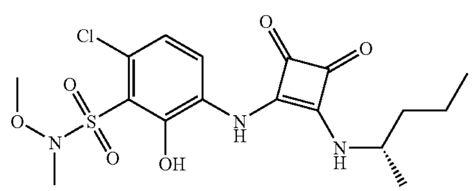 | 6-Chloro-2-hydroxy-N-methoxy-N-methyl-3-[2-((S)-1-methyl-butylamino)-3,4-dioxo-cyclobut-1-enylamino]-benzenesulfonamide | 432 |
| 2.10 | 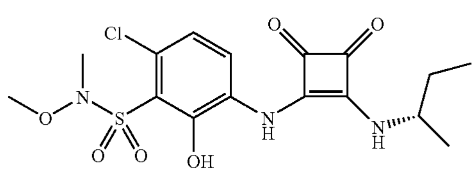 | 3-[2-((S)-sec-Butylamino)-3,4-dioxo-cyclobut-1-enylamino]-6-chloro-2-hydroxy-N-methoxy-N-methyl-benzenesulfonamide | 418 |
| 2.11 | 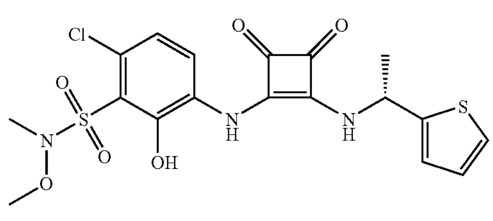 | 6-Chloro-3-[3,4-dioxo-2-((R)-1-thiophen-2-yl-ethylamino)-cyclobut-1-enylamino]-2-hydroxy-N-methoxy-N-methyl-benzenesulfonamide | 472 |
| 2.12 | 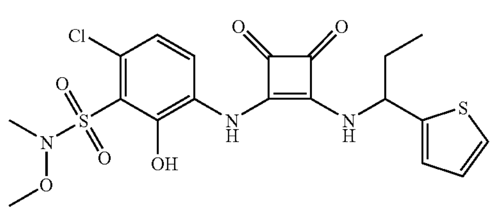 | 6-Chloro-3-[3,4-dioxo-2-((R)-1-thiophen-2-yl-propylamino)-cyclobut-1-enylamino]-2-hydroxy-N-methoxy-N-methyl-benzenesulfonamide | 486 |

TABLE 2-continued

| Ex. | Structure | IUPAC Name/NMR | [M + H]+ |
|---|---|---|---|
| 2.13 | 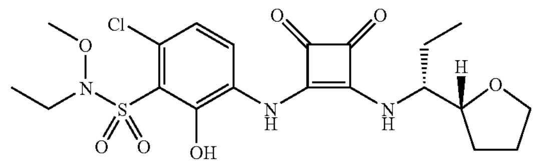 | 6-Chloro-3-{3,4-dioxo-2-[(R)-(R)-1-(tetrahydro-furan-2-yl)-propylamino]-cyclobut-1-enylamino}-N-ethyl-2-hydroxy-N-methoxy-benzene sulfonamide<br>$^1$H NMR (DMSO) 1.05 (3H, t, CH$_3$), 1.3 (3H, t, CH$_3$), 1.7 (3H, m), 1.95 (2H, m, CH$_2$), 2.1 (1H, m, CH$_2$), 3.4 (2H, m, CH$_2$O), 3.75 (3H, s, CH$_3$O), 3.8 (1H, m), 3.9 (2H, m), 4.15 (1H, m), 7.15 (1H, d, ArH), 8.25 (1H, d, ArH) | 488 |
| 2.14 | 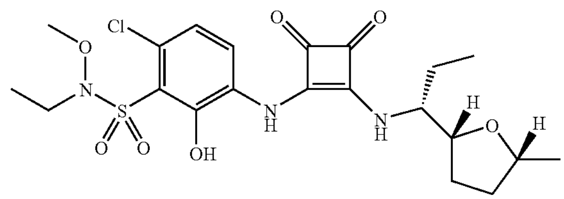 | 6-Chloro-N-ethyl-2-hydroxy-N-methoxy-3-{2-[(R)-1-((2R, 5R)-5-methyl-tetrahydro-furan-2-yl)-propylamino]-3,4-dioxo-cyclobut-1-enylamino}-benzenesulfonamide | 502 |
| 2.15 | 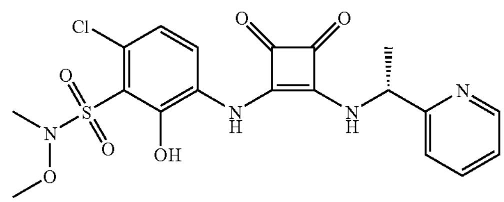 | 6-Chloro-3-[3,4-dioxo-2-((R)-1-pyridin-2-yl-ethylamino)-cyclobut-1-enylamino]-2-hydroxy-N-methoxy-N-methyl-benzenesulfonamide | 467 |
| 2.16 | 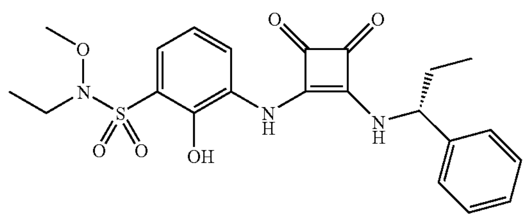 | 3-[3,4-Dioxo-2-((R)-1-phenyl-propylamino)-cyclobut-1-enylamino]-N-ethyl-2-hydroxy-N-methoxy-benzenesulfonamide | 460 |
| 2.17 | 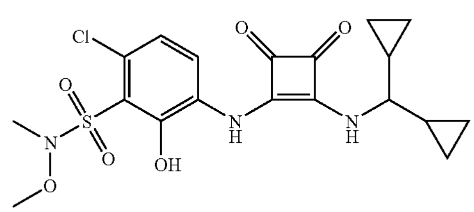 | 6-chloro-3-(2-(dicyclopropylmethylamino)-3,4-dioxocyclobut-1-enylamino)-2-hydroxy-N-methoxy-N-methylbenzenesulfonamide | 456 |
| 2.18 | 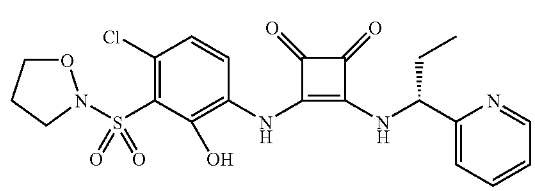 | 3-[4-Chloro-2-hydroxy-3-(isoxazolidine-2-sulfonyl)-phenylamino]-4-((R)-1-pyridin-2-yl-propylamino)-cyclobut-3-ene-1,2-dione | 493 |
| 2.19 | 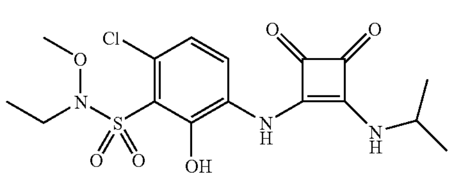 | 6-chloro-N-ethyl-2-hydroxy-3-(2-(isopropylamino)-3,4-dioxocyclobut-1-enylamino)-N-methoxybenzenesulfonamide<br>1H NMR (DMSO) 1.2 (3H, t, CH3), 1.25 (6H, d, 2xCH3), 3.30 (2H, q, CH2), 3.70 (3H, s, CH3), 4.20 (1H, m, CH), 7.15 (1H, d), 8.10 (1H, d), 8.40 (1H, d), 9.40 (1H, s), 10.15 (1H, s) | 418 |

TABLE 2-continued

| Ex. | Structure | IUPAC Name/NMR | [M + H]+ |
|---|---|---|---|
| 2.20 | 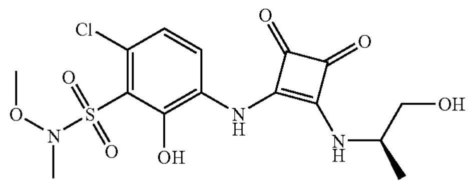 | (R)-6-chloro-2-hydroxy-3-(2-(1-hydroxypropan-2-ylamino)-3,4-dioxocyclobut-1-enylamino)-N-methoxy-N-methyl benzenesulfonamide | 420 |
| 2.21 | 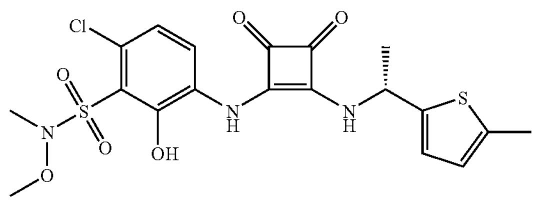 | (R)-6-chloro-2-hydroxy-N-methoxy-N-methyl-3-(2-(1-(5-methylthiophen-2-yl)ethylamino)-3,4-dioxocyclobut-1-enylamino)benzenesulfonamide | 486 |
| 2.22 | 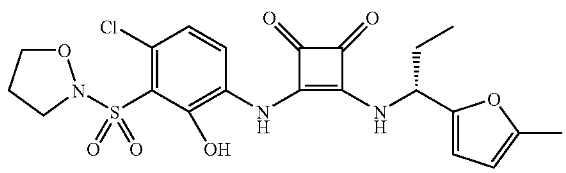 | (R)-3-(4-chloro-2-hydroxy-3-(isoxazolidin-2-ylsulfonyl)phenylamino)-4-(1-(5-methylfuran-2-yl)propylamino)cyclobut-3-ene-1,2-dione | 496 |
| 2.23 | 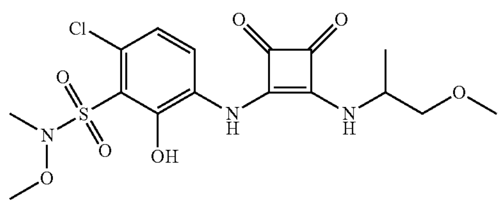 | 6-chloro-2-hydroxy-N-methoxy-3-(2-(1-methoxypropan-2-ylamino)-3,4-dioxocyclobut-1-enylamino)-N-methylbenzenesulfonamide<br>$^1$H NMR (DMSO) 1.2 (3H, d, CH3), 3.0 (3H, s, CH3N), 3.35 (3H, s, CH3O), 3.42 (2H, m, CH2O), 3.62 (3H, s, CH3O), 4.35 (1H, m, CHN), 8.05 (1H, d, ArH), 8.56 (1H, d, ArH), | 434 |
| 2.24 | 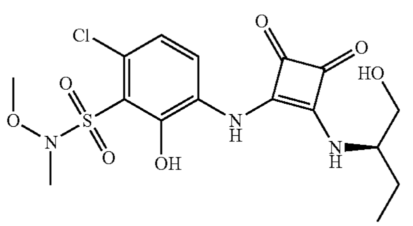 | (R)-6-chloro-2-hydroxy-3-(2-(1-hydroxybutan-2-ylamino)-3,4-dioxocyclobut-1-enylamino)-N-methoxy-N-methylbenzenesulfonamide | 434 |
| 2.25 | 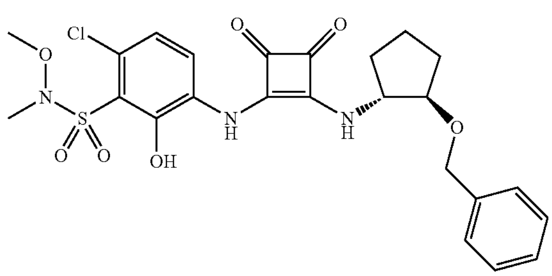 | 3-(2-((1R,2R)-2-(benzyloxy)cyclopentylamino)-3,4-dioxocyclobut-1-enylamino)-6-chloro-2-hydroxy-N-methoxy-N-methylbenzenesulfonamide | 536 |
| 2.26 | 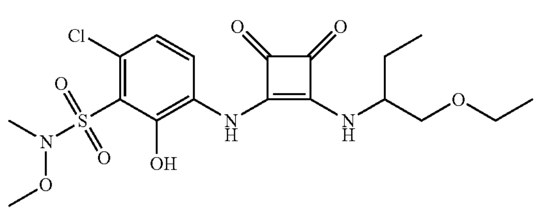 | 6-chloro-3-(2-(1-ethoxybutan-2-ylamino)-3,4-dioxocyclobut-1-enylamino)-2-hydroxy-N-methoxy-N-methylbenzenesulfonamide | 462 |

TABLE 2-continued

| Ex. | Structure | IUPAC Name/NMR | [M + H]+ |
|---|---|---|---|
| 2.27 | 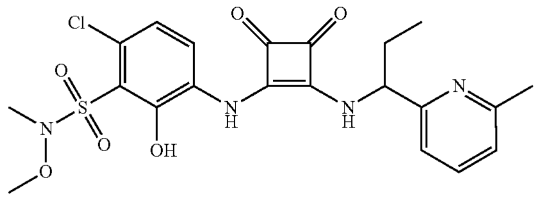 | 6-chloro-2-hydroxy-N-methoxy-N-methyl-3-(2-(1-(6-methylpyridin-2-yl)propylamino)-3,4-dioxocyclobut-1-enylamino)benzenesulfonamide<br>1H NMR (MeOD) 1.0 (3H, t, CH$_3$), 2.05 (2H, m, CH$_2$), 2.6 (3H, s, ArCH$_3$), 3.1 (3H, s, CH$_3$N), 3.7 (3H, s, CH$_3$O), 5.3 (1H, m, CHN), 7.2 (2H, 2 x ArH), 7.7 (1H, t, ArH), 8.2 (1H, d, ArH) | 495 |
| 2.28 | 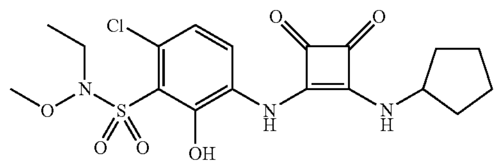 | 6-chloro-3-(2-(cyclopentylamino)-3,4-dioxocyclobut-1-enylamino)-N-ethyl-2-hydroxy-N-methoxybenzenesulfonamide | 444 |
| 2.29 | 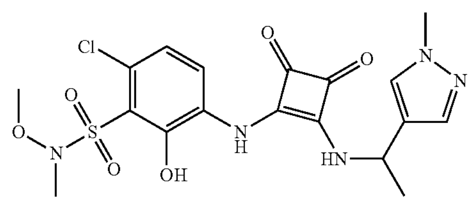 | 6-chloro-2-hydroxy-N-methoxy-N-methyl-3-(2-(1-(1-methyl-1H-pyrazol-4-yl)ethylamino)-3,4-dioxocyclobut-1-enylamino)benzenesulfonamide | 470 |
| 2.30 | 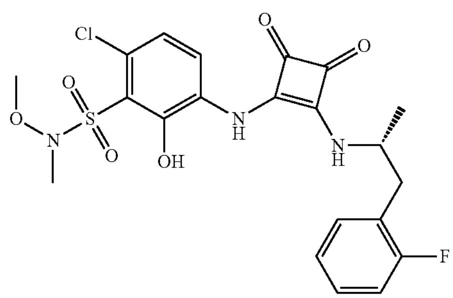 | (R)-6-chloro-3-(2-(1-(2-fluorophenyl)propan-2-ylamino)-3,4-dioxocyclobut-1-enylamino)-2-hydroxy-N-methoxy-N-methylbenzenesulfonamide | 498 |
| 2.31 | 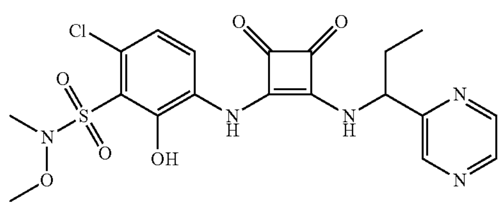 | 6-chloro-3-(3,4-dioxo-2-(1-(pyrazin-2-yl)propylamino)cyclobut-1-enylamino)-2-hydroxy-N-methoxy-N-methylbenzenesulfonamide | 482 |
| 2.32 | 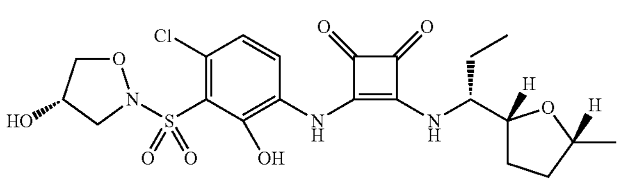 | 3-(4-chloro-2-hydroxy-3-((S)-4-hydroxyisoxazolidin-2-ylsulfonyl)phenylamino)-4-((R)-1-((2R,5R)-5-methyltetrahydrofuran-2-yl)propylamino)cyclobut-3-ene-1,2-dione | 517 |
| 2.33 | 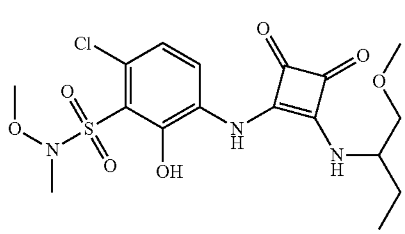 | 6-chloro-2-hydroxy-N-methoxy-3-(2-(1-methoxybutan-2-ylamino)-3,4-dioxocyclobut-1-enylamino)-N-methylbenzenesulfonamide | 448 |

TABLE 2-continued

| Ex. | Structure | IUPAC Name/NMR | [M + H]+ |
|---|---|---|---|
| 2.34 | 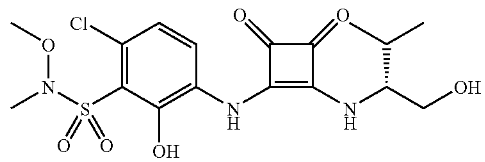 | (R)-6-chloro-2-hydroxy-3-(2-(1-hydroxy-3-methylbutan-2-ylamino)-3,4-dioxocyclobut-1-enylamino)-N-methoxy-N-methylbenzenesulfonamide | 448 |
| 2.35 | 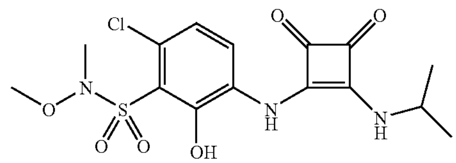 | 6-chloro-2-hydroxy-3-(2-(isopropylamino)-3,4-dioxocyclobut-1-enylamino)-N-methoxy-N-methylbenzenesulfonamide<br>1H NMR (DMSO) 1.25 (6H, d, 2xCH3), 3.05 (3H, s, CH3), 3.65 (3H, s, CH3), 4.20 (1H, m, CH), 7.30 (1H, d), 8.10 (1H, d), 8.40 (1H, d), 9.40 (1H, s), 10.15 (1H, s) | 404 |
| 2.36 | 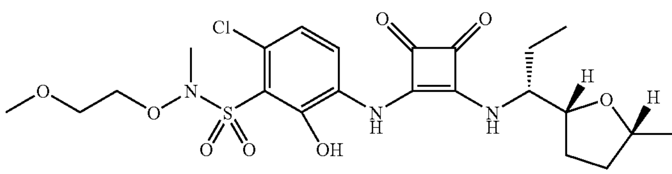 | 6-chloro-2-hydroxy-N-(2-methoxyethoxy)-N-methyl-3-(2-((R)-1-((2R,5R)-5-methyltetrahydrofuran-2-yl)propylamino)-3,4-dioxocyclobut-1-enylamino)benzenesulfonamide | 532 |
| 2.37 | 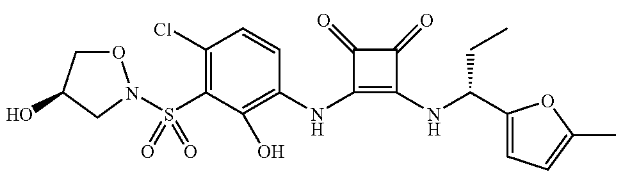 | 3-(4-chloro-2-hydroxy-3-((R)-4-hydroxyisoxazolidin-2-ylsulfonyl)phenylamino)-4-((R)-1-(5-methylfuran-2-yl)propylamino)cyclobut-3-ene-1,2-dione | 512 |
| 2.38 | 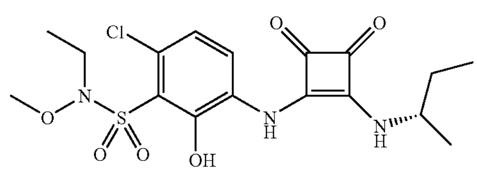 | (S)-3-(2-(sec-butylamino)-3,4-dioxocyclobut-1-enylamino)-6-chloro-N-ethyl-2-hydroxy-N-methoxybenzenesulfonamide | 432 |
| 2.39 | 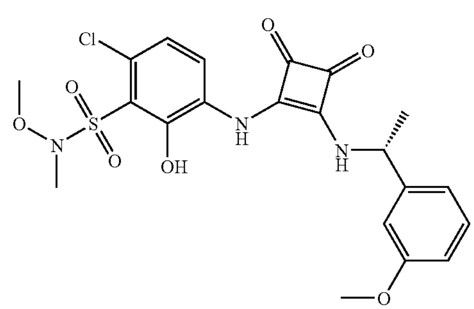 | (R)-6-chloro-2-hydroxy-N-methoxy-3-(2-(1-(3-methoxyphenyl)ethylamino)-3,4-dioxocyclobut-1-enylamino)-N-methylbenzenesulfonamide | 496 |
| 2.40 | 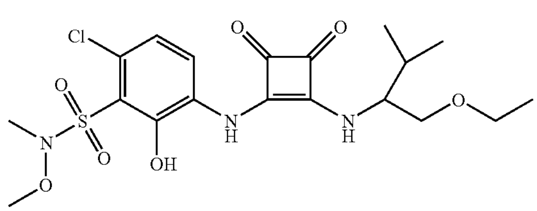 | 6-chloro-3-(2-(1-ethoxy-3-methylbutan-2-ylamino)-3,4-dioxocyclobut-1-enylamino)-2-hydroxy-N-methoxy-N-methylbenzenesulfonamide | 476 |

TABLE 2-continued

| Ex. | Structure | IUPAC Name/NMR | [M + H]+ |
|---|---|---|---|
| 2.41 | 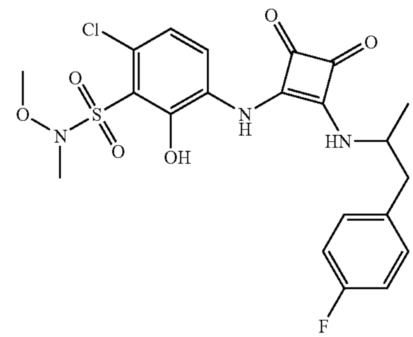 | 6-chloro-3-(2-(1-(4-fluorophenyl)propan-2-ylamino)-3,4-dioxocyclobut-1-enylamino)-2-hydroxy-N-methoxy-N-methylbenzenesulfonamide | 498 |
| 2.42 | 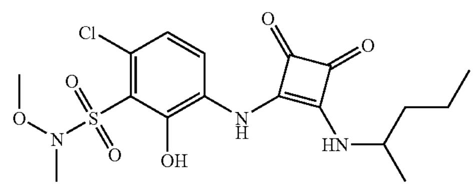 | 6-chloro-3-(3,4-dioxo-2-(pentan-2-ylamino)cyclobut-1-enylamino)-2-hydroxy-N-methoxy-N-methylbenzenesulfonamide | 432 |
| 2.43 | 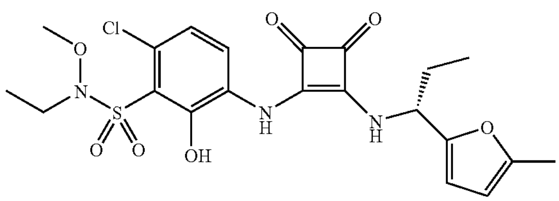 | (R)-6-chloro-N-ethyl-2-hydroxy-N-methoxy-3-(2-(1-(5-methylfuran-2-yl)propylamino)-3,4-dioxocyclobut-1-enylamino)benzenesulfonamide | 498 |
| 2.44 | 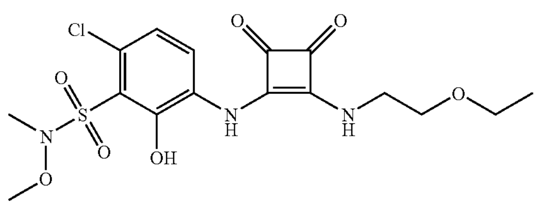 | (R)-6-chloro-3-(2-(1-ethoxypropan-2-ylamino)-3,4-dioxocyclobut-1-enylamino)-2-hydroxy-N-methoxy-N-methylbenzenesulfonamide | 448/450 |
| 2.45 | 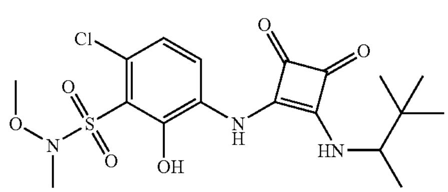 | 6-chloro-3-(2-(3,3-dimethylbutan-2-ylamino)-3,4-dioxocyclobut-1-enylamino)-2-hydroxy-N-methoxy-N-methylbenzenesulfonamide | 446 |
| 2.46 | 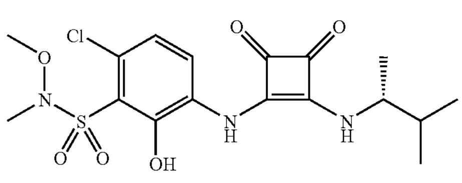 | (R)-6-chloro-2-hydroxy-N-methoxy-N-methyl-3-(2-(3-methylbutan-2-ylamino)-3,4-dioxocyclobut-1-enylamino)benzenesulfonamide | 432 |
| 2.47 | 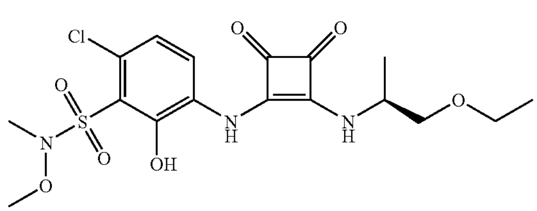 | (S)-6-chloro-3-(2-(1-ethoxypropan-2-ylamino)-3,4-dioxocyclobut-1-enylamino)-2-hydroxy-N-methoxy-N-methylbenzenesulfonamide | 448/450 |

… TABLE 2-continued

| Ex. | Structure | IUPAC Name/NMR | [M + H]+ |
| --- | --- | --- | --- |
| 2.48 | 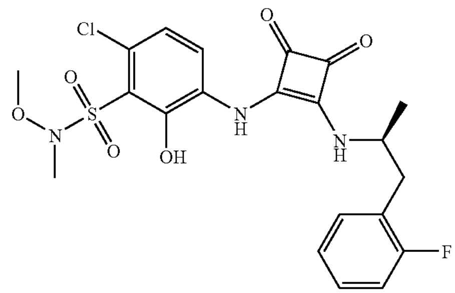 | (S)-6-chloro-3-(2-(1-(2-fluorophenyl)propan-2-ylamino)-3,4-dioxocyclobut-1-enylamino)-2-hydroxy-N-methoxy-N-methylbenzenesulfonamide | 498 |
| 2.49 | 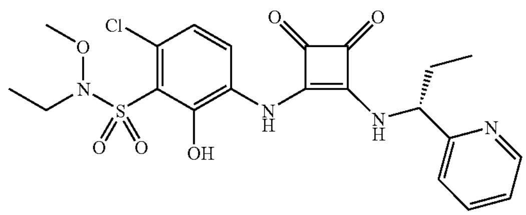 | (R)-6-chloro-3-(3,4-dioxo-2-(1-(pyridin-2-yl)propylamino)cyclobut-1-enylamino)-N-ethyl-2-hydroxy-N-methoxybenzenesulfonamide | 495 |
| 2.50 | 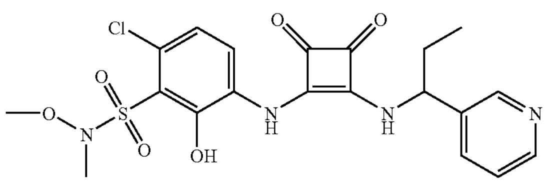 | 6-chloro-3-(3,4-dioxo-2-(1-(pyridin-3-yl)propylamino)cyclobut-1-enylamino)-2-hydroxy-N-methoxy-N-methylbenzenesulfonamide<br>$^1$H NMR (MeOD) 1.03 (3H, t, CH$_3$), 2.05 (2H, m, CH$_2$), 3.08 (3H, s, CH$_3$N), 3.68 (3H, s, CH$_3$O), 6.3 (1H, t CHN), 7.18 (1H, d, ArH), 7.5 (1H, m, ArH), 7.9 (1H, d, ArH), 8.28 (1H, d, ArH), 8.5 (1H, d, ArH), 8.62 (1H, s, ArH) | 481 |
| 2.51 | 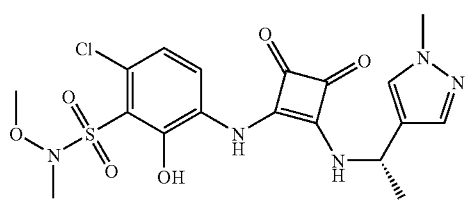 | (S)-6-chloro-2-hydroxy-N-methoxy-N-methyl-3-(2-(1-(1-methyl-1H-pyrazol-4-yl)ethylamino)-3,4-dioxocyclobut-1-enylamino)benzenesulfonamide | 470 |
| 2.52 | 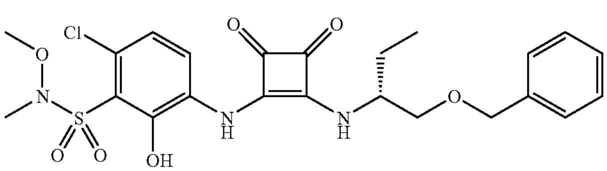 | (R)-3-(2-(1-(benzyloxy)butan-2-ylamino)-3,4-dioxocyclobut-1-enylamino)-6-chloro-2-hydroxy-N-methoxy-N-methylbenzenesulfonamide | 524 |
| 2.53 | 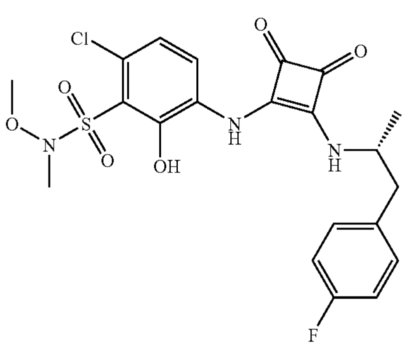 | (R)-6-chloro-3-(2-(1-(4-fluorophenyl)propan-2-ylamino)-3,4-dioxocyclobut-1-enylamino)-2-hydroxy-N-methoxy-N-methylbenzenesulfonamide | 498 |

TABLE 2-continued

| Ex. | Structure | IUPAC Name/NMR | [M + H]+ |
| --- | --- | --- | --- |
| 2.54 | 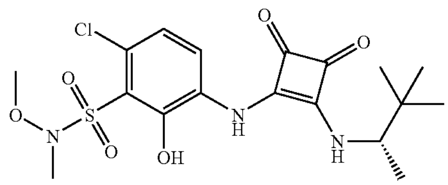 | (S)-6-chloro-3-(2-(3,3-dimethylbutan-2-ylamino)-3,4-dioxocyclobut-1-enylamino)-2-hydroxy-N-methoxy-N-methylbenzenesulfonamide | 446 |
| 2.55 | 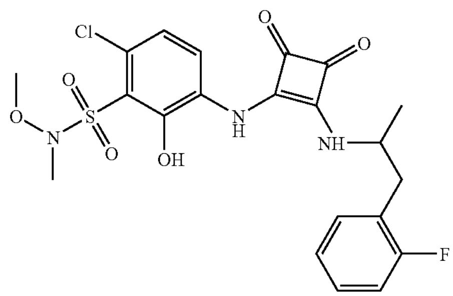 | 6-chloro-3-(2-(1-(2-fluorophenyl)propan-2-ylamino)-3,4-dioxocyclobut-1-enylamino)-2-hydroxy-N-methoxy-N-methylbenzenesulfonamide | 498 |
| 2.56 | 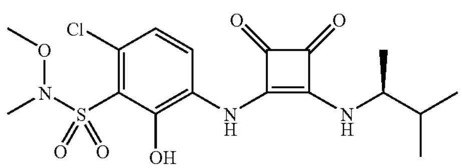 | (S)-6-chloro-2-hydroxy-N-methoxy-N-methyl-3-(2-(3-methylbutan-2-ylamino)-3,4-dioxocyclobut-1-enylamino)benzenesulfonamide | 432 |
| 2.57 | 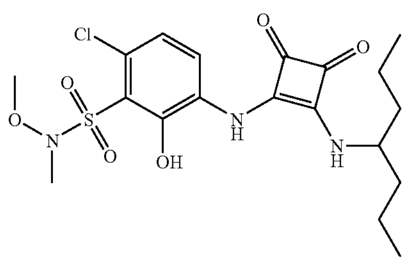 | 6-chloro-3-(2-(heptan-4-ylamino)-3,4-dioxocyclobut-1-enylamino)-2-hydroxy-N-methoxy-N-methylbenzenesulfonamide | 460 |
| 2.58 | 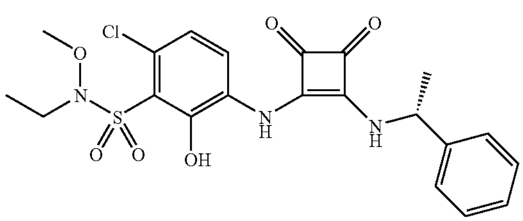 | (R)-6-chloro-3-(3,4-dioxo-2-(1-phenylethylamino)cyclobut-1-enylamino)-N-ethyl-2-hydroxy-N-methoxybenzenesulfonamide<br>$^1$H NMR (DMSO) 1.20 (3H, t CH3), 1.60 (3H, d, CH3), 3.30 (2H, q, CH2), 3.70 (3H, s, CH3), 5.35 (1H, m, CH), 7.25 (1H, d), 7.30 (1H, m), 7.40 (4H, m), 8.10 (1H, d), 8.80 (1H, d), 9.40 (1H, s), 10.15 (1H, s) | 480 |
| 2.59 | 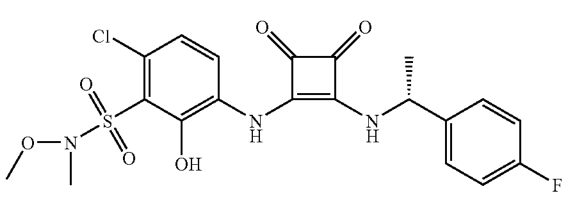 | (R)-6-chloro-3-(2-(1-(4-fluorophenyl)ethylamino)-3,4-dioxocyclobut-1-enylamino)-2-hydroxy-N-methoxy-N-methylbenzenesulfonamide | 484 |
| 2.60 | 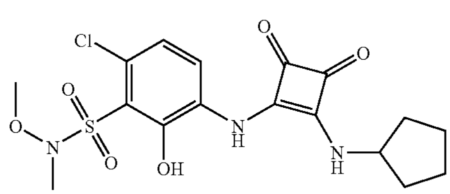 | 6-chloro-3-(2-(cyclopentylamino)-3,4-dioxocyclobut-1-enylamino)-2-hydroxy-N-methoxy-N-methylbenzenesulfonamide | 430 |

TABLE 2-continued

| Ex. | Structure | IUPAC Name/NMR | [M + H]+ |
|---|---|---|---|
| 2.61 | 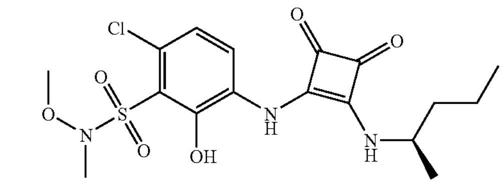 | (R)-6-chloro-3-(3,4-dioxo-2-(pentan-2-ylamino)cyclobut-1-enylamino)-2-hydroxy-N-methoxy-N-methylbenzenesulfonamide | 432 |
| 2.62 | 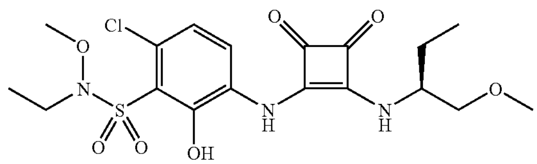 | (S)-6-chloro-N-ethyl-2-hydroxy-N-methoxy-3-(2-(1-methoxybutan-2-ylamino)-3,4-dioxocyclobut-1-enylamino)benzenesulfonamide | 462 |
| 2.63 | 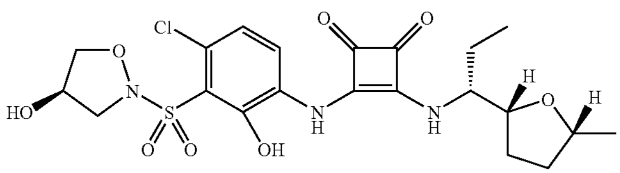 | 3-(4-chloro-2-hydroxy-3-((R)-4-hydroxyisoxazolidin-2-ylsulfonyl)phenylamino)-4-((R)-1-((2R,5R)-5-methyltetrahydrofuran-2-yl)propylamino)cyclobut-3-ene-1,2-dione | 517 |
| 2.64 | 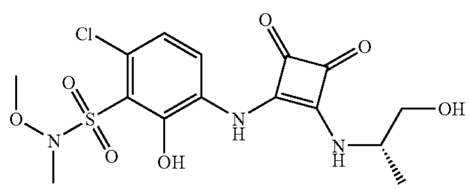 | (S)-6-chloro-2-hydroxy-3-(2-(1-hydroxypropan-2-ylamino)-3,4-dioxocyclobut-1-enylamino)-N-methoxy-N-methylbenzenesulfonamide | 420 |
| 2.65 | 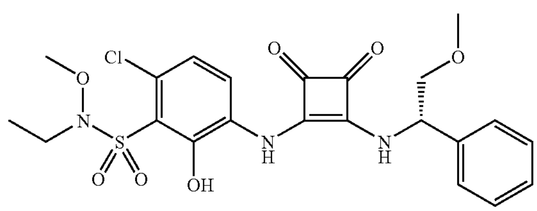 | (S)-6-chloro-N-ethyl-2-hydroxy-N-methoxy-3-(2-(2-methoxy-1-phenylethylamino)-3,4-dioxocyclobut-1-enylamino)benzenesulfonamide | 510 |
| 2.66 | 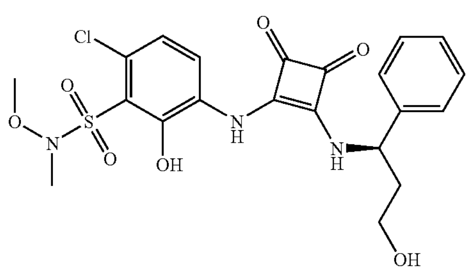 | (R)-6-chloro-2-hydroxy-3-(2-(3-hydroxy-1-phenylpropylamino)-3,4-dioxocyclobut-1-enylamino)-N-methoxy-N-methylbenzenesulfonamide | 496 |
| 2.67 | 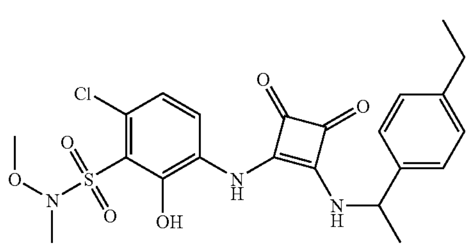 | 6-chloro-3-(2-(1-(4-ethylphenyl)ethylamino)-3,4-dioxocyclobut-1-enylamino)-2-hydroxy-N-methoxy-N-methylbenzenesulfonamide | 494 |

TABLE 2-continued

| Ex. | Structure | IUPAC Name/NMR | [M + H]+ |
|---|---|---|---|
| 2.68 | 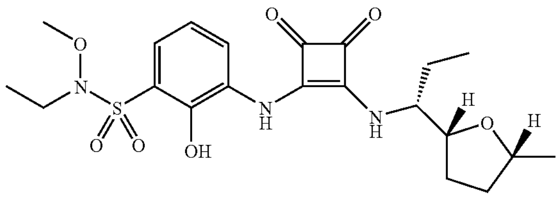 | N-ethyl-2-hydroxy-N-methoxy-3-(2-((R)-1-((2R,5R)-5-methyltetrahydrofuran-2-yl)propylamino)-3,4-dioxocyclobut-1-enylamino)benzenesulfonamide | 468 |
| 2.69 | 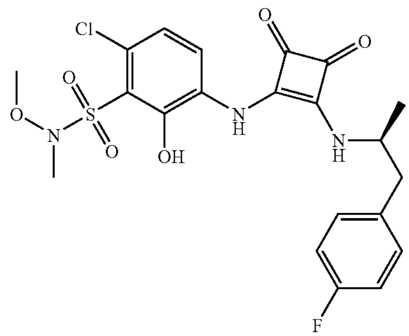 | (S)-6-chloro-3-(2-(1-(4-fluorophenyl)propan-2-ylamino)-3,4-dioxocyclobut-1-enylamino)-2-hydroxy-N-methoxy-N-methylbenzenesulfonamide | 498 |
| 2.70 | 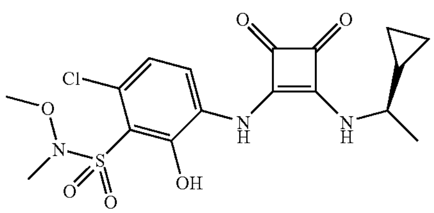 | (R)-6-chloro-3-(2-(1-cyclopropylethylamino)-3,4-dioxocyclobut-1-enylamino)-2-hydroxy-N-methoxy-N-methylbenzenesulfonamide | 430 |
| 2.71 | 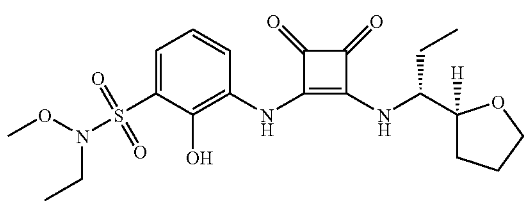 | 3-(3,4-dioxo-2-((R)-1-((S)-tetrahydrofuran-2-yl)propylamino)cyclobut-1-enylamino)-N-ethyl-2-hydroxy-N-methoxybenzenesulfonamide<br>$^1$H NMR (DMSO) 0.95 (3H, t, CH$_3$), 1.2 (3H, t, CH$_3$), 1.6 (2H, m), 1.7 (1H, m), 1.85 (2H, m), 1.95 (1H, m), 3.1 (2H, m, CH$_2$N), 3.65 (1H, m, CHN), 3.8 (3H, s, CH$_3$ON), 3.9 (1H, m, CHO), 4.1 (2H, m, CH$_2$O), 7.4 (1H, d, ArH), 8.0 (1H, d, ArH), 8.3 (1H, d, ArH) | 464 |
| 2.72 | 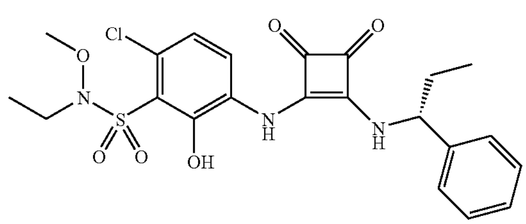 | (R)-6-chloro-3-(3,4-dioxo-2-(1-phenylpropylamino)cyclobut-1-enylamino)-N-ethyl-2-hydroxy-N-methoxybenzenesulfonamide | 494 |
| 2.73 | 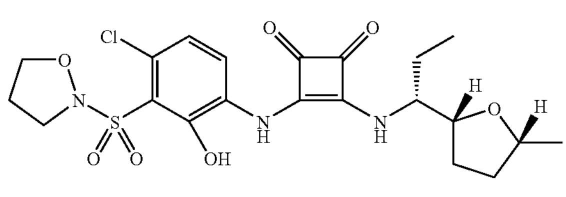 | 3-(4-chloro-2-hydroxy-3-(isoxazolidin-2-ylsulfonyl)phenylamino)-4-((R)-1-((2R,5R)-5-methyltetrahydrofuran-2-yl)propylamino)cyclobut-3-ene-1,2- | |

TABLE 2-continued

| Ex. | Structure | IUPAC Name/NMR | [M + H]+ |
|---|---|---|---|
| 2.74 | 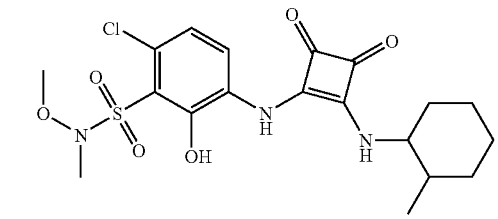 | 6-chloro-2-hydroxy-N-methoxy-N-methyl-3-(2-(2-methylcyclohexylamino)-3,4-dioxocyclobut-1-enylamino)benzenesulfonamide | 458 |
| 2.75 | 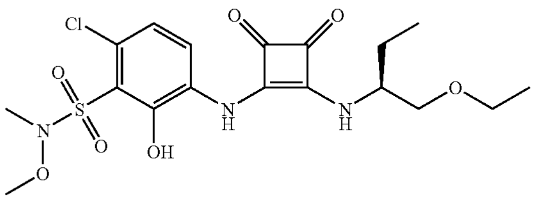 | (S)-6-chloro-3-(2-(1-ethoxybutan-2-ylamino)-3,4-dioxocyclobut-1-enylamino)-2-hydroxy-N-methoxy-N-methylbenzenesulfonamide | 462 |
| 2.76 | 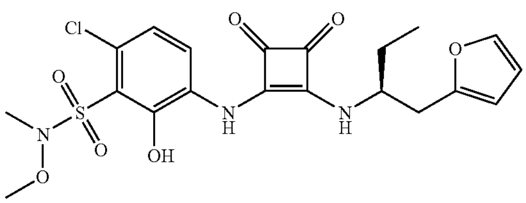 | (S)-6-chloro-3-(2-(1-(furan-2-yl)butan-2-ylamino)-3,4-dioxocyclobut-1-enylamino)-2-hydroxy-N-methoxy-N-methylbenzenesulfonamide | 484 |
| 2.77 | 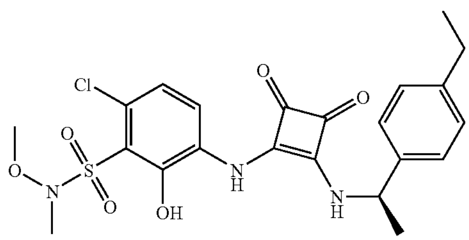 | (R)-6-chloro-3-(2-(1-(4-ethylphenyl)ethylamino)-3,4-dioxocyclobut-1-enylamino)-2-hydroxy-N-methoxy-N-methylbenzenesulfonamide | 494 |
| 2.78 | 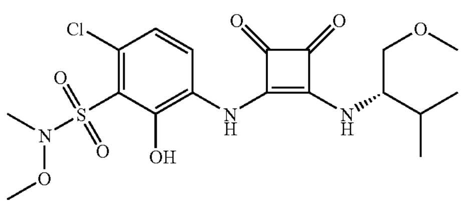 | (S)-6-chloro-2-hydroxy-N-methoxy-3-(2-(1-methoxy-3-methylbutan-2-ylamino)-3,4-dioxocyclobut-1-enylamino)-N-methylbenzenesulfonamide | 462 |
| 2.79 | 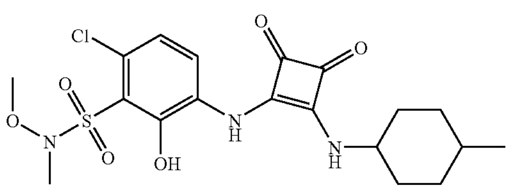 | 6-chloro-2-hydroxy-N-methoxy-N-methyl-3-(2-(4-methylcyclohexylamino)-3,4-dioxocyclobut-1-enylamino)benzenesulfonamide | 458 |
| 2.80 | 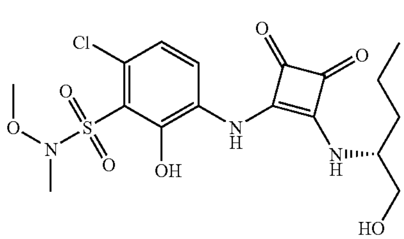 | (R)-6-chloro-2-hydroxy-3-(2-(1-hydroxypentan-2-ylamino)-3,4-dioxocyclobut-1-enylamino)-N-methoxy-N-methylbenzenesulfonamide | 448 |

TABLE 2-continued

| Ex. | Structure | IUPAC Name/NMR | [M + H]+ |
|---|---|---|---|
| 2.81 | 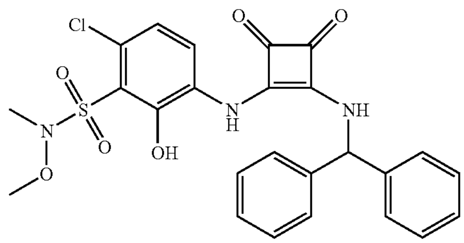 | 3-(2-(benzhydrylamino)-3,4-dioxocyclobut-1-enylamino)-6-chloro-2-hydroxy-N-methoxy-N-methylbenzenesulfonamide | 528 |
| 2.82 | 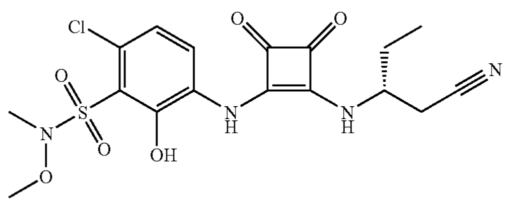 | (R)-6-chloro-3-(2-(1-cyanobutan-2-ylamino)-3,4-dioxocyclobut-1-enylamino)-2-hydroxy-N-methoxy-N-methylbenzenesulfonamide | 443/445 |
| 2.83 | 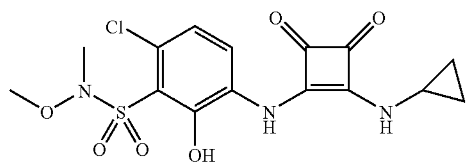 | 6-chloro-3-(2-(cyclopropylamino)-3,4-dioxocyclobut-1-enylamino)-2-hydroxy-N-methoxy-N-methylbenzenesulfonamide | 402 |
| 2.84 | 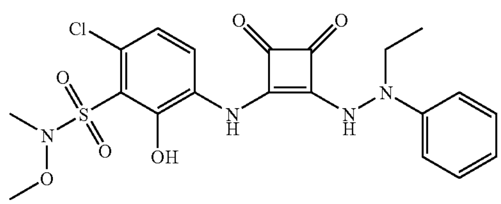 | 6-chloro-3-(2-(2-ethyl-2-phenylhydrazinyl)-3,4-dioxocyclobut-1-enylamino)-2-hydroxy-N-methoxy-N-methylbenzenesulfonamide | 481 |
| 2.85 | 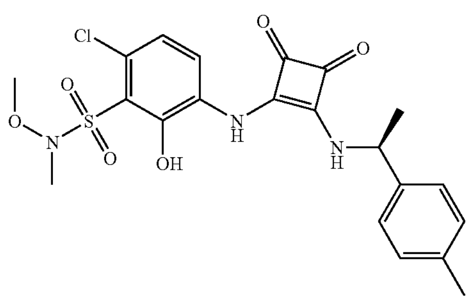 | (S)-6-chloro-3-(3,4-dioxo-2-(1-p-tolylethylamino)cyclobut-1-enylamino)-2-hydroxy-N-methoxy-N-methylbenzenesulfonamide | 480 |
| 2.86 | 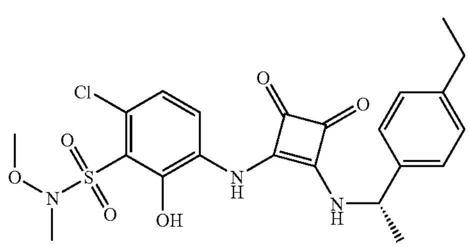 | (S)-6-chloro-3-(2-(1-(4-ethylphenyl)ethylamino)-3,4-dioxocyclobut-1-enylamino)-2-hydroxy-N-methoxy-N-methylbenzenesulfonamide | 494 |
| 2.87 | 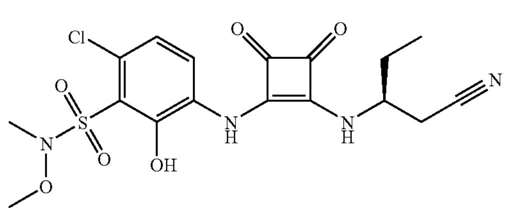 | (S)-6-chloro-3-(2-(1-cyanobutan-2-ylamino)-3,4-dioxocyclobut-1-enylamino)-2-hydroxy-N-methoxy-N-methylbenzenesulfonamide | 443/445 |

TABLE 2-continued

| Ex. | Structure | IUPAC Name/NMR | [M + H]+ |
|---|---|---|---|
| 2.88 | 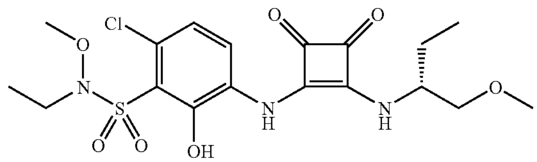 | (R)-6-chloro-N-ethyl-2-hydroxy-N-methoxy-3-(2-(1-methoxybutan-2-ylamino)-3,4-dioxacyclobut-1-enylamino)benzenesulfanamide | 462 |
| 2.89 | 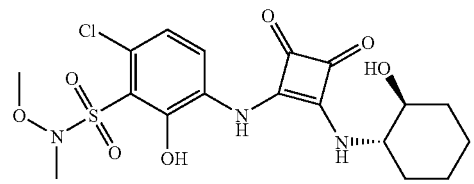 | 6-chloro-2-hydroxy-3-(2-((1S,2S)-2-hydroxycyclohexylamino)-3,4-dioxocyclobut-1-enylamino)-N-methoxy-N-methylbenzenesulfonamide | 460 |
| 2.90 | 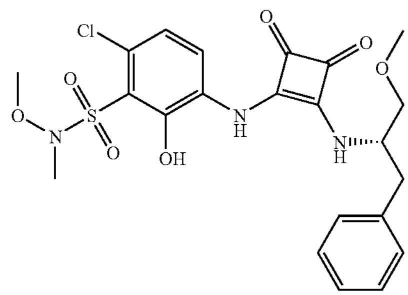 | (S)-6-chloro-2-hydroxy-N-methoxy-3-(2-(1-methoxy-3-phenylpropan-2-ylamino)-3,4-dioxocyclobut-1-enylamino)-N-methylbenzenesulfonamide | 510 |
| 2.91 | 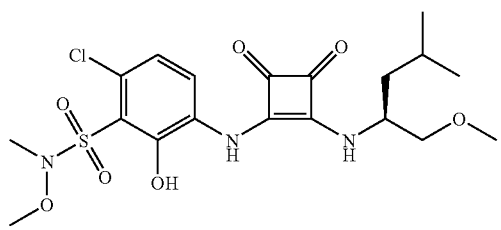 | (S)-6-chloro-2-hydroxy-N-methoxy-3-(2-(1-methoxy-4-methylpentan-2-ylamino)-3,4-dioxocyclobut-1-enylamino)-N-methylbenzenesulfonamide | 476 |
| 2.92 | 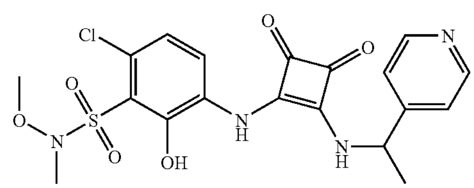 | 6-chloro-3-(3,4-dioxo-2-(1-(pyridin-4-yl)ethylamino)cyclobut-1-enylamino)-2-hydroxy-N-methoxy-N-methylbenzenesulfonamide | 467 |
| 2.93 | 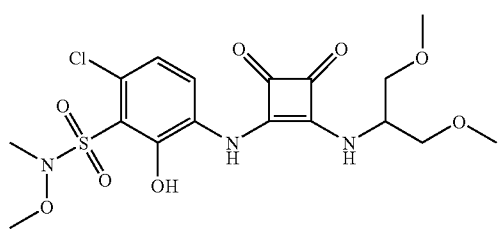 | 6-chloro-3-(2-(1,3-dimethoxypropan-2-ylamino)-3,4-dioxocyclobut-1-enylamino)-2-hydroxy-N-methoxy-N-methylbenzenesulfonamide | 464 |
| 2.94 | 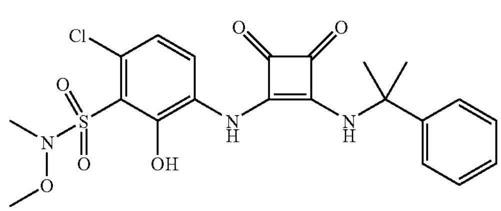 | 6-chloro-3-(3,4-dioxo-2-(2-phenylpropan-2-ylamino)cyclobut-1-enylamino)-2-hydroxy-N-methoxy-N-methylbenzenesulfonamide | 480 |

TABLE 2-continued

| Ex. | Structure | IUPAC Name/NMR | [M + H]+ |
|---|---|---|---|
| 2.95 | 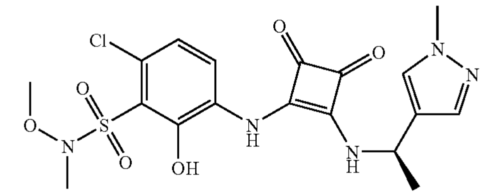 | (R)-6-chloro-2-hydroxy-N-methoxy-N-methyl-3-(2-(1-(1-methyl-1H-pyrazol-4-yl)ethylamino)-3,4-dioxocyclobut-1-enylamino)benzenesulfonamide | 470 |
| 2.96 | 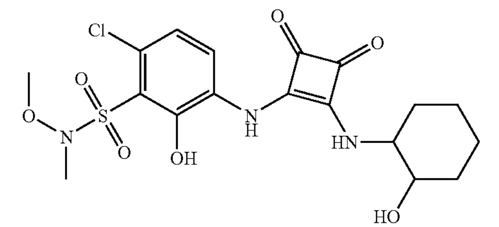 | 6-chloro-2-hydroxy-3-(2-(2-hydroxycyclohexylamino)-3,4-dioxocyclobut-1-enylamino)-N-methoxy-N-methylbenzenesulfonamide | 460 |
| 2.97 | 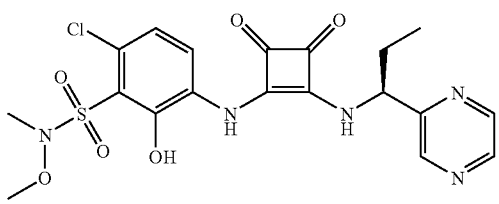 | (S)-6-chloro-3-(3,4-dioxo-2-(1-(pyrazin-2-yl)propylamino)cyclobut-1-enylamino)-2-hydroxy-N-methoxy-N-methylbenzenesulfonamide | 482 |

Preparation of Intermediate Compounds

Intermediate A

6-Chloro-3-(2-ethoxy-3,4-dioxo-cyclobut-1-enylamino)-2-hydroxy-N-methoxy-N-methyl-benzenesulfonamide Step 1:
2-tert-Butyl-6-chloro-benzooxazole-7-sulfonic acid methoxy-methyl-amide N,O-dimethylhydroxylamine (1.98 g, 2 equiv) was suspended in dry THF (20 ml) and cooled to 0° C. in an ice bath while stirring vigorously. Triethylamine (4.51 ml, 2 equiv) was added maintaining the temperature at 0° C. followed by dropwise addition of 2-tert-butyl-6-chloro-benzooxazole-7-sulfonyl chloride (US 2007/0249672 page 9) (5 g, 16.22 mmol, 1 equiv) in THF (10 ml) over 30 minutes. The reaction mixture was stirred at 0° C. for 1 h and then allowed to warm to room temperature overnight. The resulting mixture was filtered and concentrated in vacuo and the resulting solid was dissolved in EtOAc (75 ml), washed with water (3×20 ml), sat. brine (30 ml) dried (MgSO$_4$) and concentrated in vacuo to afford the title compound as a solid; [M+H]$^+$ 333.

Step 2: 3-Amino-6-chloro-2-hydroxy-N-methoxy-N-methyl-benzenesulfonamide 2-tert-Butyl-6-chloro-benzooxazole-7-sulfonic acid methoxy-methyl-amide (4.8 g, 14.42 mmol) in dioxane (55 ml) and water (20 ml) was treated with concentrated sulphuric acid (20 ml) added dropwise over 30 minutes maintaining the temperature <30° C. The reaction mixture was heated at reflux for 2.5 h and then allowed to cool to RT. Dioxane was removed in vacuo and the resulting aqueous residue was basified with sat. NaHCO$_3$ solution (250 ml) to pH12. The reaction mixture was extracted with EtOAc (3×200 ml) and the combined organic extracts were washed with water (3×100 ml) sat. brine (100 ml), dried (MgSO$_4$) and concentrated in vacuo to afford the title compound as a brown solid; [M+H]$^+$ 266.

Step 3: 6-Chloro-3-(2-ethoxy-3,4-dioxo-cyclobut-1-enylamino)-2-hydroxy-N-methoxy-N-methyl-benzenesulfonamide A solution of 3,4-diethoxy-3-cyclobutene-1,2-dione (2.83 g, 1.2 equiv) in ethanol (30 ml) was treated with TEA (1.54 g, 1.1 equiv) and the reaction mixture was heated to 45° C. 3-Amino-6-chloro-2-hydroxy-N-methoxy-N-methyl-benzenesulfonamide (3.7 g, 1 equiv) was added portion wise over 30 minutes, with vigorous stirring, maintaining the reaction mixture at 45° C. The reaction mixture was stirred at 45° C. for 1 hour and then allowed to cool to RT. The solvent was removed in vacuo and the residue was partitioned between EtOAc (600 ml) and water (2×200 ml). The aqueous portion was separated and extracted with EtOAc (3×200 ml) and the combined organic extracts were washed with water (3×200 ml) and allowed to stand over night. The resulting solid was collected by filtration and dried in vacuo to afford the title compound. The mother liquor was evaporated to give a yellow/brown oily solid which was triturated with ethanol (100 ml). The solid was collected by filtration, washed with EtOH and dried in vacuo to afford the title compound; [M+H]$^+$ 390.

Intermediate B (R)-1-(5-Methyl-furan-2-yl)-propylamine p-toluene sulphonate

This compound was prepared according to the procedure described in US 2004/0209946 page 19.

Intermediate C (S)-(Tetrahydro-thiophen-3-yl)amine

This compound was prepared according to the procedure described in Synthesis (1992), (10), 947-9.

Intermediate DA (R)-1-(Tetrahydro-furan-2-yl)-propylamine

Step 1: (R)-N-methoxy-N-methyltetrahydrofuran-2-carboxamide

To a cooled (0° C.) solution of (R) tetrahydrofuroic acid (25 g, 215 mmol, 1 equiv) in DCM (600 ml) was added TEA (30 ml, 1 equiv), EDCl (61.9 g, 1.5 equiv), N,O-dimethyhydroxylamine (21 g, 1 equiv) followed by DMAP (0.263 g, 0.01 equiv). The reaction mixture was stirred at RT overnight and then washed with 1M HCl and 1M NaOH. The organic portion was dried ($MgSO_4$) and concentrated in vacuo to afford the title product; $[M+H]^+$ 160, NMR ($CDCl_3$) 1.9 (1H, m), 2.05 (2H, m), 2.2 (1H, m), 3.2 (3H, s, $NCH_3$), 3.7 (3H, s, $OCH_3$), 3.9 (1H, m, CHO), 4.05 (1H, m, CHO), 4.8 (1H, m, CHO).

Step 2: (R)-1-(tetrahydrofuran-2-yl)propan-1-one

To a cooled (0° C.) solution of (R)-N-methoxy-N-methyltetrahydrofuran-2-carboxamide (20.15 g, 1 equiv) in THF (250 ml) was added ethyl magnesium bromide (44.3 ml of a 3M solution in THF, 1.05 equiv) The reaction was stirred at −78° C. for 1 h and then quenched with saturated $NH_4Cl$ solution. EtOAc was added and the organic portion was separated and washed further with saturated $NH_4Cl$ solution, dried ($MgSO_4$) and concentrated in vacuo to afford the title compound; NMR (CDCl3) 1.05 (3H, t, CH3), 1.9 (3H, m), 2.2 (1H, m, CH), 2.6 (2H, m, $CH_2$), 3.95 (2H, $CH_2O$), 4.3 (1H, m, CHO).

Step 3: (R)-1-(tetrahydrofuran-2-yl)propan-1-ol

To a cooled (0° C.) solution of (R)-1-(tetrahydrofuran-2-yl)propan-1-one (16.16 g, 1 equiv) in MeOH was added portionwise sodium tetrahydroborate (4.77 g, 1 equiv). After stirring at 0° C. for 1 hour, the reaction was quenched with 5M HCl and allowed to stir for further for 10 minutes. The mixture was concentrated in vacuo to remove MeOH and EtOAc and water were added. The organic portion was separated and the aqueous layer extracted several times with EtOAc. The combined organic extracts were dried ($MgSO_4$) and concentrated in vacuo to afford the title compound.

Step 4: (2R)-2-(1-azidopropyl)tetrahydrofuran

To a cooled (0° C.) solution of (R)-1-(tetrahydrofuran-2-yl)propan-1-ol (13.78 g, 1 equiv) in DCM (250 ml) was added TEA (16.07 g, 1.5 equiv) and methanesulfonyl chloride (18.19 g, 1.5 equiv). The reaction was stirred at 0° C. After 50 min, the reaction was quenched with aq. sat. $NaHCO_3$. The organic layer was washed with aq. sat $NaHCO_3$, dried ($MgSO_4$), filtered and concentrated in vacuo. The reaction was allowed to cool and partitioned between brine and EtOAc. The aqueous portion was separated and further extracted with EtOAc. The combined organic extracts were dried ($MgSO_4$), filtered and concentrated in vacuo. Purification of the crude product by chromatography on silica affords the title compound. 1.05 (3H, m, $CH_3$ of two diastereomers), 1.6 (3H, m), 1.95 (3H, m), 3.05 (0.5H, m, $CHN_3$ of one diastereomer), 3.45 (0.5H, m, $CHN_3$ of one diastereomer), 3.8 (1H, m, CHO), 3.9 (2H, m, CH2O).

Step 5: (R)-1-(tetrahydrofuran-2-yl)propan-1-amine

A solution of (2R)-2-(1-azidopropyl)tetrahydrofuran (1.9 g, 12.24 mmol, 1 equiv) in EtOH/AcOH (105 ml of a 100:5 mixture) and 10% Pd/C CATCart (12.24 mmol, 1 equiv) was placed under a positive pressure of hydrogen for 8 hours. The product mixture was concentrated in vacuo and diluted with DCM. The mixture was passed down a 10 g SCX-2 cartridge (resin loading 0.67 mmol/g), eluting with methanol followed by 2M ammonia in EtOH. The appropriate fractions were concentrated in vacuo to afford the title compound. 1.0 (3H, t, CH3), 1.3 (1H, m), 1.6 (2H, m), 1.9 (3H, m), 2.6 (0.5H, m, CHNH2 of one diastereomer), 2.8 (0.5H, m, CHNH2 of one diastereomer), 3.6 (1H, m, CHO), 3.75 (1H, m, CHO), 3.85 (1H, m, CHO).

Intermediate DB (R)-1-(Tetrahydro-furan-2-yl)-propylamine

Step 1: (R)-2-((R)-1-Azidopropyl)tetrahydrofuran

This compound was prepared from (S)-(R)-1-(tetrahydrofuran-2-yl)-propan-1-ol analogously to (2R)-2-(1-azidopropyl)tetrahydrofuran (Intermediate DA step 4).

Step 2: tert-Butyl (R)-1-((R)-tetrahydrofuran-2-yl)propylcarbamate

To a solution of (R)-2-((R)-1-azidopropyl)tetrahydrofuran (step 1) (2.11 g, 13.6 mmol) in THF (60 ml) and H20 (10 ml) was added triphenylphosphine (4.28 g, 16.32 mmol). The reaction was heated at 50° C. overnight and then allowed to cool to RT. Sodium bicarbonate (11.42 g, 136 mmol) and Boc-anhydride (4.16 g, 19.04 mmol) were added and the reaction mixture was heated at 40° C. The reaction was allowed to cool to RT and EtOAc was added. The aqueous and organic layers were separated. The aqueous layer was extracted with EtOAc. The combined organic layers were dried (MgSO4), filtered and concentrated in vacuo. The crude product mixture was purified by flash chromatography on silica gel (40 g) eluting with an EtOAc/iso-hexane (gradient 0-40%) to afford the title product; $^1H$ NMR ($CDCl_3$) δ 0.98 (3H, t, CH3), 1.45 (9H, s, (CH3)3), 1.6 (3H, m), 1.9 (3H, m), 3.5 (1H, m), 3.7 (1H, m), 3.85 (2H, m), 4.6 (1H, m).

Step 3: (R)-1-((R)-tetrahydrofuran-2-yl)propan-1-amine

To a solution of tert-butyl (R)-1-((R)-tetrahydrofuran-2-yl)propylcarbamate (2.67 g, 11.64 mmol) in 1,4-dioxane (80 ml) was added 5M HCl (5 ml). The reaction was then heated at 70° C. for 5.5 hours and after cooling to RT, the mixture was concentrated in vacuo to afford the title compound; $^1H$ NMR (MeOD) δ1.09 (3H, t, CH3), 1.7 (3H, m), 2.0 (2H, m), 2.15 (1H, m), 3.0 (1H, m), 3.88 (3H, m).

Intermediate DC 1-(6-methylpyridin-2-yl)propan-1-amine

This compound was prepared from 1-(6-methyl-pyridin-2-yl)-propan-1-ol analogously to (R)-1-(tetrahydro-furan-2-yl)-propylamine (Intermediate DB). The final deprotection step was carried out using 5% TFA in DCM; $[M+H]^+$ 151.

Intermediate DD

1-(pyridin-3-yl)propan-1-amine

This compound was prepared from 1-pyridin-3-yl-propan-1-ol analogously to (R)-1-(tetrahydro-furan-2-yl)-propylamine (Intermediate DB). The final deprotection step was carried out using 5% TFA in DCM; $[M+H]^+$ 136.

Intermediate E

((R)-1-((2R,5R)-5-methyl-tetrahydro-furan-2-yl)-propylamine para-toluenesulfonate salt

Step 1: [(R)-1-(5-Methyl-furan-2-yl)-propyl]-carbamic acid tert-butyl ester An ice-cooled solution of (R)-1-(5-methyl-furan-2-yl)-propylamine PTSA salt (591 mg, 1.90 mmol) (prepared according to the procedure described in US 2004/0209946 (page 19) and Et₃N (0.264 ml, 1.90 mmol) in dry MeCN (4 ml) was treated with BOC anhydride (456 mg, 2.09 mmol) at room temperature under an inert atmosphere of nitrogen. The reaction mixture was stirred at 0° C. for 30 minutes and allowed to warm to room temperature. The solvent was evaporated in vacuo and the resulting oil was dissolved in EtOAc (20 ml) and washed with 1M HCl (10 ml), Na₂SO₄ (10 ml), brine (10 ml), dried (MgSO₄) and concentrated in vacuo. The resulting oil was dissolved in a minimal volume of EtOH and triturated with EtOAc/Et₂O to afford the title compound; $[M+H]^+$ 332

Step 2: [(R)-1-(2R,5R)-(5-Methyl-tetrahydro-furan-2-yl)-propyl]-carbamic acid tert-butyl ester 10% Pd/C (55 mg) was added to a solution of [(R)-1-(2R,5R)-(5-methyl-furan-2-yl)-propyl]-carbamic acid tert-butyl ester (453 mg, 1.89 mmol) in dry MeOH (20 ml) at room temperature under an inert atmosphere of nitrogen. The resulting mixture was placed under a positive atmosphere of hydrogen and stirred vigorously. The catalyst was removed by filtration and the filtrate was reduced in vacuo to afford the title compound as a mixture of two diastereomers.

Step 3: ((R)-1-((2R,5R)-5-methyl-tetrahydro-furan-2-yl)-propylamine para-toluenesulfonate salt To an ice-cooled solution of [(R)-1-(2R,5R)-(5-methyl-tetrahydro-furan-2-yl)-propyl]-carbamic acid tert-butyl ester (416 mg, 1.71 mmol) in dry DCM (4 ml) was added TFA (200 μl, 1.41 mmol) under an inert atmosphere of nitrogen. After stirring at room temperature for 3 h, the mixture was diluted with EtOAc (15 ml) and washed with saturated aqueous Na₂CO₃. The organic portion was dried (Na₂SO₄) and then para-toluenesulfonic acid (147 mg, 0.77 mmol) was added. After stirring, the solvent was removed in vacuo and recrystallisation from MeCN affords the title compound as a white solid. ¹H NMR (DMSO) 0.90 (3H, t, CH3), 1.20 (3H, d, CH3), 1.45 (2H, m, 2×CH), 1.59 (1H, m, CH), 1.65 (1H, m, CH), 1.95 (2H, m, CH2), 2.30 (3H, s, CH3), 2.93 (1H, m, CH), 3.75 (1H, dd, CH), 3.95 (1H, m, CH), 7.10 (2H, d, 2×CH), 7.48 (2H, d, 2×CH), 7.75 (3H, s, NH3+).

Intermediate FA

6-Chloro-3-(2-ethoxy-3,4-dioxo-cyclobut-1-enylamino)-2-hydroxy-N-methoxy-N-ethyl-benzenesulfonamide

Step 1: 2-tert-Butyl-6-chloro-benzooxazole-7-sulfonic acid ethyl-methoxy-amide N-Ethyl-O-methylhydroxylamine hydrochloride (Intermediate G) (3.39 g, 30.4 mmol) was suspended in dry THF (20 ml) and cooled to 0° C. in an ice bath while stirring. TEA (4.24 ml, 30.4 mmol) was added followed by dropwise addition of 2-tert-butyl-6-chloro-benzooxazole-7-sulfonyl chloride (US 2007/0249672 page 9) (4.68 g, 15.19 mmol) in THF (10 ml) over 2.5 hours. The reaction mixture was stirred at room temperature for 30 minutes. The reaction mixture was diluted with EtOAc and washed with H₂O, brine, dried (MgSO₄) and concentrated in vacuo. The residue was purified by flash chromatography, eluting with 0-10% EtOAc in iso-hexane, to yield a white solid $[M+H]^+$ 347.2

Step 2: 3-Amino-6-chloro-2-hydroxy-N-methoxy-N-ethyl-benzenesulfonamide 2-tert-Butyl-6-chloro-benzooxazole-7-sulfonic acid ethyl-methoxy-amide (2.7 g, 7.78 mmol) in dioxane (15 ml) was treated with a mixture of concentrated sulphuric acid (3.5 ml) and water (3.5 ml). The reaction mixture was heated at 80° C. for a total of 8 h and then allowed to cool to RT. Dioxane was removed in vacuo and the resulting aqueous mixture was treated with 1M NaOH (aq) until pH7 was attained. The reaction mixture was extracted with EtOAc, dried (MgSO₄) and concentrated in vacuo to afford the title compound as a brown solid; $[M+H]^+$ 281.1.

Step 3: 6-Chloro-3-(2-ethoxy-3,4-dioxo-cyclobut-1-enylamino)-2-hydroxy-N-methoxy-N-ethyl-benzenesulfonamide A solution of 3,4-diethoxy-3-cyclobutene-1,2-dione (0.30 g, 1.76 mmol) in ethanol (5 ml) was treated with TEA (250 μl, 1.80 mmol) and the reaction mixture was heated to 45° C. A solution of 3-amino-6-chloro-2-hydroxy-N-methoxy-N-ethyl-benzenesulfonamide (0.58 g, 2.07 mmol) in EtOH (5 ml) was added dropwise to the reaction mixture. The reaction mixture was stirred at 45° C. for 1 hour and then concentrated in vacuo. The residue was purified using flash chromatography (50% EtOAc in iso-hexane) to furnish a solid $[M+H]^+$ 405.2.

Intermediate FB

3-(4-Chloro-2-hydroxy-3-(isoxazolidin-2-ylsulfonyl)phenylamino)-4-ethoxycyclobut-3-ene-1,2-dione This compound was prepared analogously to 6-chloro-3-(2-ethoxy-3,4-dioxo-cyclobut-1-enylamino)-2-hydroxy-N-methoxy-N-ethyl-benzenesulfonamide (Intermediate FA) by replacing N-ethyl-O-methylhydroxylamine hydrochloride (Intermediate G) with isoxazolidine hydrochloride. $[M+H]^+$ 402.9

Intermediate FC and FD

These compounds namely, 3-[4-chloro-2-hydroxy-3-((S)-4-hydroxy-isoxazolidine-2-sulfonyl)-phenylamino]-4-ethoxy-cyclobut-3-ene-1,2-dione (Intermediate FC) and 3-[4-chloro-2-hydroxy-3-((R)-4-hydroxy-isoxazolidine-2-sulfonyl)-phenylamino]-4-ethoxy-cyclobut-3-ene-1,2-dione (Intermediate FD) are prepared analogously to 6-chloro-3-(2-ethoxy-3,4-dioxo-cyclobut-1-enylamino)-2-hydroxy-N-methoxy-N-ethyl-benzenesulfonamide (Intermediate FA) by replacing N-ethyl-O-methylhydroxylamine hydrochloride (Intermediate G) with hydrochloride salts of either (S)-isoxazolidin-4-ol (Intermediate I) or (R)-isoxazolidin-4-ol (Intermediate J). $[M+H]^+$ 418.9 and $[M+H]^+$ 418.9.

Intermediate FE

6-Chloro-3-(2-ethoxy-3,4-dioxo-cyclobut-1-enylamino)-2-hydroxy-N-(2-methoxy-ethoxy)-N-methyl-benzenesulfonamide This compound was prepared analogously to 6-chloro-3-(2-ethoxy-3,4-dioxo-cyclobut-1-enylamino)-2-hydroxy-N-methoxy-N-ethyl-benzenesulfonamide (Intermediate FA) by replacing N-ethyl-O-methylhydroxylamine hydrochloride (Intermediate G) with O-(2-Methoxy-ethyl)-N-methyl-hydroxylamine (Intermediate K). $[M+H]^+$ 435

Intermediate G

N-Ethyl-O-methyl-hydroxylamine hydrochloride

Step 1: N-methoxy carbamic acid ethyl ester

A stirred mixture of ethyl chloroformate (10.78 g, 99 mmol) and O-methylhydroxylamine hydrochloride (12.4 g, 148 mmol) in DCM (400 ml) was cooled using an acetonitrile-cardice bath. TEA (25.05 g, 248 mmol) was added dropwise over 10 minutes, and cooling was maintained for a further 10 minutes. The reaction mixture was stirred at room temperature for 30 minutes, washed with 1M HCl (aq), dried ($MgSO_4$) and concentrated in vacuo, to give a mixture of oil and solid. The oil was isolated, and NMR was consistent with proposed product; $^1H$ NMR (CDCl3) 1.3 (3H, t, CH3), 3.7 (3H, s, CH3), 4.2 (2H, q, CH2), 7.3 (1H, s)

Step 2: N-Ethyl-O-methyl-hydroxylamine hydrochloride

A stirred mixture of N-methoxy carbamic acid ethyl ester (10.45 g, 88 mmol) in DMF (50 ml) was cooled using an ice-bath. Sodium hydride (60% dispersion in oil) (3.65 g, 91 mmol) was added portionwise and the reaction mixture was stirred at room temperature for 1 hour. Bromoethane (9.56 g, 88 mmol) was added portionwise, and reaction mixture was heated at 80° C. for 4 hours. The mixture was partitioned between $H_2O$ and 1:1 EtOAc/$Et_2O$. The organic layer was washed with further $H_2O$, dried ($MgSO_4$) and concentrated in vacuo, to give an oil. The oil was heated at 65° C. for 5 hours in a mixture of KOH (12.4 g, 221 mmol), $H_2O$ (15 ml) and EtOH (15 ml). The resulting solution was distilled into 2M HCl (aq), and concentrated in vacuo, to furnish an oil. $^1H$ NMR (CDCl3) 1.2 (3H, t, CH3), 3.2 (2H, q, CH2), 3.9 (3H, s, CH3), 12.1 (2H, s)

Intermediate H

(R)-2-Amino-3-methyl-butan-1-ol

This compound was prepared according to the procedure described in WO 957257, Example 7.

Intermediate I and J

(S)-Isoxazolidin-4-ol and (R)-Isoxazolidin-4-ol

These compounds namely (S)-isoxazolidin-4-ol (Intermediate I) and (R)-isoxazolidin-4-ol (Intermediate J) are prepared according to the procedure of Journal of Molecular Catalysis B: Enzymatic (2001), 11(4-6), 255-263.

Intermediate K

O-(2-Methoxy-ethyl)-N-methyl-hydroxylamine

This compound is prepared according to the procedure described in 'Preparation of 7-aminopyrazolo[1,5-a]pyrimidines as agricultural fungicides and pesticides. Ger. Offen. (2003), 50 pp. DE 10223917 page 42.

Intermediate L

3-(2-Ethoxy-3,4-dioxocyclobut-1-enylamino)-N-ethyl-2-hydroxy-N-methoxy benzenesulfonamide

Step 1: 3-Amino-N-ethyl-2-hydroxy-N-methoxybenzenesulfonamide

A dispersion of 10% Pd/C (200 mg) in a solution of 3-amino-6-chloro-2-hydroxy-N-methoxy-N-ethyl-benzenesulfonamide (Int. FA step 2) (400 mg, 1.425 mmol) in EtOH (50 ml) was placed under a positive pressure of hydrogen at 0.5 bar above atmospheric pressure. After 5 hours, the catalyst was removed by filtration through Celite® (filter material), and the filtrate was reduced in vacuo. The resulting solid was used in the next step, without further purification.

Step 2: 3-(2-Ethoxy-3,4-dioxocyclobut-1-enylamino)-N-ethyl-2-hydroxy-N-methoxy benzenesulfonamide This compound was prepared analogously to 6-Chloro-3-(2-ethoxy-3,4-dioxo-cyclobut-1-enylamino)-2-hydroxy-N-methoxy-N-methyl-benzenesulfonamide (Intermediate A step 3) by replacing 3-amino-6-chloro-2-hydroxy-N-methoxy-N-methyl-benzenesulfonamide with 3-amino-N-ethyl-2-hydroxy-N-methoxybenzenesulfonamide (step 1). $[M+H]^+$ 371

Intermediate M

1-(Pyrazin-2-yl)propan-1-amine

Step 1: 2-(1-Azidopropyl)pyrazine

The title compound is prepared from 1-(pyrazin-2-yl)propan-1-ol (prepared according to the procedure of 'Some reactions of mono substituted pyrazine monoxides' Journal of Heterocyclic Chemistry (1982), 19(5), 1061-7, Compound 18) analogously to (2R)-2-(1-azidopropyl)tetrahydrofuran (Intermediate DA, step 4).

Step 2: 1-(Pyrazin-2-yl)propan-1-amine

The 2-(1-azidopropyl)pyrazine (56 mg) was dissolved in the THF (5 ml) and water (1 ml) and the PS-$PPh_3$ (225 mg) added. The reaction mixture was heated to 50° C. and left to stir for approx. 20 hours. The mixture was filtered under vacuum and rinsed with DCM (a precipitate formed and re-dissolved with MeOH) then MeOH. The filtrate was evaporated to yield the title compound as a yellow oil which was used without further purification. $[M+H]^+$ 138.

Intermediate N

(S)-1-methoxy-4-methylpentan-2-amine (S)-2-amino-4-methylpentan-1-ol (0.276 ml, 2.133 mmol) was added to a stirred, ice-bath cooled suspension of KH (267 mg, 2.327 mmol) in THF (10 ml) under nitrogen. The resulting mixture was allowed to warm to room temperature and stirred for ~10 minutes and then treated with MeI (0.121 ml, 1.939 mmol). After stirring for 30 minutes the reaction mixture was quenched by addition of saturated NH₄Cl(aq) (~20 ml) and extracted with EtOAc (25 ml×2). The combined organic phases were dried over MgSO₄, filtered under vacuum and the filtrate was evaporated to afford an orange oil. The oil was purified by chromatography on silica eluting with 10% (2M NH₃ in MeOH)/DCM to afford the title compound which was used without further purification.

Intermediate O (R)-1-(pyridin-2-yl)propan-1-amine

Step 1: (S,E)-3-Methyl-N-(pyridin-2-ylmethylene)-1-(trimethylsilyloxy)butan-2-amine To a solution of pyridyl-2-carboxaldehyde (14.22 g, 133 mmol) and (R)-Valinol (13.7 g, 133 mmol) in DCM (150 ml) was added MgSO₄ (63.9 g, 531 mmol). The reaction was allowed to stir at room temperature overnight and then filtered to remove MgSO₄ and concentrated in vacuo. The residue was dissolved in DCM (150 ml) and cooled on an ice bath. TEA (14.78 g, 146 mmol) and TMSCl (15.87 g, 146 mmol) were added and the mixture was stirred at room temperature overnight. The mixture was filtered and the filtrate was concentrated in vacuo. The resulting residue was taken up in 1:1 Et2O:cyclohexane. The solid was filtered off and the filtrates concentrated to afford the title compound as an orange/brown oil.

Step 2: (S)-3-methyl-2-((R)-1-(pyridin-2-yl)propylamino)butan-1-ol

To a solution of imine (10.78 g, 40.8 mmol) in THF (100 ml) cooled to –78° C. was added a solution of ethyl lithium (26.4 ml, 1.7 M in dibutyl ether). The mixture was stirred at –78° C. and after 1 h, 5M HCl was added and stirring continued at RT overnight. The reaction mixture was diluted with EtOAc and H₂O. The aqueous and organic layers were separated and the aqueous layer was further extracted with EtOAc. The combined organic extracts were dried (MgSO₄), filtered and concentrated in vacuo to afford the title compound which was used without further purification. [M+H]⁺ 223.1.

Step 3: (R)-1-(pyridin-2-yl)propan-1-amine

To a solution of (S)-3-methyl-2-((R)-1-(pyridin-2-yl)propylamino)butan-1-ol (step 2, crude product) (40.8 mmol) in MeOH (250 ml) was added methylamine (60 ml of a 40% aqueous solution) followed by a solution of periodic acid (37.2 g, 163 mmol) in water (70 ml). The mixture was stirred at RT overnight and the resulting white solid precipitate was filtered off. The filtrate was concentrated in vacuo to remove the MeOH. The residual aqueous layer was then extracted with EtOAc. The combined organic layers were dried (MgSO₄), filtered and concentrated in vacuo Purification of the crude product by chromatography on silica eluting with a 0-20% MeOH/DCM gradient affords the title product; [M+H]⁺ 137.

The invention claimed is:

1. The compound which is selected from the group consisting of:

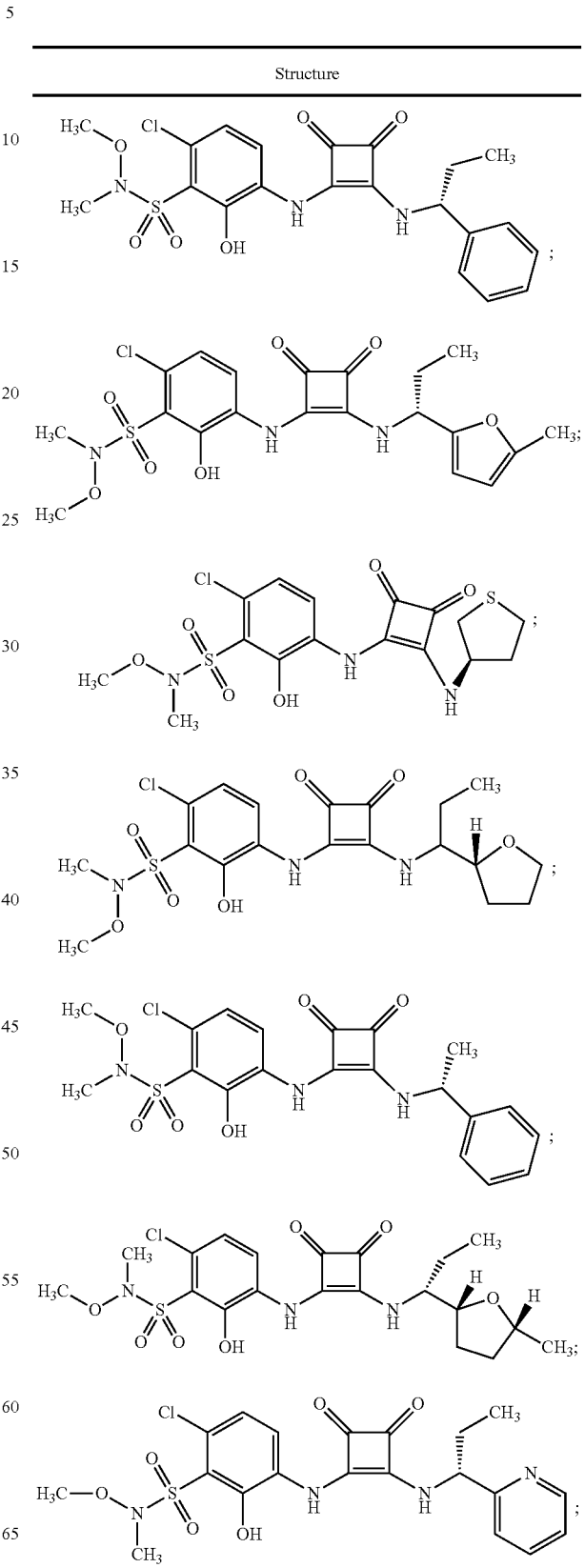

| 77 -continued | | 78 -continued |
|---|---|---|
| Structure | | Structure |
| 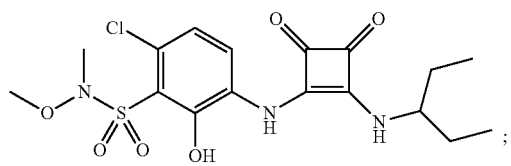 | | 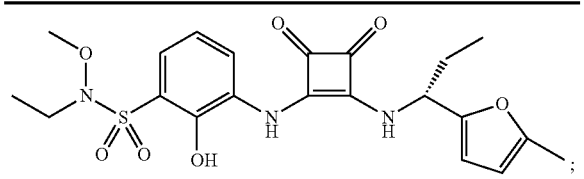 |
| 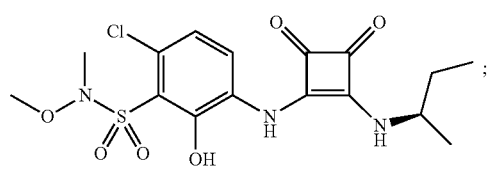 | | 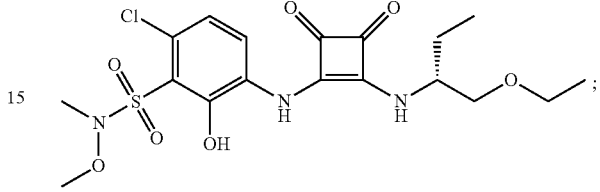 |
| 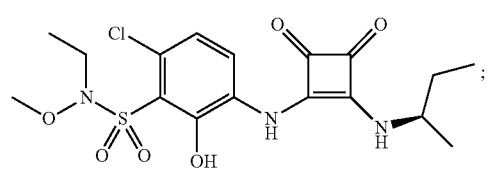 | | 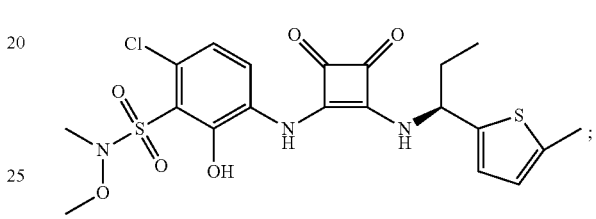 |
| 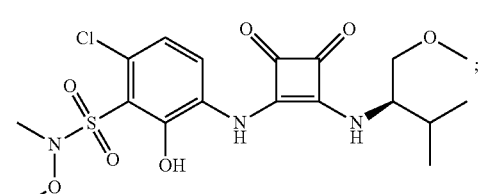 | | 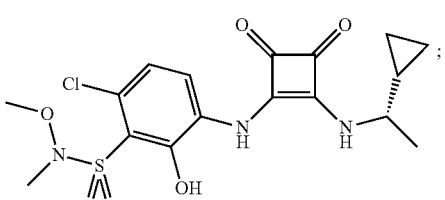 |
| 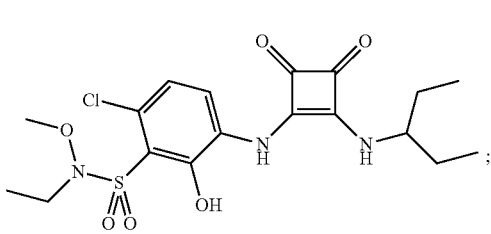 | | 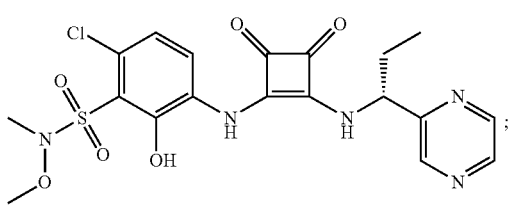 |
| 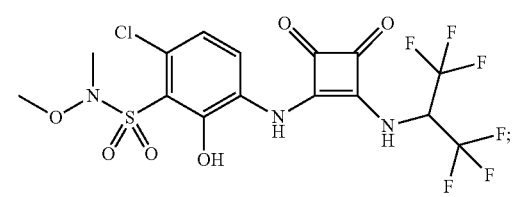 | | 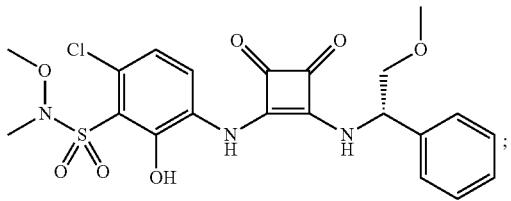 |
| 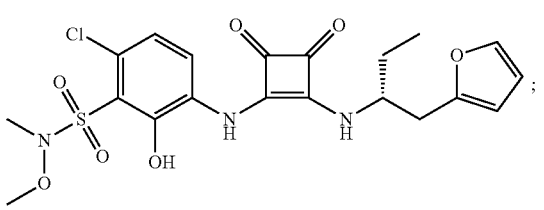 | | 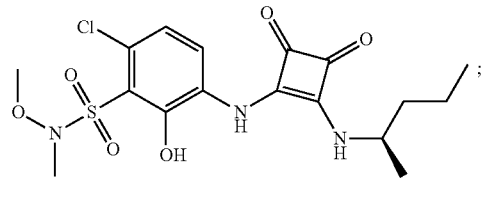 |
| 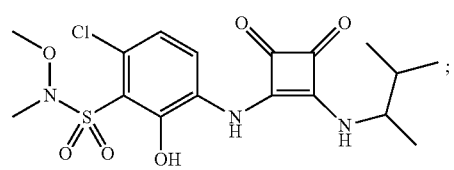 | | 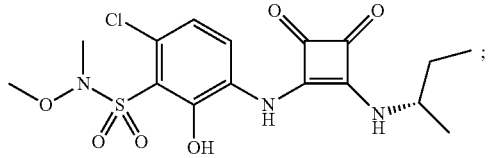 |

| Structure | | Structure |
|---|---|---|
| 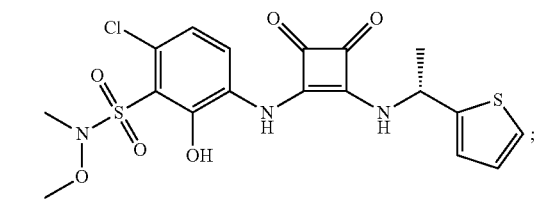 | 5 | 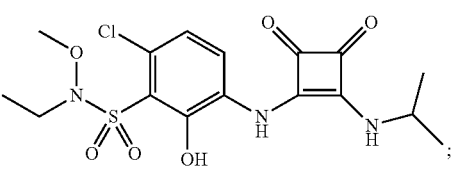 |
| 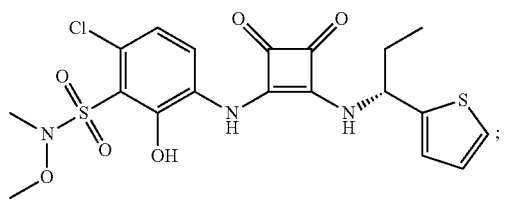 | 15 | 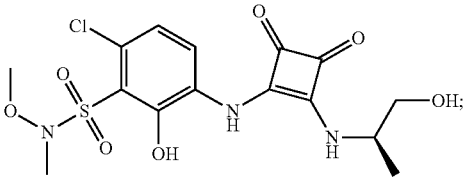 |
| 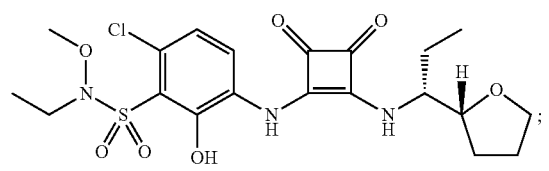 | 25 | 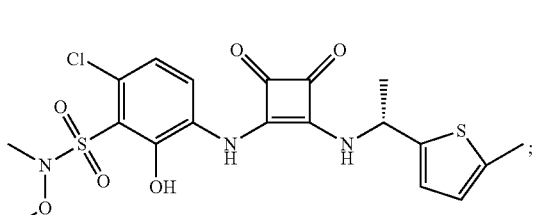 |
| 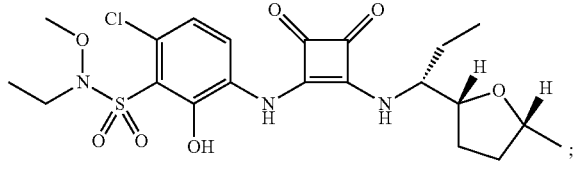 | 30 | 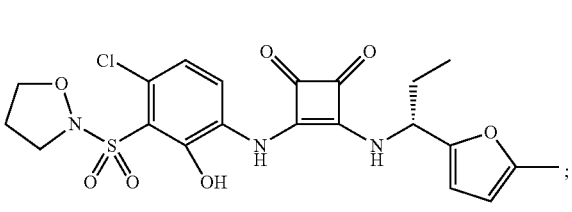 |
| 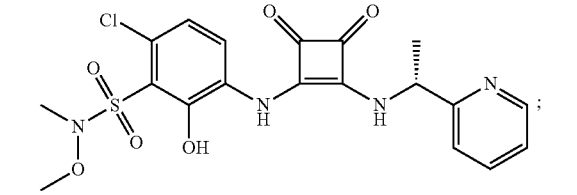 | 40 | 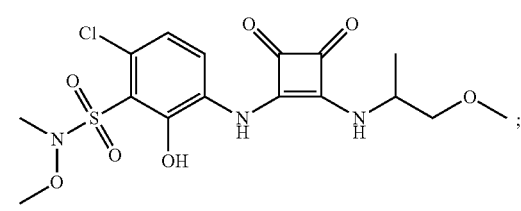 |
| 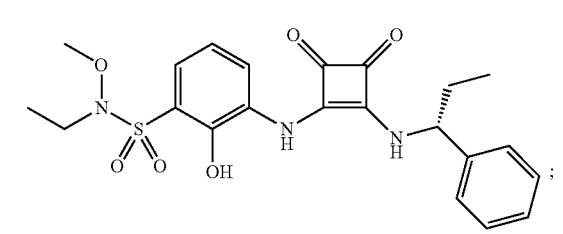 | 50 | 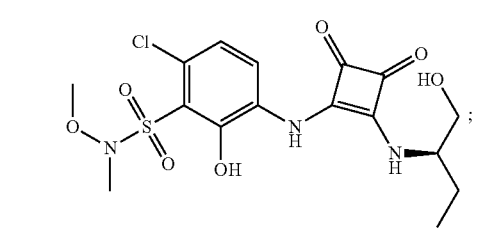 |
| 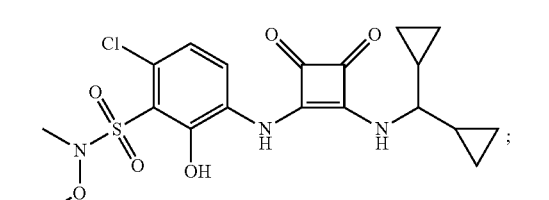 | 60 | 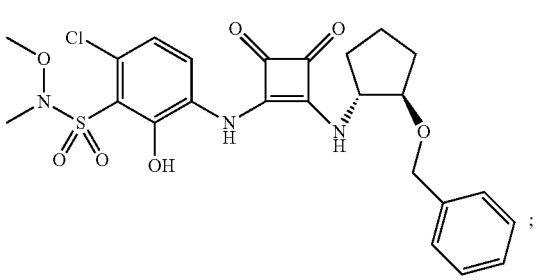 |
| 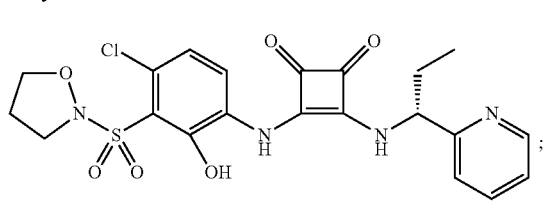 | 65 | |

| 81 -continued | | 82 -continued |
|---|---|---|
| Structure | | Structure |
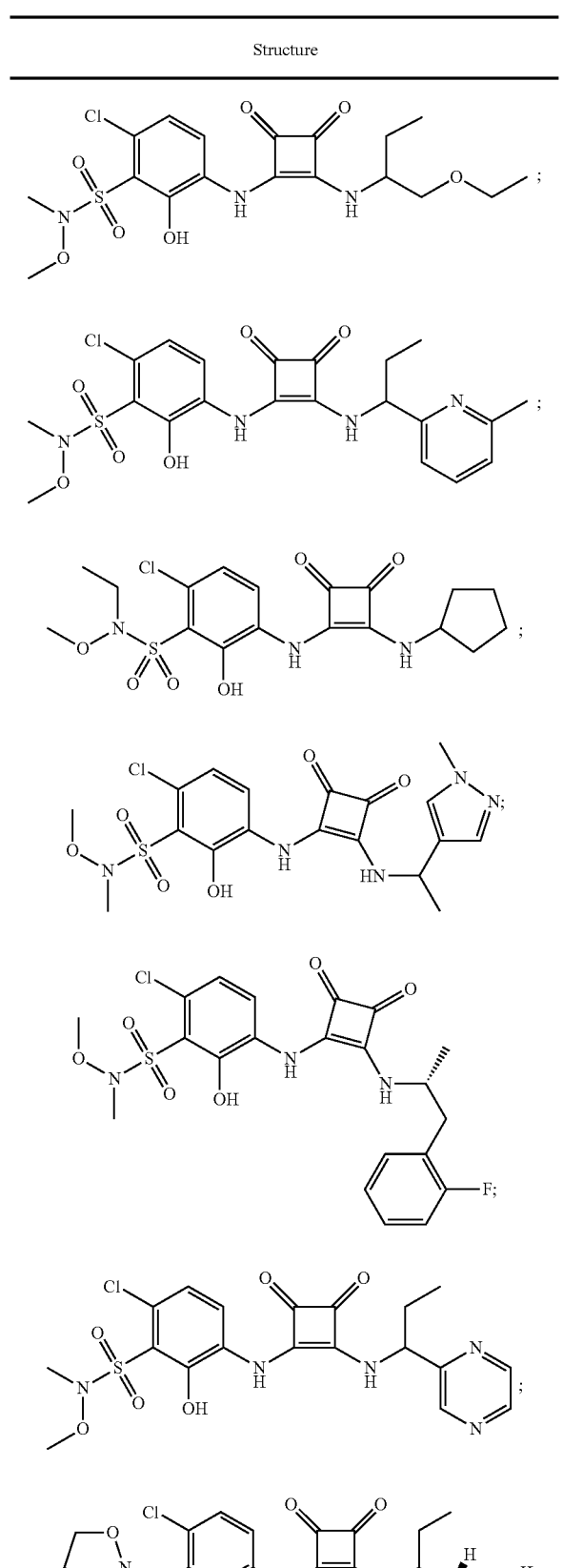
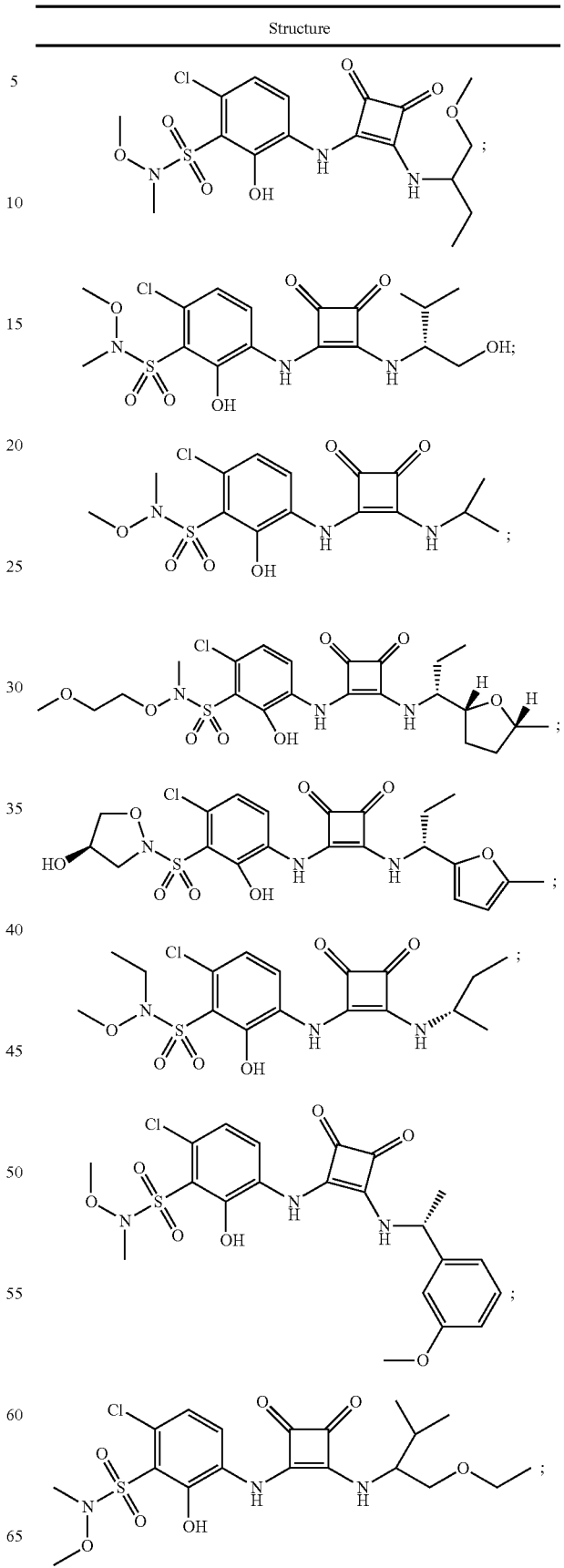

| 83 -continued | 84 -continued |
|---|---|
| Structure | Structure |
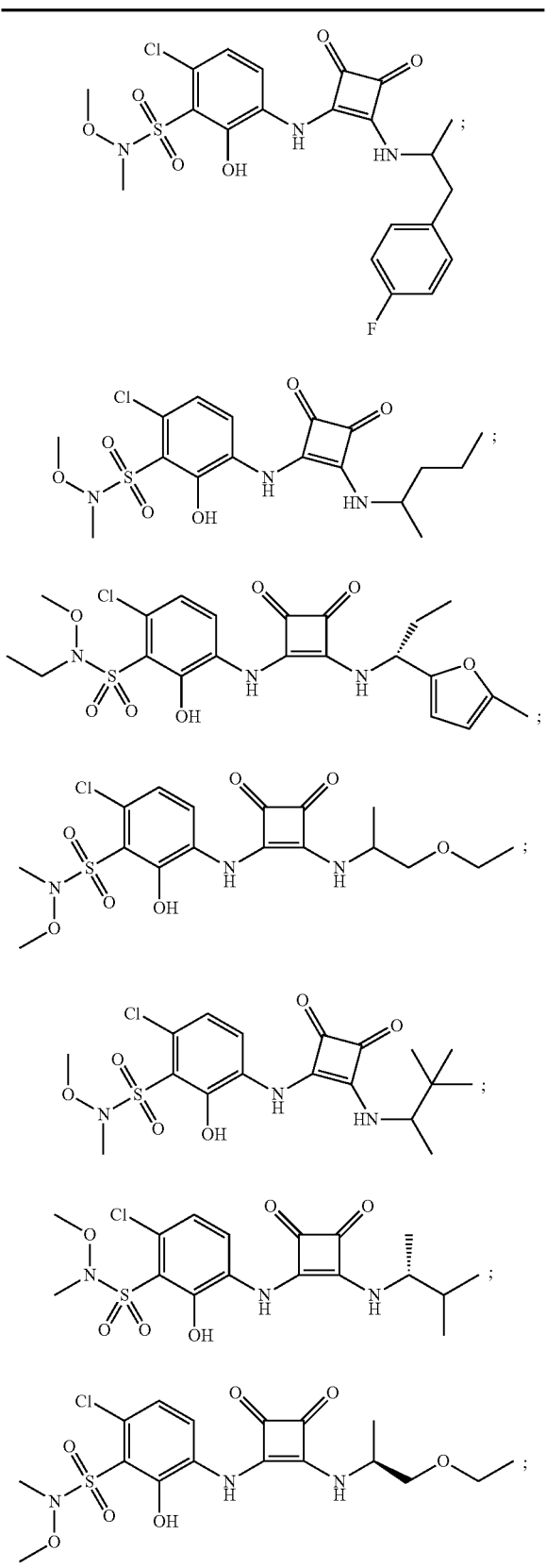
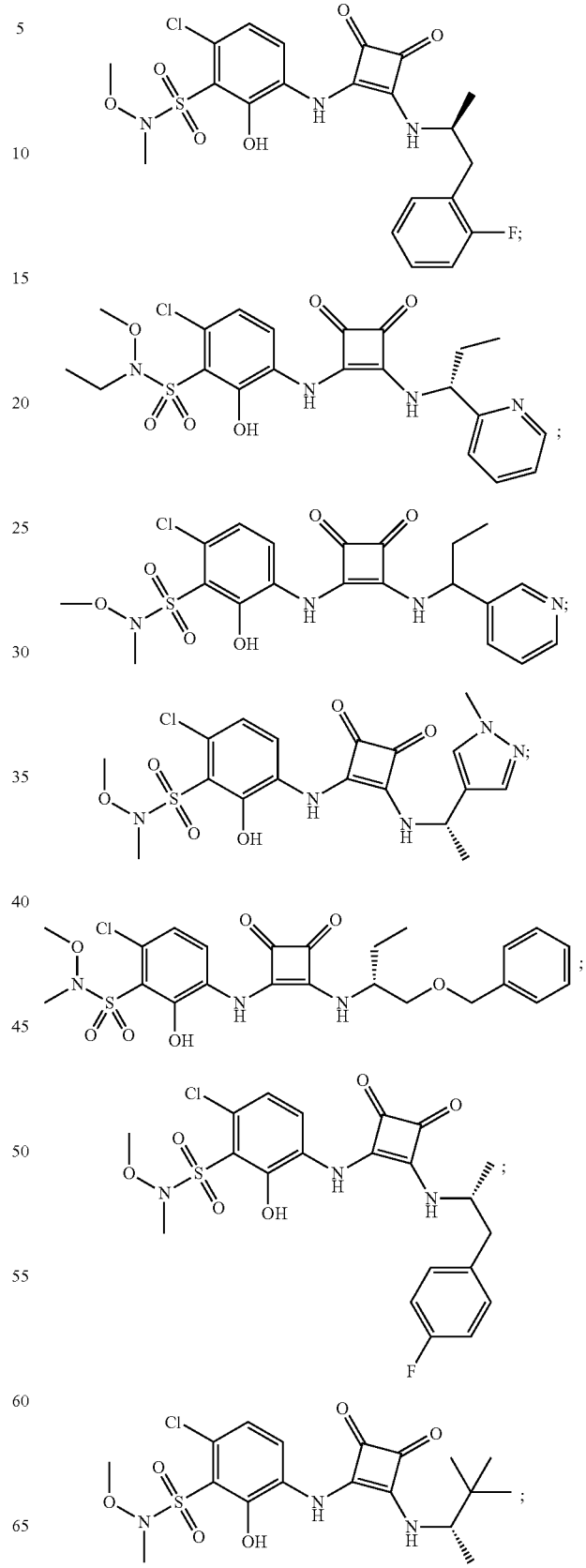

| 85 -continued | 86 -continued |
|---|---|
| Structure | Structure |
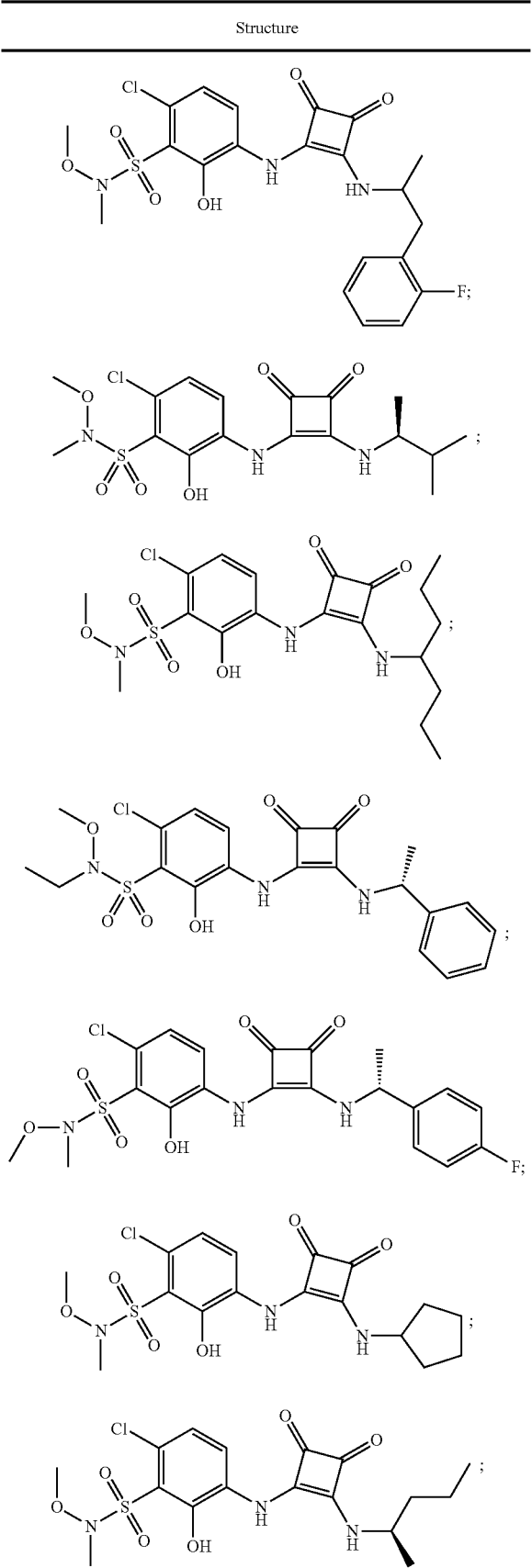
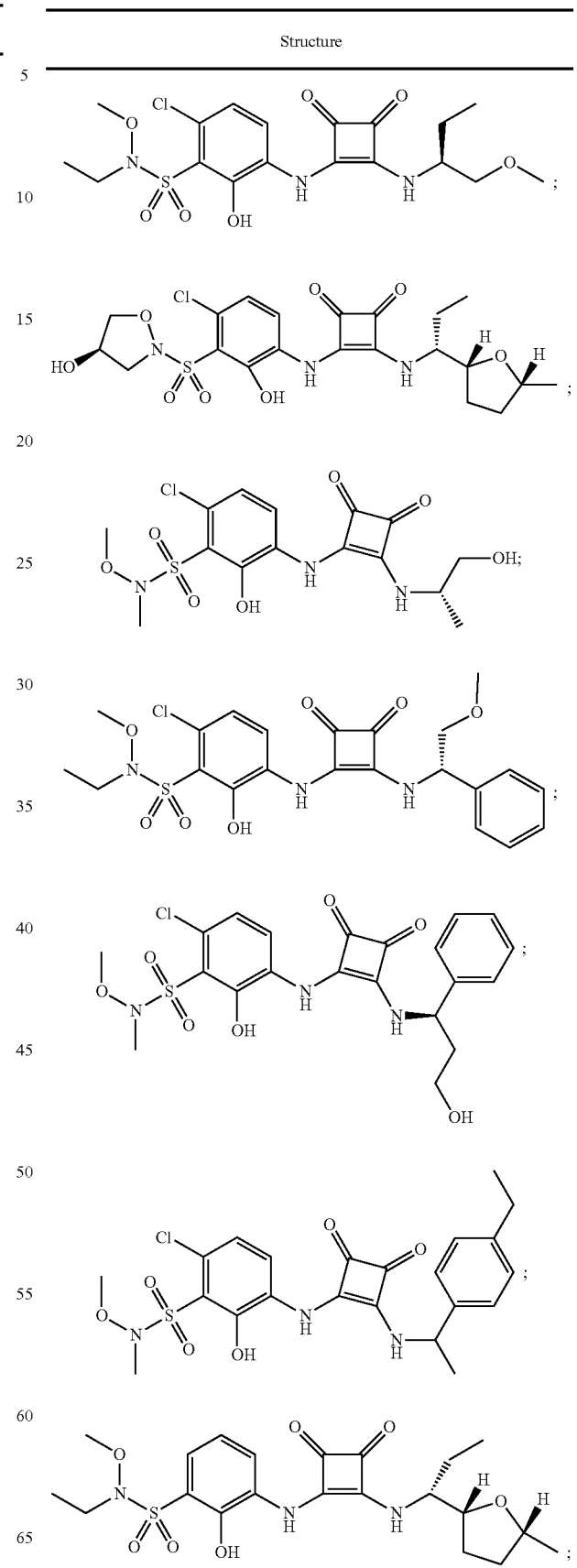

| 87 | 88 |
|---|---|
| -continued | -continued |
| Structure | Structure |
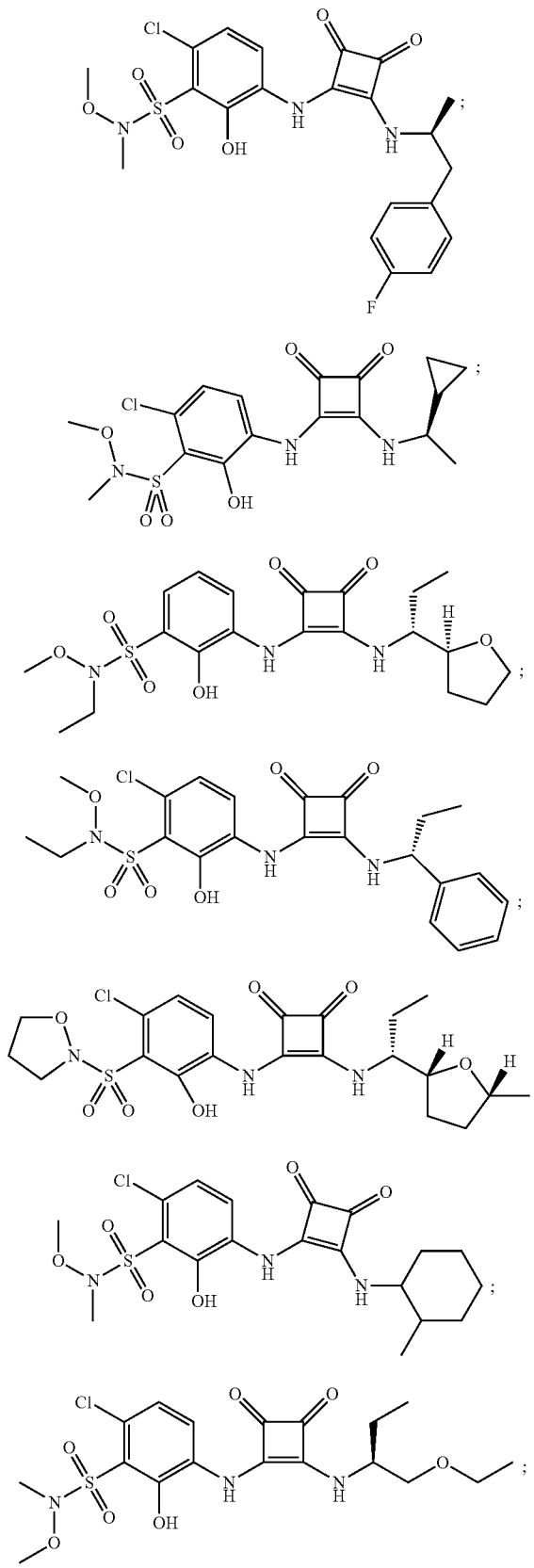
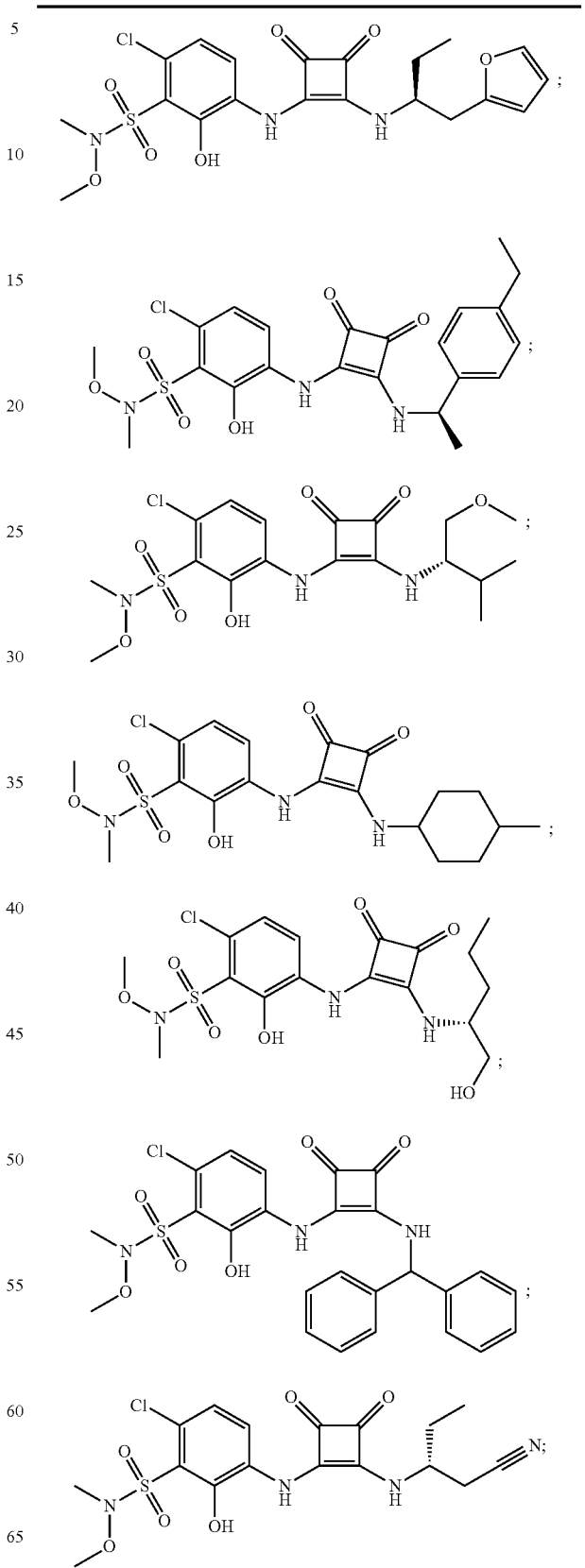

| 89 -continued | 90 -continued |
|---|---|
| Structure | Structure |
| 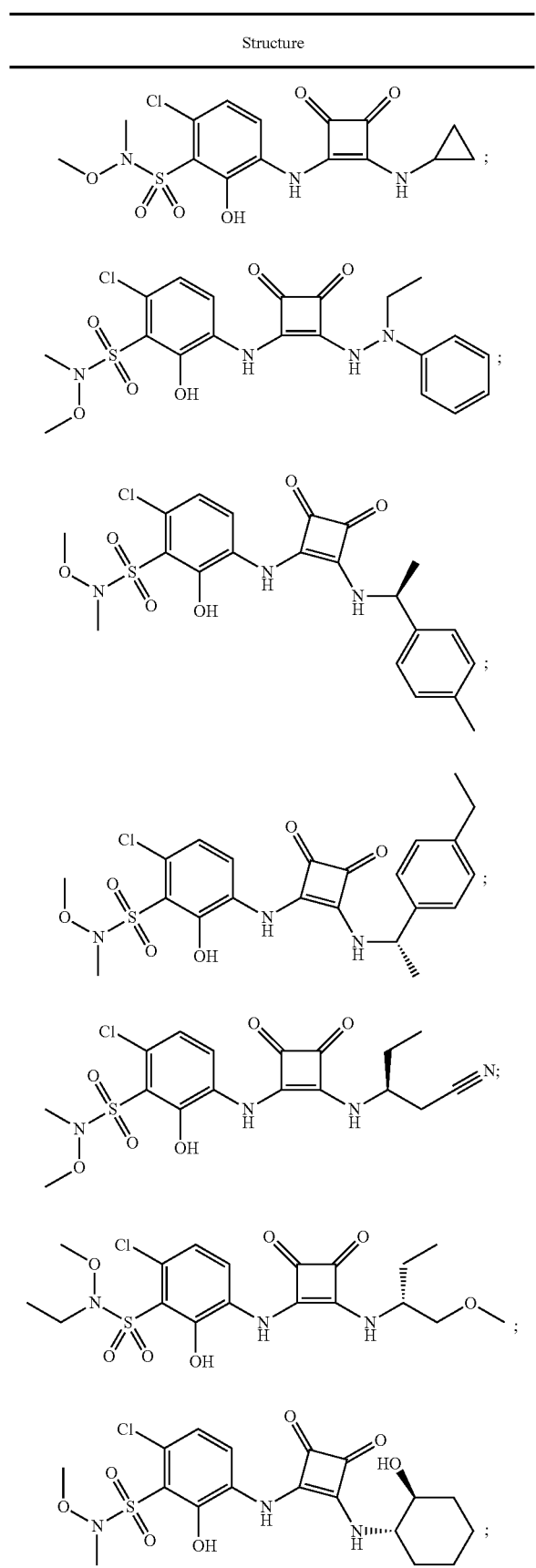 | 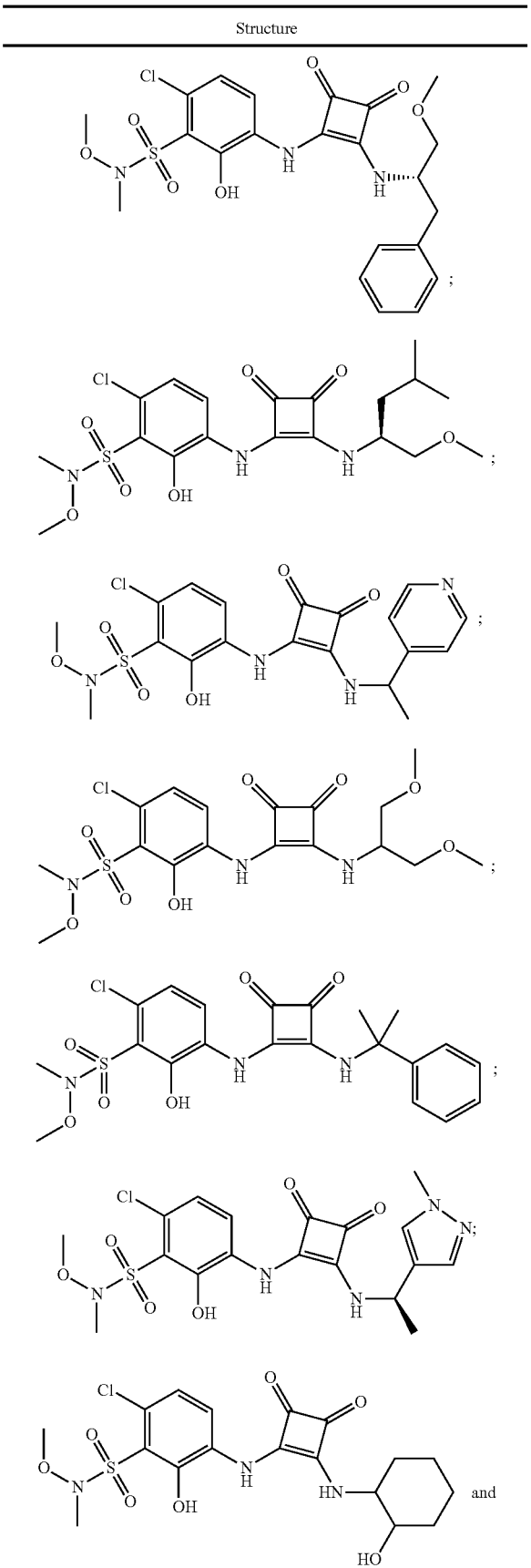 |

| Structure |
|---|
| 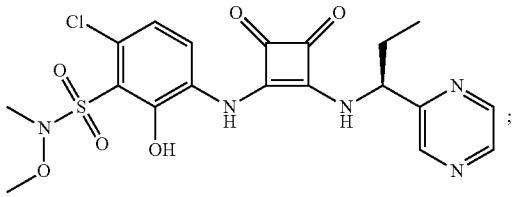 | or a pharmaceutically acceptable salt thereof.

2. The compound of claim 1, wherein the compound is 6-chloro-2-hydroxy-N-methoxy-N-methyl-3-{2-[(R)-1-(5-methyl-furan-2-yl)-propylamino]-3,4-dioxo-cyclobut-1-enyl amino}-benzenesulfonamide, or a pharmaceutically acceptable salt thereof.

3. The compound of claim 1, wherein the compound is 6-chloro-3-{3,4-dioxo-2-[(R)-1-(tetrahydro-furan-2-yl)-propylamino]-cyclobut-1-enylamino}-2-hydroxy-N-methoxy-N-methyl-benzenesulfonamide, or a pharmaceutically acceptable salt thereof.

4. The compound of claim 1, wherein the compound is 6 chloro-2-hydroxy-N-methoxy-N-methyl-3-{2-[(R)-1-((2R,5R)-5-methyl-tetrahydro-furan-2-yl)-propylamino]-3,4-dioxo-cyclobut-1-enylamino}-benzenesulfonamide, or a pharmaceutically acceptable salt thereof.

5. The compound of claim 1, wherein the compound is 6-chloro-3-[3,4-dioxo-2-((R)-1-pyridin-2-yl-propylamino)-cyclobut-1-enylamino]-2-hydroxy-N-methoxy-N-methyl-benzenesulfonamide, or a pharmaceutically acceptable salt thereof.

6. The compound of claim 1, wherein the compound is 6-chloro-3-[2-(1-ethyl-propylamino)-3,4-dioxo-cyclobut-1-enylamino]-2-hydroxy-N-methoxy-N-methyl-benzene-sulfonamide, or a pharmaceutically acceptable salt thereof.

7. The compound of claim 6, wherein the compound is the choline salt.

8. The compound of claim 1, wherein the compound is 6 chloro-3-{3,4-dioxo-2-[(R)-1-(tetrahydro-furan-2-yl)-propylamino]-cyclobut-1-enylamino}-N-ethyl-2-hydroxy-N-methoxy-benzenesulfonamide, or a pharmaceutically acceptable salt thereof.

9. The compound of claim 1, wherein the compound is 6-chloro-N-ethyl-2-hydroxy-3-(2-(isopropylamino)-3,4-dioxocyclobut-1-enylamino)-N-methoxybenzenesulfonamide, or a pharmaceutically acceptable salt thereof.

10. The compound of claim 1, wherein the compound is 3-(4-chloro-2-hydroxy-3-((S)-4-hydroxyisoxazolidin-2-ylsulfonyl)phenylamino)-4-((R)-1-((2R,5R)-5-methyltetrahydrofuran-2-yl)propylamino)cyclobut-3-ene-1,2-dione, or a pharmaceutically acceptable salt thereof.

11. The compound of claim 1, wherein the compound is 6-chloro-2-hydroxy-3-(2-(isopropylamino)-3,4-dioxocyclobut-1-enylamino)-N-methoxy-N-methylbenzenesulfonamide, or a pharmaceutically acceptable salt thereof.

12. The compound of claim 1, wherein the compound is (R)-6-chloro-N-ethyl-2-hydroxy-N-methoxy-3-(2-(1-(5-methylfuran-2-yl)propylamino)-3,4-dioxocyclobut-1-enylamino)benzenesulfonamide, or a pharmaceutically acceptable salt thereof.

13. The compound of claim 1, wherein the compound is 6-chloro-3-(2-(heptan-4-ylamino)-3,4-dioxocyclobut-1-enylamino)-2-hydroxy-N-methoxy-N-methylbenzenesulfonamide, or a pharmaceutically acceptable salt thereof.

14. The compound of claim 1, wherein the compound is 6-chloro-3-(2-(cyclopentylamino)-3,4-dioxocyclobut-1-enylamino)-2-hydroxy-N-methoxy-N-methylbenzenesulfonamide, or a pharmaceutically acceptable salt thereof.

15. The compound of claim 1, wherein the compound is 3-(3,4-dioxo-2-((R)-1-((S)-tetrahydrofuran-2-yl)propylamino)cyclobut-1-enylamino)-N-ethyl-2-hydroxy-N-methoxybenzenesulfonamide, or a pharmaceutically acceptable salt thereof.

16. A pharmaceutical composition, comprising:
the compound according to claim 1, or a pharmaceutically acceptable salt thereof, together with a pharmaceutically acceptable carrier or excipient.

* * * * *